US008834177B2

(12) United States Patent
Lapa et al.

(10) Patent No.: US 8,834,177 B2
(45) Date of Patent: Sep. 16, 2014

(54) COMPUTER-IMPLEMENTED METHOD OF AND SYSTEM FOR TEACHING AN UNTRAINED OBSERVER TO EVALUATE A GEMSTONE

(75) Inventors: Davy Lapa, Antwerp (BE); Christian Marie Joseph Ghislain Corneille Lenaerts, Bierges (BE)

(73) Assignee: Sarine Color Technologies Ltd. (IL)

( * ) Notice: Subject to any disclaimer, the term of this patent is extended or adjusted under 35 U.S.C. 154(b) by 0 days.

(21) Appl. No.: 13/620,492

(22) Filed: Sep. 14, 2012

(65) Prior Publication Data

US 2013/0078607 A1    Mar. 28, 2013

Related U.S. Application Data

(63) Continuation of application No. 10/918,616, filed on Aug. 12, 2004, now Pat. No. 8,317,521, which is a continuation of application No. 10/272,447, filed on Oct. 15, 2002, now Pat. No. 6,786,733.

(51) Int. Cl.
| | | |
|---|---|---|
| *G09B 25/00* | (2006.01) | |
| *A44C 17/00* | (2006.01) | |
| *A44C 19/00* | (2006.01) | |
| *G09B 5/02* | (2006.01) | |

(52) U.S. Cl.
USPC .................................. 434/386; 63/32; 356/30

(58) Field of Classification Search
USPC .................................. 434/386; 63/32; 356/30
See application file for complete search history.

(56) References Cited

U.S. PATENT DOCUMENTS

| | | | |
|---|---|---|---|
| 1,709,937 A | 4/1929 | Everard | |
| 1,735,815 A | 11/1929 | Treleaven | |
| 2,157,437 A | 5/1939 | Shipley | |
| 2,199,222 A | 4/1940 | Glaenzer | |
| 2,273,227 A | 2/1942 | Simmons | |
| 3,665,729 A | 5/1972 | Elbe | |

(Continued)

FOREIGN PATENT DOCUMENTS

| | | |
|---|---|---|
| EP | 0 464 824 A | 1/1992 |
| GB | 2 332 755 A | 6/1999 |

(Continued)

OTHER PUBLICATIONS

Tolkowsky M., "Diamond Design: A Study of the Reflection and Refraction of Light in a Diamond", 1999, 46 pgs.

(Continued)

*Primary Examiner* — Nikolai A Gishnock
(74) *Attorney, Agent, or Firm* — Greenberg Traurig, LLP

(57) ABSTRACT

A computer-implemented method teaches a user to evaluate a gemstone, such as a cut diamond. The method includes providing a computer system connected to an apparatus capable of capturing an image of a gemstone. The computer system is arranged to process a received image of a gemstone to determine one or more optical properties of the gemstone. In one aspect, the method presents on a display of the computer system a series of pre-stored screens comprising a graphical representation how the cut of a gemstone affects its light handling ability, and a user interface screen. The user interface screen allows the user to control the operation of the apparatus to measure the one or more optical properties of a particular gemstone provided to the apparatus, to view an image of the gemstone measured, and to view representations of the measured one or more optical properties.

11 Claims, 61 Drawing Sheets

(56) References Cited

U.S. PATENT DOCUMENTS

| | | |
|---|---|---|
| 3,858,979 A | 1/1975 | Elbe |
| 3,867,032 A | 2/1975 | Bruck |
| 3,947,120 A | 3/1976 | Bar-Issac et al. |
| 4,106,221 A | 8/1978 | Selon |
| 4,392,476 A | 7/1983 | Gresser et al. |
| 4,875,771 A | 10/1989 | Bowley et al. |
| 4,900,147 A | 2/1990 | Bowley et al. |
| 5,003,791 A | 4/1991 | Colliva |
| 5,124,935 A | 6/1992 | Wallner et al. |
| 5,143,212 A | 9/1992 | Roberts et al. |
| 5,146,288 A | 9/1992 | Russell |
| 5,153,830 A | 10/1992 | Fisher et al. |
| 5,190,024 A | 3/1993 | Senanayake |
| 5,196,966 A | 3/1993 | Yamashita |
| 5,239,354 A | 8/1993 | Russell |
| 5,430,538 A | 7/1995 | Kobayashi |
| 5,515,157 A | 5/1996 | Can |
| 5,544,254 A | 8/1996 | Hartley et al. |
| 5,572,314 A | 11/1996 | Hyman et al. |
| 5,581,346 A | 12/1996 | Sopori |
| 5,615,005 A | 3/1997 | Valente |
| 5,801,819 A | 9/1998 | Spear et al. |
| 5,828,405 A | 10/1998 | Wallner et al. |
| 5,836,205 A | 11/1998 | Meyer |
| 5,883,388 A | 3/1999 | Smith et al. |
| 5,966,673 A | 10/1999 | Shannon |
| 5,970,471 A | 10/1999 | Hill |
| 5,996,673 A | 12/1999 | Iban et al. |
| 6,014,208 A | 1/2000 | Welbourn et al. |
| 6,020,954 A | 2/2000 | Aggarwal |
| 6,211,484 B1 | 4/2001 | Anner et al. |
| 6,239,867 B1 | 5/2001 | Aggarwal |
| 6,304,853 B1 | 10/2001 | Malnekoff |
| 6,473,164 B1 | 10/2002 | De Jong et al. |
| 6,487,545 B1 | 11/2002 | Wical |
| 6,515,738 B1 | 2/2003 | Barres et al. |
| 6,684,663 B2 | 2/2004 | Kaplan et al. |
| 6,786,733 B2 | 9/2004 | Lapa et al. |
| 6,813,007 B2 | 11/2004 | Lapa et al. |
| 6,873,291 B2 | 3/2005 | Aoyama et al. |
| 6,904,410 B1 | 6/2005 | Weiss et al. |
| 6,980,283 B1 | 12/2005 | Aggarwal |
| 7,051,022 B1 | 5/2006 | Faisal |
| 7,105,822 B1 | 9/2006 | Beesley |
| 7,193,694 B2 | 3/2007 | Underwood |
| 7,239,739 B2 | 7/2007 | Lapa et al. |
| 7,251,619 B2 | 7/2007 | Holloway |
| 7,260,544 B1 | 8/2007 | Reinitz et al. |
| 7,277,161 B2 | 10/2007 | Claus |
| 7,324,188 B1 | 1/2008 | Beesley |
| 7,336,347 B2 | 2/2008 | Sasian et al. |
| 7,372,552 B2 | 5/2008 | Sasian et al. |
| 7,382,445 B2 | 6/2008 | Sasian et al. |
| 7,388,656 B2 | 6/2008 | Liu |
| 7,411,663 B2 | 8/2008 | Van de Velde et al. |
| 7,420,657 B2 | 9/2008 | Sasian et al. |
| 7,580,118 B2 | 8/2009 | Sasian et al. |
| 8,116,552 B2 | 2/2012 | Lapa et al. |
| 8,233,218 B1* | 7/2012 | Mossberg et al. ............. 63/32 |
| 8,314,989 B1* | 11/2012 | Mossberg et al. ............. 63/32 |
| 2001/0006415 A1 | 7/2001 | Tolkowsky et al. |
| 2002/0052170 A1 | 5/2002 | Holloway |
| 2002/0184916 A1 | 12/2002 | Croft |
| 2003/0112422 A1 | 6/2003 | Lapa et al. |
| 2004/0050097 A1 | 3/2004 | Eisenberg |
| 2004/0051861 A1 | 3/2004 | Bray |
| 2004/0059681 A1 | 3/2004 | Franks |
| 2004/0072137 A1 | 4/2004 | Lapa et al. |
| 2005/0036132 A1 | 2/2005 | Lapa et al. |
| 2005/0069858 A1 | 3/2005 | Lapa et al. |
| 2005/0115275 A1 | 6/2005 | Kedem et al. |
| 2005/0190356 A1 | 9/2005 | Sasian et al. |
| 2005/0190357 A1 | 9/2005 | Sasian et al. |
| 2005/0200834 A1 | 9/2005 | Sasian et al. |
| 2005/0213077 A1 | 9/2005 | Sasian et al. |
| 2005/0261989 A1 | 11/2005 | Vadon et al. |
| 2006/0092402 A1 | 5/2006 | Goto et al. |
| 2006/0164623 A1 | 7/2006 | Wagner et al. |
| 2006/0190292 A1* | 8/2006 | Reinitz et al. ............. 705/1 |
| 2006/0265288 A1 | 11/2006 | Aronson |
| 2007/0132983 A1 | 6/2007 | Van de Velde et al. |
| 2007/0222972 A1 | 9/2007 | Sasian et al. |
| 2007/0285650 A1 | 12/2007 | Kerner et al. |
| 2007/0296954 A1 | 12/2007 | Geurts |
| 2008/0055582 A1 | 3/2008 | Lapa et al. |
| 2008/0218730 A1 | 9/2008 | Sasian et al. |
| 2009/0147241 A1 | 6/2009 | Shlezinger et al. |
| 2009/0234754 A1 | 9/2009 | Lapa et al. |
| 2011/0205525 A1* | 8/2011 | Benderly et al. ............. 356/30 |
| 2011/0206234 A1* | 8/2011 | Benderly et al. ............. 356/30 |
| 2011/0228063 A1 | 9/2011 | Smith et al. |
| 2011/0299063 A1 | 12/2011 | Ninomiya et al. |

FOREIGN PATENT DOCUMENTS

| | | |
|---|---|---|
| GB | 2 358 541 A | 7/2010 |
| JP | 4065658 A | 3/1992 |
| JP | 6213818 A | 8/1994 |
| JP | 2001071665 | 3/2001 |
| JP | 2001201454 A | 7/2001 |
| WO | 96/23207 | 8/1996 |
| WO | 99/61890 | 12/1999 |
| WO | 01/36214 | 5/2001 |

OTHER PUBLICATIONS

Reinitz, et al., Modeling the Appearance of the Round Brilliant Cut Diamond: An Analysis of Fire, and More About Brillance, Gems & Gemology, Fall 2001, pp. 173-197.

GemEx Systems, Inc., What People Are Saying About the Brilliance Scope TM Technology http://www.gemex.com/consumer/quotes.html, Oct. 26, 2011.

GemEx Systems, Inc., Gemspec Imaging Spectrophotometer http://www.gemex.com (1996).

GemEx Systems, Inc., Brilliance Scope TM Viewer, Light Performance a Consumer Can See http://www.gemex.com, (2001).

GemEx Systems, Inc., The Guide Light Performance Analysis http://www.gemex.com (2002).

GemEx Systems, Inc. website http://www.gemex.com/htmdocs/consumer/the_whole_story.html, 4 pgs. Copyright 2002 GemEx Systems, Inc.

OctoNus Ltd. Russian Gemological Server, www.gemology.ru (Moscow, Russia) Sep. 22, 2001 [online], [retrieved on Aug. 21, 2007] <URL:http://web.archive.org/web/20010922105712/http://www.gemology.ru>.

Roskin, G., Diamond Notes, http:/rjck.polygon.net/archives/1999/05/jc059-048.html, May 1999, 6 pgs.

Diamond Buying: The 4 C's! Is there something missing?, http://web.archive.org/webr/http://www.gemex.com, Sep. 29, 2002, 1 pg.

Make sure you are buying the Right Diamond, http://web.archive.org/webr/http://www.gemex.com, Sep. 29, 2002, 2 pgs.

Diamond Buying: GemEx Live Report, http://web.archive.org/webr/http://www.gemex.com, Sep. 29, 2002, 2 pgs.

The eyes have it: Customers, diamond pros see the value of a BrillianceScopeni Viewer, http://web.archive.org/webr/http://www.gemex.com, Sep. 22, 2002, 4 pgs.

Gemex, Light Performance Analysis: The Science of Beauty, http://web.archive.org/webr/http://www.gemex.com, Sep. 22, 2002, 1 pg.

Diamond Buying: Beauty vs. Confusion: The GemEx Light performance Method or the 4 C's, http://web.archive.org/webr/http://www.gemex.com, Sep. 22, 2002, 2 pgs.

GemEx.Com, http://web.archive.org/webr/http://www.gemex.com, Jan. 27, 2001, 2 pgs.

GemEx.com, http://web.archive.org/webr/http://www.gemex.com, Jun. 26, 2001, 2 pgs.

GemEx Systems, Inc., "The Science of BeautyTM: How GemEx Technology Makes it Easy to Buy the Right Diamond", http://www.gemex.com/htmdocs/consumer/the_whole_story.html, 4 pgs., Copyright 2002 GemEx Systems, Inc.

(56) References Cited

OTHER PUBLICATIONS

Official Action issued in connection with U.S. Appl. No. 11/770,564 dated Apr. 28, 2010.
Official Action issued in connection with U.S. Appl. No. 11/770,564 dated Jan. 4, 2010.
Official Action issued in connection with U.S. Appl. No. 12/075,196 mailed Feb. 16, 2010.
Official Action issued in connection with U.S. Appl. No. 12/075,196 mailed May 27, 2009.
Official Action issued in connection with U.S. Appl. No. 10/918,616 mailed Mar. 1, 2012.
Official Action issued in connection with U.S. Appl. No. 10/918,616 mailed May 13, 2011.
Official Action issued in connection with U.S. Appl. No. 10/918,616 mailed Jul. 22, 2009.
Official Action issued in connection with U.S. Appl. No. 10/918,616 mailed Jan. 29, 2009.
Official Action issued in connection with U.S. Appl. No. 10/918,616 mailed Jul. 10, 2008.
Official Action issued in connection with U.S. Appl. No. 10/918,616 mailed Sep. 4, 2007.

* cited by examiner

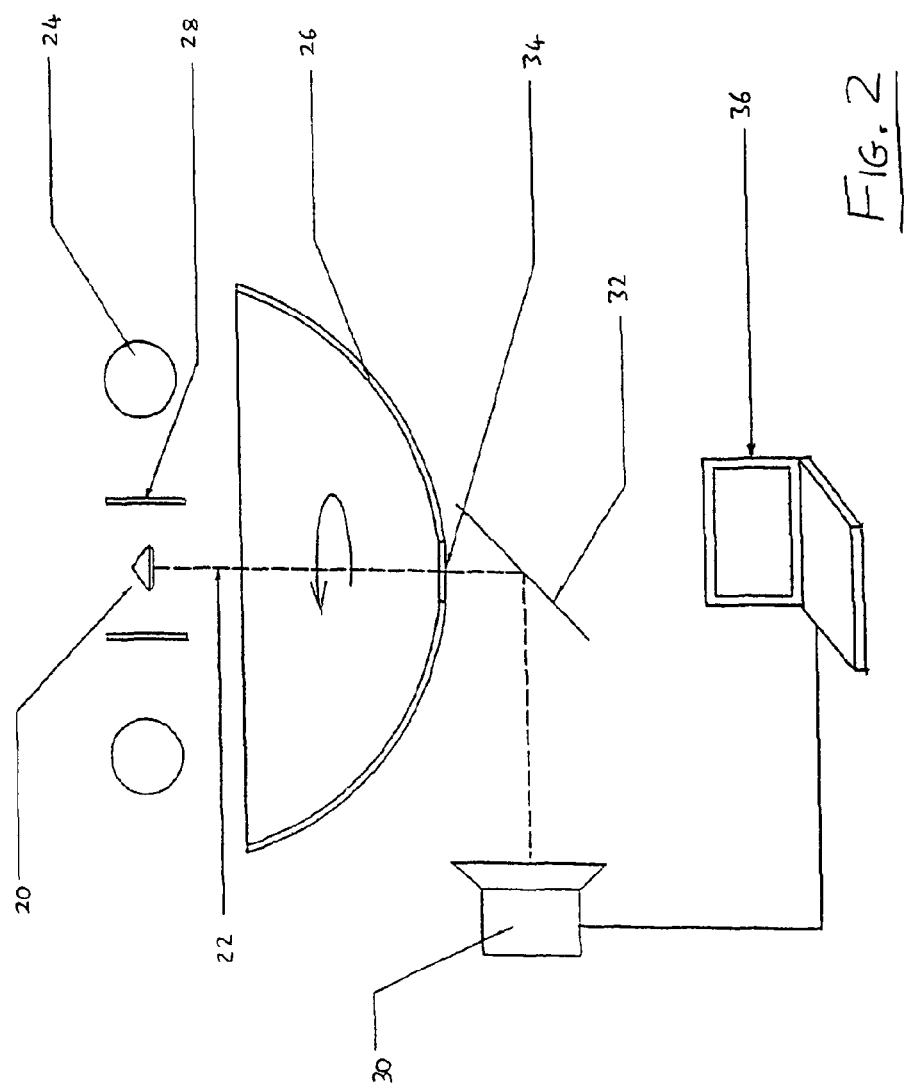

COMPUTER-IMPLEMENTED METHOD OF AND SYSTEM FOR TEACHING AN UNTRAINED OBSERVER TO EVALUATE A GEMSTONE

CROSS REFERENCE TO RELATED APPLICATION

This application is a continuation of U.S. patent application Ser. No. 10/918,616, filed Aug. 12, 2004, now U.S. Pat. No. 8,317,521 which is a continuation of U.S. patent application Ser. No. 10/272,447, filed Oct. 15, 2002, now U.S. Pat. No. 6,786,733 both of which are incorporated herein by reference in their entirety of all purposes.

FIELD OF THE INVENTION

The present invention relates to a computer-implemented method of and system for teaching an untrained observer to evaluate a gemstone such as a cut diamond. In particular, but not exclusively, the present invention relates to a computer-implemented method of and system for teaching an untrained observer to appreciate the effect of cut on the value of a gemstone, and to provide the untrained observer with an opportunity to evaluate and compare gemstones for himself or herself.

DESCRIPTION OF THE RELATED TECHNOLOGY

The beauty of a gemstone, such as a cut diamond, derives from its light handling ability. What attracts the eye is the "game of light" played by a well-cut diamond as incident light is reflected and refracted off its many facets. Diamonds and other gemstones have been cut, polished and worn as jewelry for thousands of years. They may be cut according to many different cut patterns such as the round brilliant, oval, pear, marquise, radiant, princess, heart, emerald cut etc. The most popular cut today is known as the standard round brilliant (SRB) cut as shown in FIGS. 1a and 1b.

The precursor to the modern SRB cut emerged in 1919 with Marcel Tolkowsky's seminal work entitled, "Diamond Design: A Study of the Reflection and Refraction of Light in Diamond." This work marked a breakthrough in the theoretical understanding of how cut affects light handling ability. Tolkowsky suggested certain cut proportions (i.e., the geometry) of a round brilliant diamond which should produce near optimal light performance. Today, research into the cut of a diamond is greatly advanced and techniques are being used, such as computer modeling, to study the complex optics of the SRB cut. However, the modern SRB cut bears much similarity with the round brilliant cut originally proposed by Tolkowsky.

When purchasing a gemstone, such as a cut diamond, an untrained observer typically relies on the skill and knowledge of the jeweler to explain the differences between one gemstone and another. When describing a cut diamond to an untrained observer, the jeweler may refer to what are known as the four C's—its carat weight, clarity, color, and cut. Each of these factors has an effect on the value of the diamond. Of these factors, the effect of carat weight is relatively straightforward for the untrained observer to understand—the value of a cut diamond generally increases with increasing carat weight. Similarly, the effects of clarity (clear diamonds are generally more valuable than less clear diamonds) and color (colorless diamonds are generally more valuable than colored diamonds) are relatively straightforward for the untrained observer to understand.

However, it is the cut of a diamond, and its dramatic effect on light handling ability, that has the most significant effect on value. Diamond cutting and polishing is a highly skilled art and a well-cut diamond will command a significant price premium over an otherwise identical but poorly cut diamond. In the words of one expert "cut is king!" However, given the theoretical complexity of the effect of cut on the optical performance of a gemstone, it is hardly surprising that it is the most difficult factor for a jeweler to explain to an untrained observer.

When describing the light handling abilities of cut gemstones, gemologists sometimes refer to optical properties of gemstones such as brilliance (the intensity of light returned), scintillation (fast and local fluctuations in the light returned as the gemstone moves relative to the lighting conditions), fire (the dispersion of white light into spectral colors as it refracts off the facets of the gemstone) and symmetry (the symmetry of light patterns such as the so-called "hearts and arrows" visible from the pavilion and table sides of an SRB cut diamond). However, analysis of gemstones according to these optical properties has mostly been a subjective exercise undertaken only by trained gemologists with substantial experience of examining gemstones. Untrained observers do not have the knowledge or experience to judge these optical properties for themselves. A potential purchaser, when shown a particular cut diamond under the controlled lighting conditions of a jeweler's shop, may like it or dislike it. Furthermore, he or she may subjectively prefer one diamond to another. But without training and experience, he or she will not be able to judge the light handling performance of a diamond at a level sufficient to explain the significant price premium which a well-cut diamond will command over an otherwise identical but poorly cut diamond.

Recently, electronic gemstone analyzing systems have become available which measurements of optical properties of gemstones to be taken. International Patent Publication number WO 96/23207 describes a device which captures color images of a gemstone placed in an analysis chamber and illuminated by a uniform annular light which may be moved along an axis such that the gemstone may be illuminated from a plurality of different angles. The device performs a spectral analysis of the captured images using a tunable optical band pass filter to determine the color of the gemstone. Digital images of the gemstone may also be stored, displayed or transmitted over a data network.

The website (www.gemex.com) of GemEx Systems, Inc, a US company, describes a device called the BrillianceScope Analyzer which is described as an imaging spectrophotometer. Color images of a diamond are captured in a controlled lighting environment consisting of six lighting angles, five of which provide reflected light and one of which provides diffuse lighting. These images may then be analyzed to generate a report on the diamond. The BrillianceScope Analyzer device operates on the same principle as the device described in International Patent Publication number WO 96/23207 referred to above, in that the gemstone is placed in an analysis chamber and illuminated by a uniform annular light which may be moved along an axis such that the gemstone is illuminated from different angles. The images may be analyzed by a computer, and the properties of "white light", "colored light" and "scintillation" for a diamond are determined and displayed on three line chart scales from 'low', to 'medium' to 'high'. Captured images may also be shown in a repeating sequence in one display area, giving the effect of light movement.

International Patent Publication number WO 99/61890 describes a system for the standardized grading of gemstones. A gemstone is subject to a plurality of incident light sources and images are captured for analysis. Images of the gemstone, such as a SRB cut diamond, may be captured from various viewpoints such as from the pavilion, from the crown and side-on. The gemstone is supported by a rotatable platform which is rotated when images are being captured from a side-on viewpoint to obtain profile and color images from a variety of rotational positions and to detect internal flaws and inclusions. When capturing images from above and below the gemstone, the platform is moved along an axis from a level position to a down and an up position respectively. The fixed focal length camera is also moved along an axis to focus on the gemstone when the platform is moved between the up, down and level positions. A captured image may be analyzed by a processor to obtain color measurements and measures of the brilliance and scintillation of the gemstone.

The above-described electronic gemstone analyzing systems are suited for use by trained professionals, such as gemologists or jewelers. None of the systems provides teaching enabling an untrained observer, such as a potential purchaser of a cut diamond, to understand the significance of the results of analysis.

SUMMARY OF CERTAIN INVENTIVE ASPECTS

Accordingly, certain inventive aspects relate to a system, method and computer program for teaching an untrained observer to evaluate a gemstone for himself or herself.

More particularly, one inventive aspect enables the untrained observer to understand the effect of cut on light handling ability to a sufficient level to be able to appreciate its significant effect on the value of a gemstone.

Furthermore, another inventive aspect enables the untrained observer to measure optical properties of particular gemstones and thereby judge the light handling ability of a gemstone for himself or herself.

Another aspect is to provide a system, method and computer program for enabling an untrained observer to evaluate cut gemstones which is more compact, lightweight, mechanically simpler, and therefore less expensive to manufacture, than conventional apparatus, making it more suitable for use in retail premises, such as jeweler's shops.

Yet another aspect is to provide a potential purchaser of a gemstone with an improved retail experience, thereby increasing sales.

According to one embodiment a computer-implemented method is provided that teaches a user to evaluate a gemstone, such as a cut diamond. The method includes providing a computer system connected to an apparatus capable of capturing an image of a gemstone. The computer system is arranged to process a received image of a gemstone to determine one or more optical properties of the gemstone. The method presents on a display of the computer system a series of pre-stored screens comprising a graphical representation how the cut of a gemstone affects its light handling ability, and a user interface screen. The user interface screen allows the user to control the operation of the apparatus to measure the one or more optical properties of a particular gemstone provided to the apparatus, to view an image of the gemstone measured, and to view representations of the measured one or more optical properties.

As discussed above, the effect of cut on light handling ability and thus on the value of a diamond is dramatic. However, given the theoretical complexity of the relationship between cut and optical performance, it is hardly surprising that it is the most difficult factor for a jeweler to explain to a potential purchaser of a diamond who is most likely to be untrained and inexperienced in gemology. The potential purchaser, when shown a particular cut diamond under the controlled lighting conditions of a jeweler's shop, may like it or dislike it. Furthermore, he or she may subjectively prefer one diamond to another. But, when purchasing a cut diamond, often for tens of thousands of dollars, he or she would clearly benefit from the opportunity to make a better informed purchasing decision for himself or herself. The present invention provides the potential purchaser with a deeper understanding of how cut effects light handling ability and thus how it effects the value of a gemstone. Furthermore, the present invention provides the potential purchaser with the ability to analyze gemstones in terms of measurable optical properties and thus to determine, for himself or herself, objective differences in the light handling abilities of particular cut gemstones. A deeper theoretical understanding of the effect of cut, together with the means to evaluate the light handling ability of particular cut gemstones provides the potential purchaser with the information needed to make a well-informed purchasing decision. Overall, the present invention provides a better retail experience to the potential purchaser of a gemstone, such as a cut diamond, thereby increasing customer satisfaction and sales alike.

In certain embodiments, the graphical representation of how the cut of a gemstone affects its light handling ability comprises a moving image of how incident light reflects or refracts off the facets of a cut gemstone. A graphical moving image is ideal for helping the untrained observer to understand how cut effects light handling ability.

In certain embodiments, the graphical representation of how the cut of a gemstone affects its light handling ability comprises a moving image of how incident light reflects or refracts off the facets of both an ideal cut gemstone and a non-ideal cut gemstone, whether shallow cut or deep cut. Thus, the untrained observer can visualize how the light handling ability of an ideal cut is superior to that of either a shallow or deep cut.

In certain embodiments, the series of pre-stored screens comprises a description of how the carat weight of a gemstone cut from a rough stone depends on whether the cut is ideal or non-ideal, whether shallow cut or deep cut. Thus, the untrained observer can see how obtaining the maximum carat weight from an uncut rough stone will in general be at the expense of obtaining an ideal cut, and, vice versa, how obtaining an ideal cut will in general be at the expense of obtaining the maximum carat weight from an uncut rough stone. Thus, the untrained observer will appreciate how cut may be more significant than carat weight in its effect on value.

In certain embodiments, the series of screens comprises a graphical representation of the light handling phenomenon of the SRB cut known as 'hearts and arrows'. Thus, the untrained observer is shown how a perfectly-cut SRB gemstone produces a highly symmetrical pattern of light and dark regions forming the 'hearts and arrows' and is better able to compare images of a particular gemstone against how a perfectly cut SRB gemstone would look.

In certain embodiments, the apparatus is arranged to illuminate the gemstone with a spatially varied light pattern and to capture images of the gemstone at each of a plurality of rotational positions of the light pattern relative to the gemstone, the one or more optical properties being determined in dependence on each of these images. Thus, the one or more optical properties are determined from images of the gemstone illuminated under lighting conditions that correspond to normal lighting conditions of gemstones worn in jewelry.

In certain embodiments, the light pattern is selected in dependence on a cut pattern of a standardized gemstone cut. Thus, the one or more optical properties are more accurately measured for the particular gemstone measured.

In certain embodiments, the user may view images of and representations of one or more optical properties in respect of two gemstone measured on a single screen. Thus, the user may more easily compare the light handling abilities of two particular gemstones.

In certain embodiments, the method further presents on the display of the computer system a user interface screen whereby a user may retrieve and display pre-generated reports on gemstones.

Thus, the user may use previously generated reports of gemstones for comparison or for information.

In certain embodiments, the pre-generated reports on gemstones are stored remotely to the computer system and are retrieved over a telecommunications link. Thus, the gemstone reports may be maintained and updated centrally and accessed by several different users perhaps in different jeweler's shops.

BRIEF DESCRIPTION OF THE DRAWINGS

FIG. 2 shows an apparatus for measuring optical properties of a gemstone;

FIGS. 4c-e are flow diagrams showing the process followed by the gemology teaching and gemstone evaluation application;

DETAILED DESCRIPTION OF CERTAIN INVENTIVE EMBODIMENTS

Figure 1A:
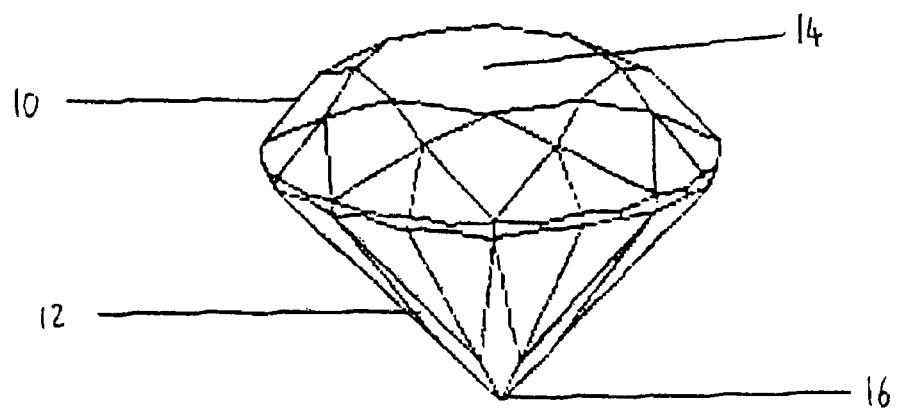
FIGS. 1a and 1b show a standard round brilliant cut diamond from an elevated side-on perspective and from a top-down view.
Figure 1B:
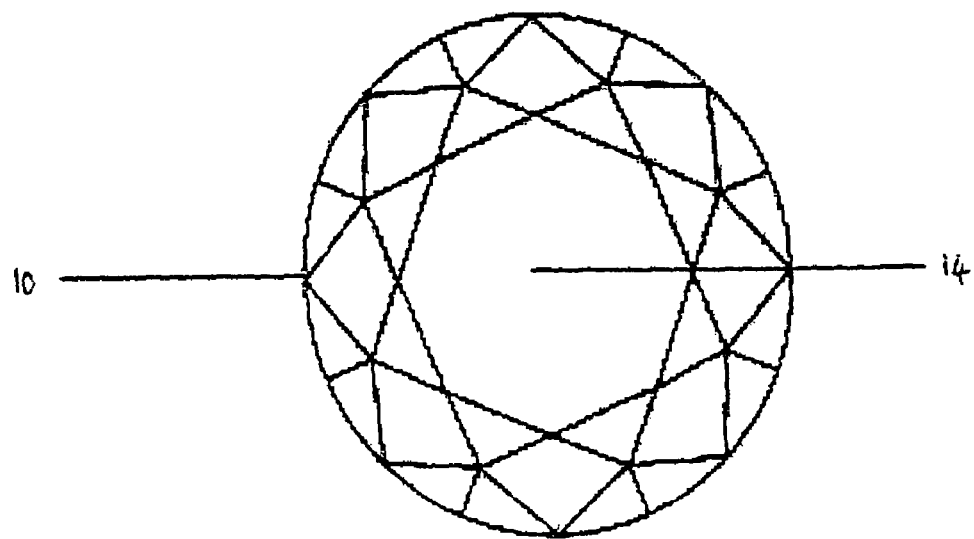

FIGS. 1a and 1b show the geometry of a standard round brilliant (SRB) diamond. FIG. 1a shows the diamond from an elevated side-on view. The top most domed-shaped portion of the diamond is known as the crown 10. The bottom most conical portion of the diamond is known as the pavilion 12. At the top of crown 10 at the center is a relatively large facet known as the table 14. The bottom most point of the pavilion 12 is known as the culet 16. FIG. 1b shows the SRB diamond from a top-down view, looking along an axis from the center of the table 14 through the culet 16. There are 32 facets on the crown 10 of the SRB cut diamond, not including table 14, and 24 facets on the pavilion, not including culet 16. It can be seen that the radial facets of the SRB cut diamond (56 in total plus one for the table and one for the culet) have an 8-fold symmetry about an axis passing though the center of table 14 and culet 16.

FIG. 2 shows a cross-sectional view of an apparatus 44 for generating data for determining optical properties of a gemstone. A gemstone such as a cut diamond 20 is placed on a platform (not shown) at an observation position with its table-side face-down. The platform is an optically clear glass plane of regular thickness arranged within the apparatus so that it is substantially horizontal when the apparatus 44 is in a horizontal position. The platform may be coated with an anti-reflection coating and provided with a small ring underneath to reduce glare. The apparatus 44 is mounted in a housing (not shown) which prevents external light from reaching the diamond 20 and dust from entering the mechanical and optical components. The housing has a access lid above the platform for placing and removing a gemstone to be measured. The inner surface of the housing and lid above the region of the platform is coated with an unreflective material so that substantially no light is reflected back from the lid or housing towards the gemstone or platform.

Diamond 20 is illuminated by an annular light 24, such as a fluorescent tube light or halogen light. Annular light 24 emits visible light of frequency comparable to daylight. A suitable annular light is a Stocker and Yale microscope illuminator with a White 5500HC. fluorescent ring light having a color temperature of 5500° K., which produces a light close to Northern daylight. Light from annular light 24 is prevented from directly reaching diamond 20 by an annular baffle 28 disposed between the annular light 24 and the diamond 20. However, light from annular light 24 is reflected off a concave surface 26 of a reflector and generally towards diamond 20. The reflector may be a semi-spherical shell centered on the observation position with the inner surface of the shell being concave surface 26.

The reflector is mounted within the apparatus 44 such that concave surface 26 is rotatable about an axis 22 perpendicular to the platform and such that when diamond 20 is placed at the observation position, the center of its table and its culet lie approximately along axis 22. Annular light 24 and annular baffle 28 are stationary and disposed within the apparatus 44 such that they are also perpendicular to and centered around axis 22. A stepper motor (not shown) is provided for rotating the reflector, and concave surface 26, about axis 22.

A viewing hole 34 is present at the bottom of the reflector and concave surface 26 where they meet axis 22. A digital camera having a charged couple device (CCD) sensor array, or a complementary metal-oxide semiconductor (CMOS) sensor array, and capable of being controlled by a personal computer (PC), is positioned within the apparatus such that it can capture an image of diamond 20 along the axis 22. The camera is a color camera having a fixed focal length, at least a 640×480 resolution, a memory capable of storing at least one image, and a data communication interface, compatible with standards such as the Universal Serial Bus (USB) (either USB 1.0 or USB 2.0), RS 422 parallel port or IEEE 1394 "Firewire" standards, for transferring captured image data to an external device, such as a PC. The camera is focused on the plane made by the topmost surface of the platform on which diamond 20 is placed, and has a suitable depth of field such that sharp images may be captured of gemstones of the largest size reasonably expected to be measured. An optically clear mirror 32 may be disposed within the apparatus so that the light path between camera 30 and diamond 20 need not be a straight line, thereby enabling a more compact format of apparatus. A suitable digital CCD camera is a Unibrain Fire-i Digital CCD color camera with a resolution of 640×480 or a Unibrain Fire-i400 Industrial version with a similar resolution. A suitable digital CMOS camera is a Silicon Imaging MegaCamera SI-3170 RGB camera, with a maximum resolution of 2056×1560, a 12-bit per pixel color depth.

The apparatus 44, including the light 24, baffle 28, reflector with concave surface 26, mirror 34, stepper motor, camera 30, and housing, but not including the PC, is compact in size (having dimensions of approximately 123 mm×112 mm×200 mm) and lightweight (approximately 3.875 kg).

Camera 30 and the stepper motor are connected to and controllable by a PC 36. By means of a suitable computer program, as will be described in greater detail below, PC 36 controls the stepper motor to rotate concave surface 26 through a series of predetermined rotational positions. PC 36 also controls camera 30 to capture images of diamond 20 at a suitable frame rate such that an image may me stored at each of the series of rotational positions of concave surface 26. The image data captured by camera 30 is transferred to PC 36 in the form of a bitmap or other suitable image file format for display and analysis. The image data is transmitted as a continual live image feed to the PC 36.

The range of angles through which concave surface 26 is rotated is dependent upon the symmetry of the light pattern reflecting off concave surface 26. With a light pattern having a 4-fold symmetry, for example, images are captured at a plurality of rotational positions as concave surface 26 is rotated through a 90° range. Within the range, the number of images captured at different rotational positions for use in analysis depends on the cut pattern of the gemstone being measured, or the cut pattern of the most faceted gemstone likely to be measured. Generally, the number of images should be at least 4 times the number of differently angled facets within the range through which concave surface 26 is rotated. Thus, with a SRB cut diamond having 32 differently angled facets in its crown and pavilion and thus 8 differently angled facets within a 90° range, at least 32 images (4*8) should be captured over the 90° range. For general purpose, it has been found that a generally suitable number of images to be captured is 45. Thus, over a 90° range, concave surface 26 is rotated in steps of 2°. It will be understood that higher or lower numbers of images may be used as appropriate to the cut pattern of the gemstone, the accuracy of measurement required and the processing capabilities of the PC 36.

Figure 3A:
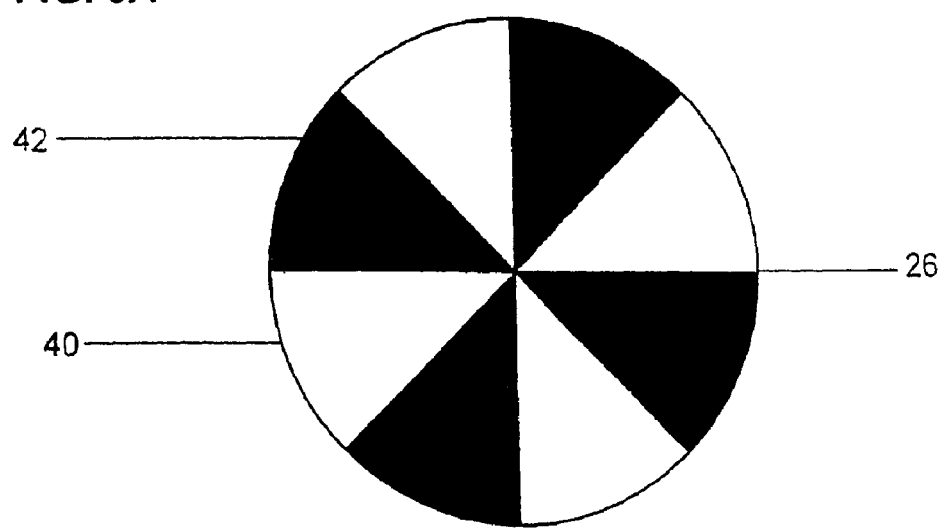
FIGS. 3a and 3b show the concave surface 26 of the apparatus of FIG. 2 having exemplary patterns of relatively reflective and relatively unreflective regions.
Figure 3B:
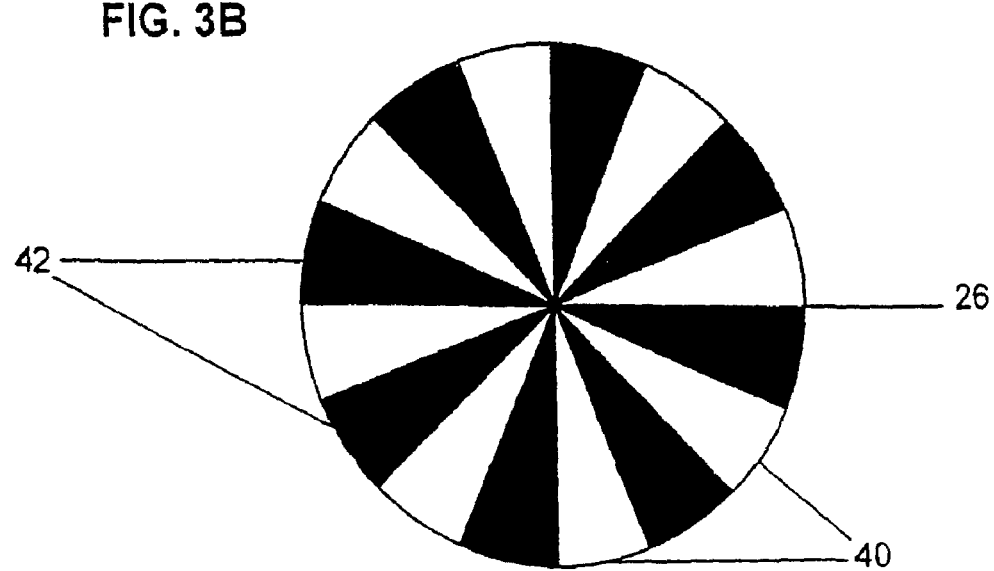

FIGS. 3a and 3b show the concave surface 26 looking down from the diamond observation position along axis 22. Concave surface 26 has a plurality of relatively reflective regions 40 and relatively unreflective regions 42 formed by coating the surface with relatively reflective and relatively unreflective materials. FIG. 3a shows one configuration of regions 40 and 42 in which concave surface 26 is divided into eight equal radial sectors, arranged around the axis 22, which are alternately relatively reflective and relatively unreflective. FIG. 3b shows a further configuration of regions 40, 42 in which concave surface 26 is divided into 16 equal sectors, arranged around the axis 22, of alternate relatively reflective and relatively unreflective regions. It can be seen that the configuration of regions 40 and 42 of FIG. 3a each have a four-fold symmetry about the axis 22 whereas the configuration of regions 40 and 42 of FIG. 3b each have an eight-fold symmetry about axis 22. Other configurations of relatively reflective regions 40 and relatively unreflective regions 42 are envisaged within the scope of the present invention. Concave surface 26 may have a matt finish.

During operation of the apparatus 44, it can be seen that the light reflecting off concave surface 26 towards the diamond 20 at its observation position has a spatially varied pattern determined by the configuration of relatively reflective regions 40 and relatively unreflective regions 42. In particular, the light pattern, as observed in the plane of the platform, will have a series of radial peaks and troughs of light intensity corresponding to the configuration. Thus, with the configuration of FIG. 3a, the light pattern will have four radial peak lines and four radial trough lines. Similarly, with the configuration of FIG. 3b, the light pattern will have 8 radial peaks and 8 radial troughs. Furthermore, with diamond 20 table-side down on the platform, the light will be reflected generally towards the crown at a broad range of angles of incidence relative to axis 22, as predominantly occurs when diamonds are mounted in rings and other jewelry for everyday use.

The selection of a particular configuration of relatively reflective regions 40 and relatively unreflective regions 42 is dependent upon the standardized cut of diamond 20. For example, a diamond of SRB cut has an eight-fold symmetry as described above, and a suitable configuration of regions 40 and 42 would be that as shown in FIG. 3a, in which there are eight sectors in total—four relatively reflective sectors 40 and four relatively unreflective sectors 42. Thus, the light pattern reflecting of concave surface 26, having four radial peaks and four radial troughs corresponds to the symmetry of the cut gemstone in that adjacent symmetrical sectors of the gemstone (of) 45° will receive corresponding radial light pattern sectors (of) 45° having adjacent peaks and troughs. As concave surface 26 is rotated through 90°, the intensity of light as observed at any radial line in the plane of the platform and about axis X, will go through a single complete cycle having a single peak and a single trough.

It will be appreciated that, with different shapes and/or symmetries of particular gemstone cut patterns, such as square, oval, pear, heart-shaped or irregular shapes, the algorithms used to determine the periphery of the gemstone and the various measurements of optical properties, as described above, may be varied to take into account the shape and symmetry of the particular gemstone cut pattern.

It will be appreciated that, with different shapes and/or symmetries of particular gemstone cut patterns, such as square, oval, pear, heart-shaped or irregular shapes, the configuration of relatively reflective regions 40 and relatively unreflective regions of concave surface 26, may be varied to take into account the shape and symmetry of the particular gemstone cut pattern. It will also be appreciated that the configuration of relatively reflective regions 40 and relatively unreflective regions of concave surface 26 may be varied to take into account a particular property being determined. For instance, when determining a measure of the fire of a gemstone, it is desirable to for relatively reflective regions 40 to be thin radial lines arranged around the axis 22, such that the light pattern reflected comprises relatively narrow peaks and relatively wide troughs. Thus, spectrally colored light will be generally less overpowered by white light and more visible.

It will be appreciated that in alternative embodiments, concave surface 26 may be held stationary within the apparatus and the platform is rotated instead. In this arrangement, the images captured of diamond 20 rotate and extra processing is required to take that into account when analyzing those images. When comparing a first image at a first rotational position with a second image at a second different rotational position (and with subsequent third, fourth . . . images) processing must be performed so that pixels of the first and second (and subsequent) images correspond to the same region or regions of diamond 20. To achieve this, the second (and subsequent) image may be digitally rotated back about the point corresponding to the center of rotation of the platform to correct for the rotation of diamond 20 in the images. Alternatively, when comparing selected pixels of a first and second (or subsequent) image, to obtain a measure of scintillation for example, the pixels of the second (or subsequent) image may be selected so as to correspond to a portion of the image rotated back about the point corresponding to the center of rotation of the platform to correct for the rotation of diamond 20. However, due to limitations on the resolution of the captured images, accuracy of comparison is reduced in both cases and this arrangement is less preferable than the former arrangement in which the platform is stationary and concave surface 26 rotated.

It will be appreciated that in further alternative embodiments, concave surface 26 may be held stationary within the apparatus, and instead the camera 30 and the platform both rotated by a single or separate stepper motors in a coordinated fashion. This arrangement eliminates the need for extra processing to correct for the rotation of the images of diamond 20, but involves additional mechanical complexity and increased cost of manufacture.

While the above embodiment has described an apparatus arranged to i) support a gemstone having an axis of symmetry such that the axis of symmetry is parallel to the axis 22, ii) rotate the light pattern relative to the platform about the axis 22, and iii) capture images of the gemstone along the axis 22, it is contemplated that the present invention is not limited to this particular arrangement of the three axes, although this arrangement is generally preferred. In particular, the axis of relative rotation between the light pattern and the platform need not be co-linear or even parallel to the axis 22 (i.e., from the axis parallel to an axis of symmetry of a gemstone when supported in the apparatus) and/or the axis along which the images are captured need not be co-linear or even parallel to the axis 22. Furthermore, the axis of relative rotation between the light pattern and the platform and the axis along which the images are captured need not be co-linear or even parallel between themselves.

What is important is that a gemstone having an axis of symmetry may be supported in the apparatus such that the axis of symmetry, the axis of relative rotation between the light pattern and the means of support, and the axis along which the images are captured are coordinated such that i) the apparatus is able to take advantage of the shape and/or symmetry of the cut pattern of the particular gemstone when rotating the light pattern relative to the gemstone, and ii) the apparatus is able to capture images of the gemstone, such as images of the crown of a SRB cut diamond, from which features resulting from the shape and/or symmetry of the gemstone may be observed. For instance, the axis of relative rotation between the light pattern and the means of support may be at an angle of incidence to the axis of symmetry of up to about 30° without serious degradation to the performance of the apparatus. Similarly, the axis along which the images are captured may at an angle of incidence to the axis of symmetry of up to about 45° without serious degradation to the performance of the apparatus.

Figure 4A:
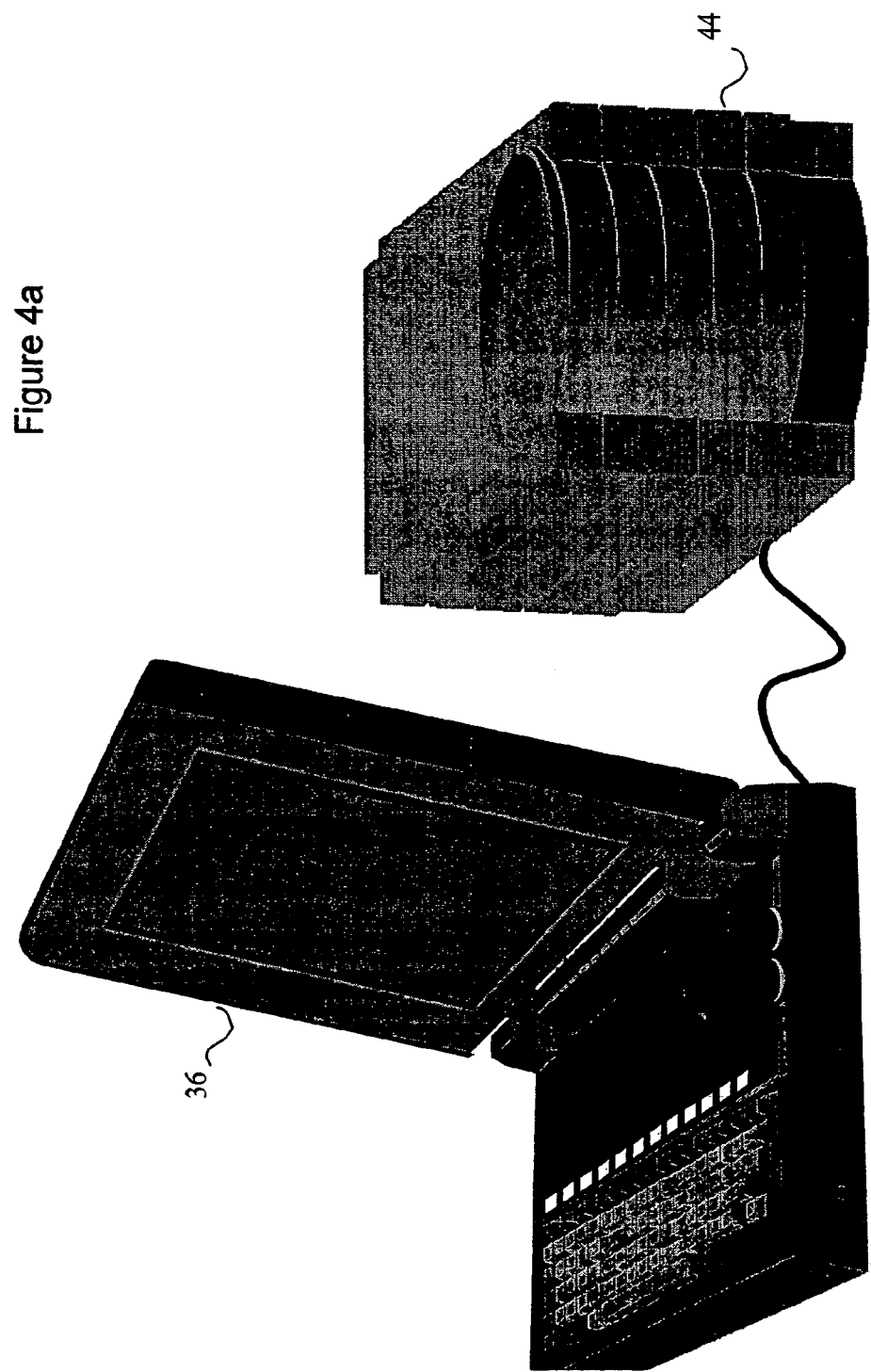
FIG. 4a shows the measuring apparatus of FIG. 2 connected to a laptop computer as would be suitable for placement in retail premises such as in jeweler's shops.

FIG. 4a shows the apparatus 44 for generating data for determining optical properties of a gemstone connected to PC 36, a laptop or notebook PC, as would be suitable for placement in retail premises such as in a jeweler's shop. PC 36 has an Intel Pentium III or IV central processing unit (CPU), at least 128 megabytes of memory, at least a 10 gigabyte hard disk drive, and an LCD panel screen of at least 1024×768 resolution supported by a 2D video processing chipset capable of displaying at a color depth of at least 16 bits (preferably 24 bit depth) in a resolution of 1024×768. It has a sound processing chipset and speakers, a keyboard and a pointing device, such as a mouse or touch pad. PC 36 also has one or more of a USB 1.0 or 2.0 port, a parallel port and an IEEE 1394 "Firewire" port for connecting to the camera for frame grabbing and for controlling the stepper motor of apparatus 44.

Figure 4B:
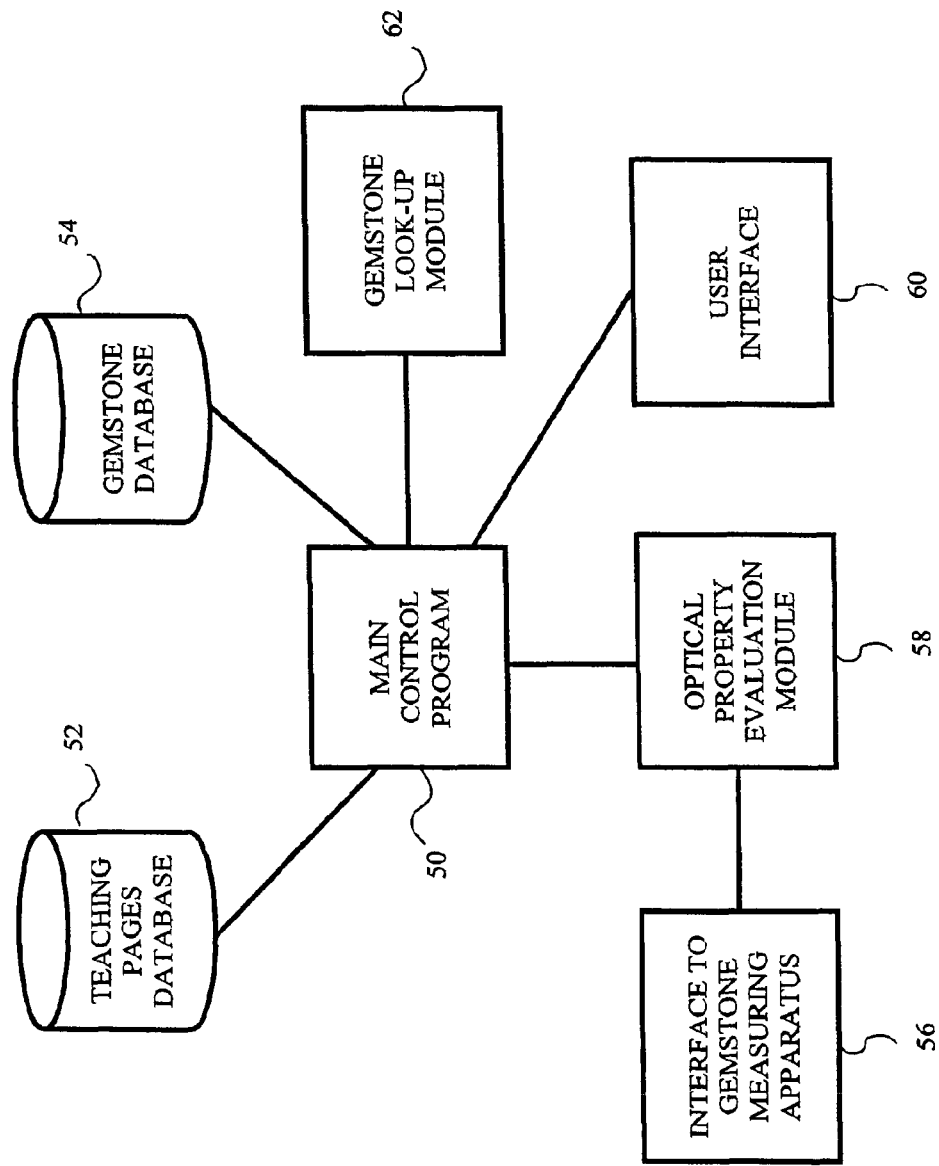
FIG. 4b is a schematic diagram showing the logical components of the gemology teaching and gemstone evaluation application.

FIG. 4b is a schematic diagram showing logical components of the gemology teaching gemstone evaluation application. PC 36 runs a standard operating system, such as Microsoft Windows XP or the like. A main control program 50, running over the operating system, controls the presentation of gemology teaching pages (stored in database 52) and gemstone reports (stored in database 54) for gemstones identified by gemstone code (using gemstone look-up module 62). Main control program 50 is also capable of launching, as a sub program, optical property evaluation module 58 which controls the operation of and receives data from apparatus 44 (via interface 56—which drives for the ports connected to the apparatus) for determining optical properties of a gemstone. Gemology teaching pages, gemstone reports and the user interface screens for operating the apparatus and showing the results of evaluation are all presented via user interface 60 which drives the display, sound system, keyboard, pointing device and other user input/output devices.

Main control program 50 has a Web-like front end and is composed of a plurality of locally stored hyperlinked Hypertext Markup Language (HTML) pages viewed using a Web browser application such as Microsoft Internet Explorer. The HTML pages are hyperlinked so as to form a menu structure through which the user may navigate when using the gemology teaching and gemstone evaluation application. Preferably, the HTML pages comprise embedded Macromedia Flash presentations and the Web browser is capable of displaying those Macromedia Flash presentations by launching a Macromedia Flash player application also resident on PC 36. Gemology teaching pages (together with the main menu page and gemstone report viewing pages) are stored on a hard disk drive of PC 36 and are indexed by filename to form database 52. Main control program 50 is capable of receiving user input from a user of PC 36 via user interface 60, such as a user clicking on a hyperlink or allowing the pointing device to hover over a hotspot, to control the presentation of gemology teaching pages, to look-up gemstone reports using gemstone look-up module 62, or to launch the optical property evaluation module 58.

FIG. 4c is a flow diagram showing the process followed by main control program 50. The process starts at step 64 when the main control program 50 is first launched. At step 66, the main menu page is displayed (see FIG. 5). At step 68, user input is received via user interface 60. At step 70, it is determined whether the user has selected to use the optical property evaluation module 58. If so, the process continues to A at FIG. 4d. If not, the process continues to step 72, where it is determined whether the user has selected to look-up a gemstone from gemstone database 54 using gemstone look-up module 62. If so, the process continues to B at FIG. 4e. If not, the process continues to step 74, where it is determined whether the user has selected a particular gemology teaching page to display from teaching pages database 52. If so, the process continues to step 76 where the appropriate page is displayed (see FIGS. 6 to 9 generally). The process then returns to step 68 where user input is received via user interface 60. If not, the process returns to step 68 directly.

Optical property evaluation module 58 controls the operation of apparatus 44. It is also arranged to receive data generated by apparatus 44 and to analyze it and display the results using user interface 60. Optical property evaluation module 58 is written in Visual Basic and is called as a sub-program from main control program 50. It is arranged to control the stepper motor to rotate concave surface 26 and to control camera 30 to capture and transfer to PC 36 images of diamond 20 at each of the predetermined rotational positions, for example, 45 images taken at rotational steps of 2° over a total range of 90°. Control over the stepper motor is achieved by using a conventional stepper motor control circuit, such as a Motorola MC 3479 stepper motor controller, to interface between PC 36 and the stepper motor. Apparatus interface 56 on PC 36 comprises program elements for sending digital control signals to the stepper motor control circuit. Control over camera 30 is achieved using the camera's inbuilt control interface. Apparatus interface 56 on PC 36 comprises program elements for sending digital control signals to camera 30.

Apparatus interface 56 on PC 36 is under control of optical property evaluation module 58 which is itself under control of user interface 60. Thus the user is able to send instructions via user interface module 60 to cause a series of images of a gemstone to be captured and transferred from camera 30 to PC 36, to analyze the images using various algorithms to obtain measurements of optical properties of the gemstone, and to display the images and representations of the optical properties on the screen of the PC 36.

FIG. 4d is a flow diagram showing the process followed by optical property evaluation module 58. Note that the module is arranged to wait for user input (by clicking of either the "Scan" or "Calibrate" buttons as appropriate—see FIGS. 10a-j) between each of the steps 78, 80, 82 and 84 shown in FIG. 4d. At step 78, the gemstone evaluation screen is displayed (see FIG. 10a). At step 80, the apparatus is calibrated by taking an image of a known portion of concave surface 26 and measuring the intensity of light at three areas of the image (see FIGS. 10a and 10b). At step 82, a live image as captured by camera 30 is displayed allowing the user to place a diamond table-side down on the platform of apparatus 44. At step 84, the circumference of the diamond and its orientation about the axis of symmetry is determined. At step 86, the stepper motor is controlled to rotate concave surface 26 through a plurality of rotational positions and images are captured and stored on the hard disk of PC 36 for each position. At step 88 the brilliance, scintillation and symmetry of the diamond are determined using algorithms to be described in detail below, as well as an overall score out of ten. Finally, at step 90, the captured images are displayed in sequence to produce a moving image of the diamond, and representations of the determined optical properties of brilliance, scintillation and symmetry are displayed as bar charts, together with overall score out of ten for the diamond.

To calculate the three measures of brilliance, scintillation and symmetry, from the stored images, three separate algorithms are used. In each case, optical property evaluation module 58 first analyses the images to determine the circumference of the gemstone and its center point. The circumference is determined by first summing the light intensity levels at each pixel over all the images at different rotational positions, for example 45 images, to obtain a composite image. Then, all pixels of the composite image having a light intensity level above a predetermined threshold (representing a light level slightly above the level of the black background) are selected. Then the smallest circle containing all the selected pixels is determined and this is defined as the circumference of the gemstone.

Once the circumference and center of the gemstone are determined, the three algorithms are executed to calculate measurements of the three optical properties only in respect of pixels contained within the circumference and excluding pixels outside the circumference.

To calculate a measure of the brilliance of the gemstone, the average light intensity level (i.e., brightness) is determined over each pixel within the circumference of the gemstone and for each of the stored images at different rotational positions. Thus, if there are n pixels in the circumference of the gemstone, and 45 images at different rotational positions, the light intensity level is averaged over 45*n pixels in total. This results in an average light intensity level for the gemstone over all images at different rotational positions, which provides an objective measure of the brilliance of the gemstone.

To calculate a measure of the scintillation of the gemstone, the difference in light intensity levels (i.e., brightness) between a pixel from a first image (captured at a first rotational position) and its corresponding pixel (at the same coordinate position) from a second image (captured at a second rotational position, one rotational step after the first rotational position) is determined. This is repeated for all pixels within the circumference of the gemstone in the first and second images, and for all pairs of first and second images captured at rotational positions which are one rotational step apart. Thus, if there are n pixels in the circumference of the gemstone, and 45 images at different rotational positions, 44*n differences are calculated. The number of times the absolute difference in light intensity levels is greater than a predetermined threshold is counted for all pixels in the circumference and for all pairs of images which are one rotational step apart. The ratio of this number over the total number of pixel pairs, 44*n, gives an objective measure of the scintillation of the gemstone.

To calculate a measure of the symmetry of the gemstone, for the composite image, composed of the stored images at each of the different rotational positions, pixels within the circumference of the gemstone are divided into 8 approximately equal radial sectors about the center of the gemstone. The number of sectors is chosen to correspond to the 8-fold symmetry of the SRB cut pattern. Thus, if there are n pixels within the circumference of the gemstone in an image, each sector has approximately n/8 pixels. Then, the difference in light intensity levels (i.e., brightness) between each pixel in each of the 8 sectors of an image and its corresponding pixels (i.e., the corresponding pixels as rotated by i×45°, where i=1 to 7) in the seven other sectors of the same image is determined. Thus (7+6+5+4+3+2+1)*n/8 =7*n/2 differences are calculated. The average of the absolute values of these differences is then calculated to give an objective measure of the symmetry of the gemstone.

In alternative embodiments of the present invention a measure of the fire of the gemstone may be calculated by using an algorithm similar to that for determining scintillation. However, instead of measuring the difference in light intensity levels, the difference in the relative proportions of color components (i.e., red, green, and blue (RGB)) between a pixel from a first image (captured at a first rotational position) and its corresponding pixel (at the same coordinate position) from a second image (captured at a second rotational position, one rotational step after the first rotational position) are determined. This is repeated for all pixels within the circumference of the gemstone in the first and second images, and for all pairs of first and second images captured at rotational positions which are one rotational step apart. For each pixel pair, the number of times the absolute difference in the relative proportions of any of the three color components is greater than a predetermined threshold is counted for all pixels in the circumference and for all pairs of images which are one rotational step apart. The ratio of this number over the total number of pixel pairs gives an objective measure of the fire of the gemstone.

Gemstone look-up module 62 is for viewing previously generated reports on gemstones identified by a unique and secure gemstone code. Gemstone look-up module 62 is implemented as a Java applet associated with corresponding user interface pages. The Java applet is programmed to receive an entered code comprising a sequence of alphanumeric characters and to search database 54 for a file with the matching code. Database 54 may comprise a plurality of gemstone report files indexed by filename (i.e., by the gemstone code). Alternatively, database 54 may be implemented using a specific database application such as Microsoft Access, with a field of each database entry being the gemstone code. All codes are of a fixed length such that the code system is sufficient to uniquely identify many millions of gemstones, whereas database 54 is, in practice, likely to store gemstone reports for only thousands of gemstones. The codes for each diamond are chosen at random thus implementing security in that it is statistically unlikely to be able to guess a valid code for a gemstone. Preferably, the gemstone data is also kept secure on PC 36 by being encrypted, either within the Windows XP file system or within the specific database application (if used), or both.

FIG. 4e is a flow diagram showing the process followed by main control program 50 from point B. At step 92, a gemstone report look-up page is displayed. At step 94, the gemstone look-up module 62 Java applet receives a gemstone code input by the user. At step 96, the gemstone look-up module 62 checks gemstone report database 54. At step 98, it is determined whether a gemstone report for the gemstone corresponding to the input gemstone code exists in gemstone report database 54. If yes, the process continues to step 100, where the gemstone report is displayed. If not, the process continues to step 102, where an error message is displayed.

In alternative embodiments of the present invention, either or both of databases 52 and 54 may be stored remotely to PC 36 and accessed over a telecommunications link, such as over an Internet connection to a central server. Thus, a plurality of PCs running the gemology teaching and gemstone evaluation application, perhaps in different jeweler's shops, may each be connected to a central server storing either or both of databases 52 and 54. Thus, updates to the gemology teaching pages stored in database 52 and updates to the gemstone reports stored in database 54 may be performed centrally. Preferably, the central server and telecommunications link use encryption to secure the gemstone report data being stored or transmitted.

The present invention is perhaps best understood with reference to screen shots of the display of PC 36 during use, as will now be described. It will be appreciated that the actual screens displayed on PC 36 are full color and that the presentation to a user is superior than can be reproduced in these black and white diagrams. Furthermore, the screen shots provided here are in respect of a gemology teaching and gemstone evaluation application designed for SRB cut diamonds. It will be appreciated that the gemology teaching and gemstone evaluation application may be designed for other gemstone cut patterns and for other gemstones.

Figure 5:
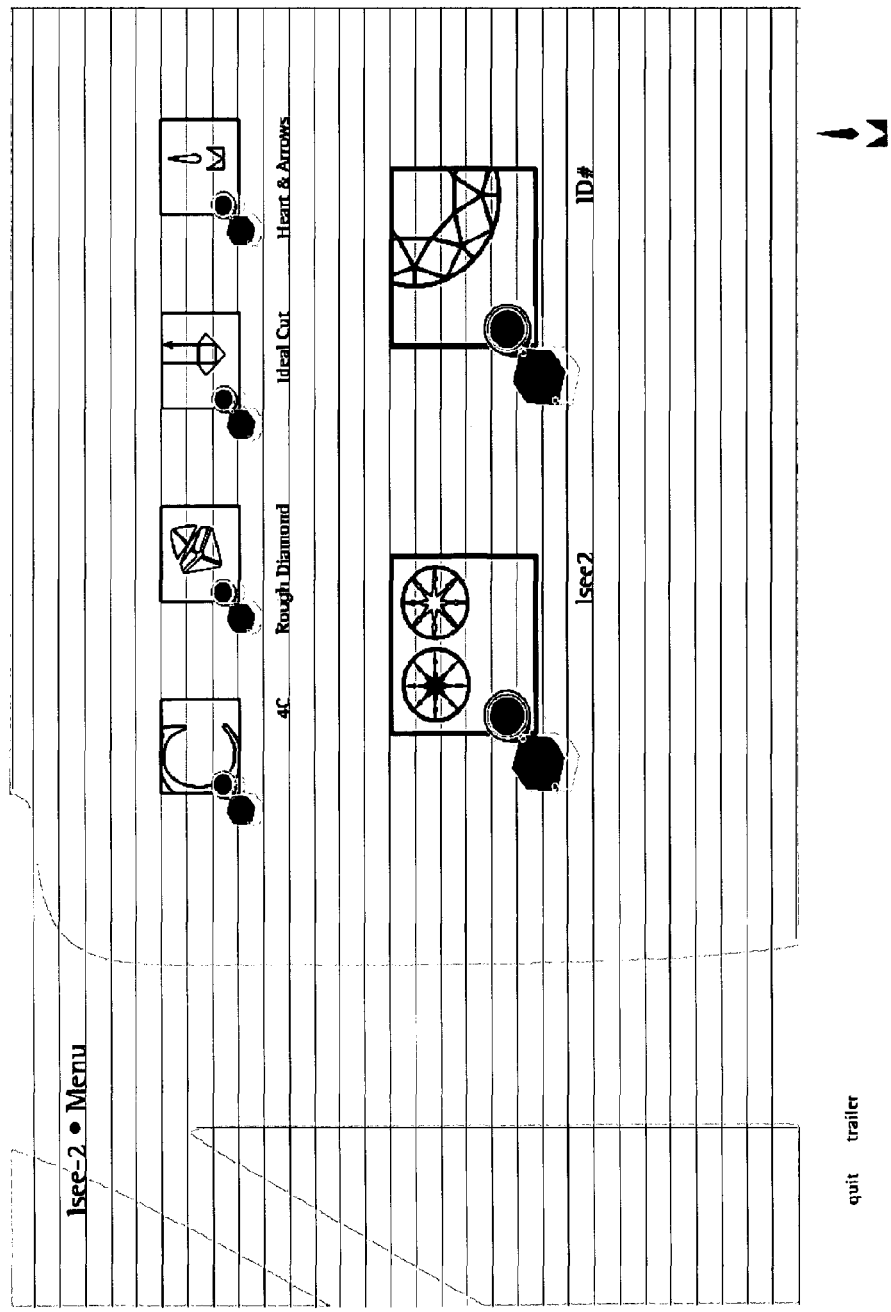
FIG. 5 is a screenshot of the main menu page of the gemology teaching and gemstone evaluation application.

FIG. 5 shows the main menu screen presented to a user of the gemology teaching and gemstone evaluation application of the present intention. Four small icons are displayed for selecting different gemology teaching pages, namely: the 4 C's, rough diamond, ideal cut, hearts and arrows. Beneath, 2 larger icons are displayed for selecting the optical property evaluation module (on the left) or the gemstone report look-up module (on the right). The user may click on any of these icons to activate a hyperlink to the corresponding gemology teaching page, or module.

Figure 6A:
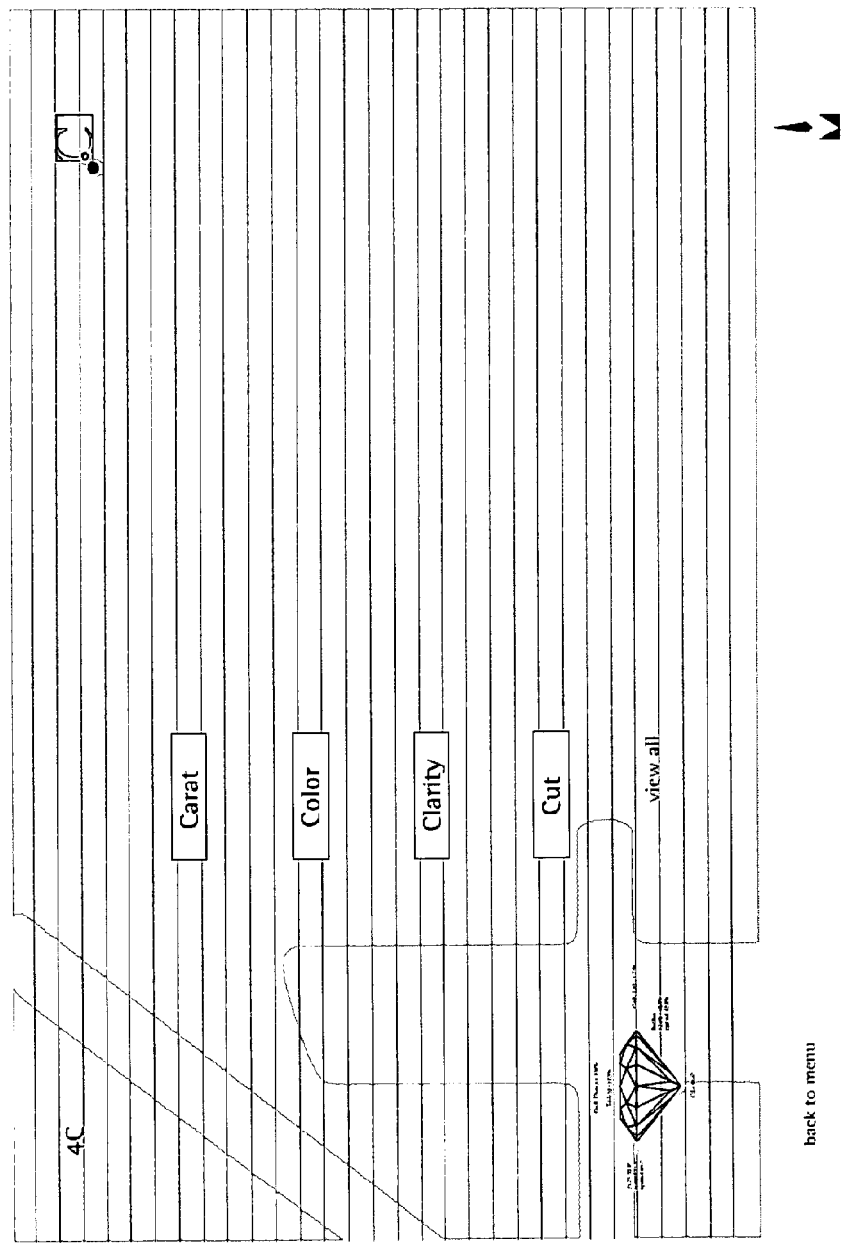
FIGS. 6a-g are screenshots of the pages, of the gemology teaching and gemstone evaluation application explaining the four 'C's of diamonds and the geometry or proportions of a modem SRB cut diamond.
Figure 6B:
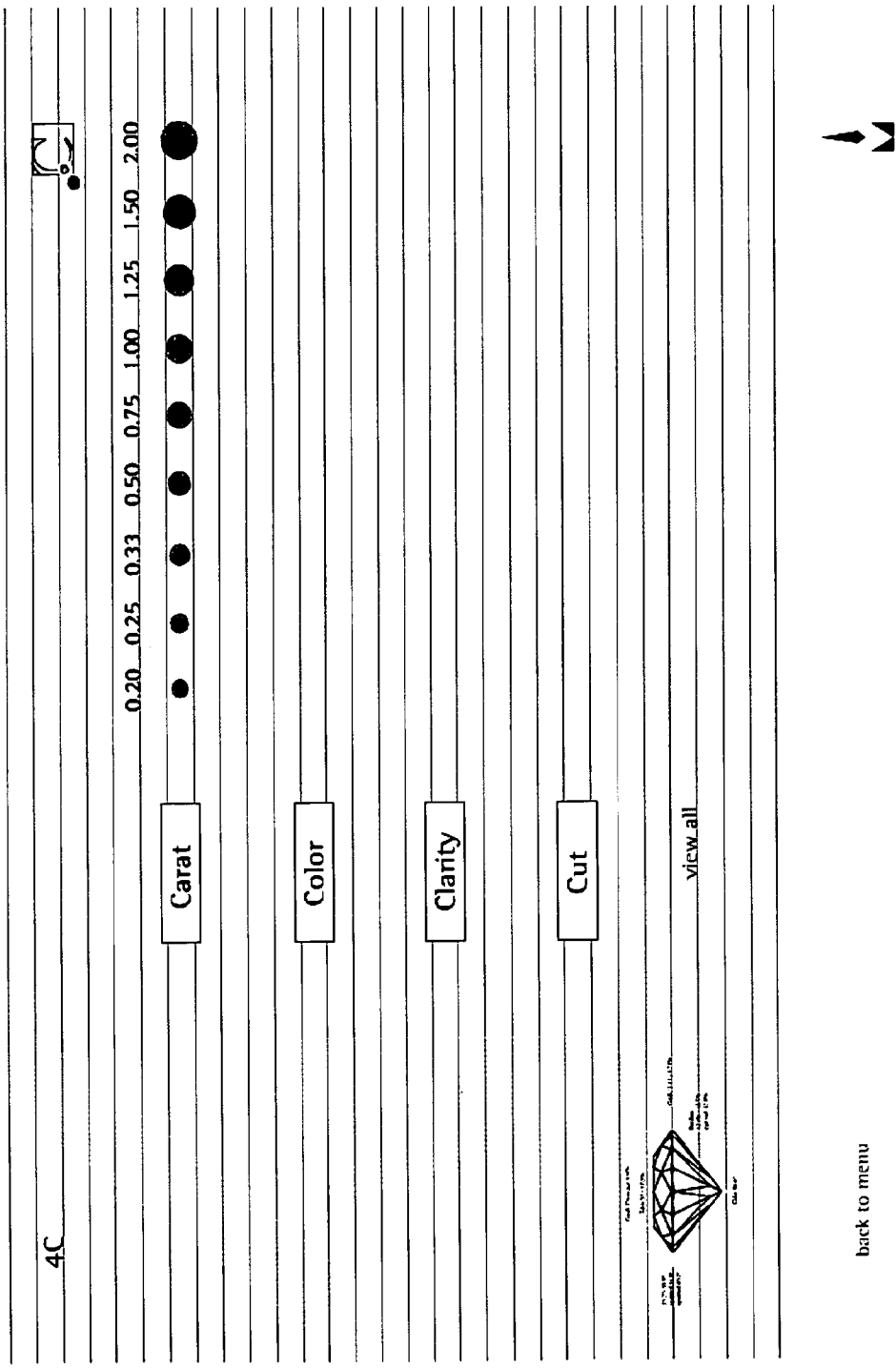
Figure 6C:
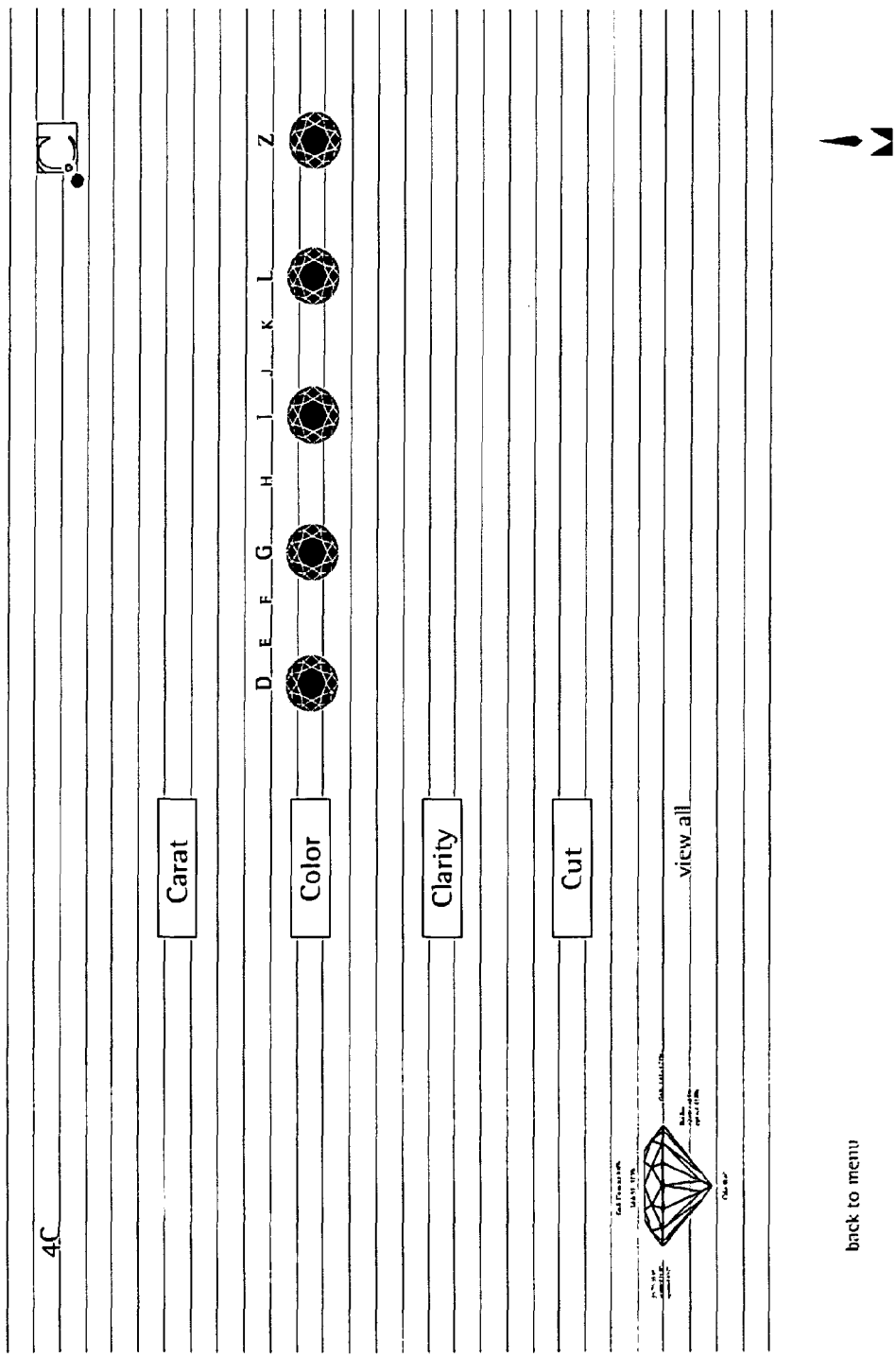
Figure 6D:
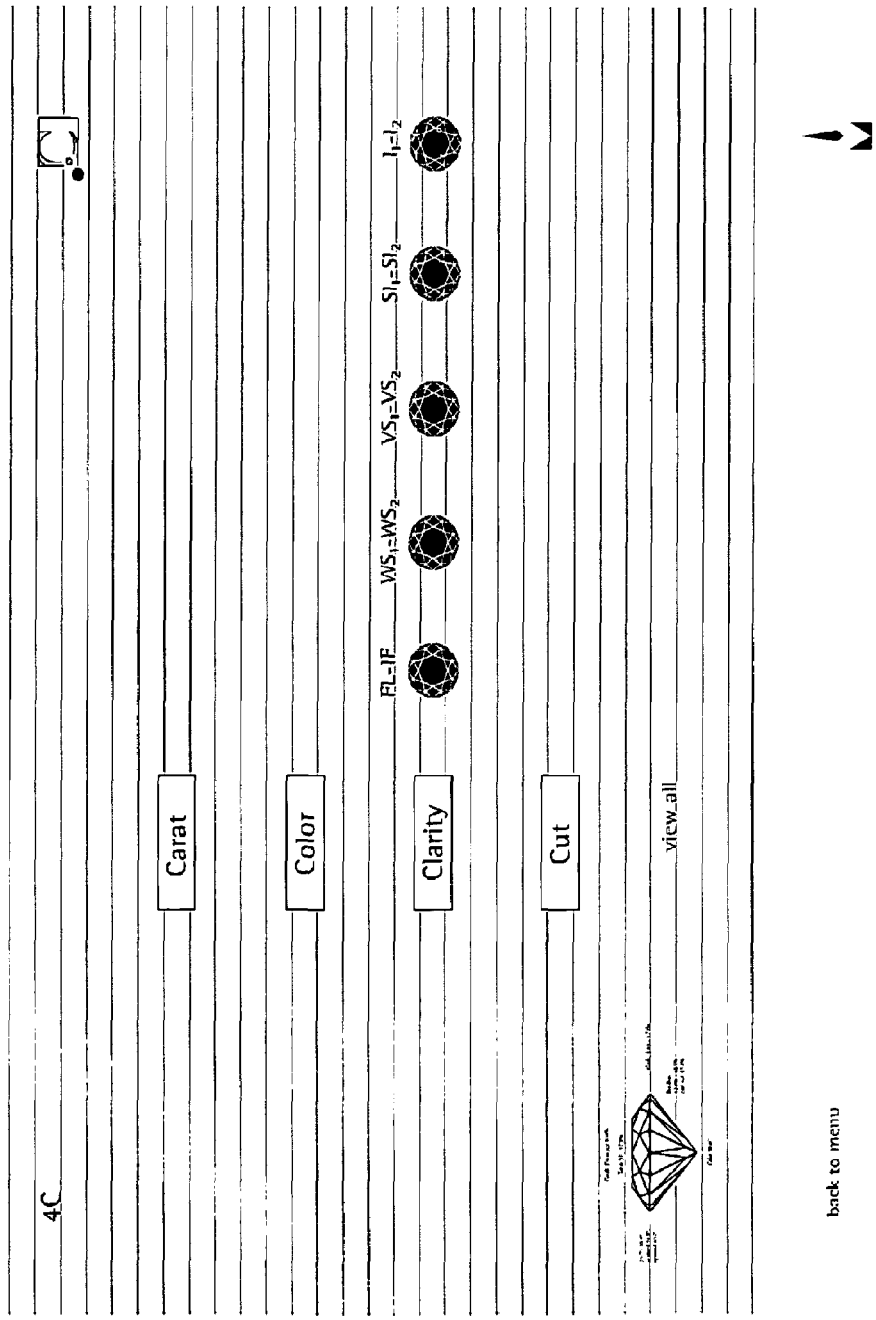
Figure 6E:
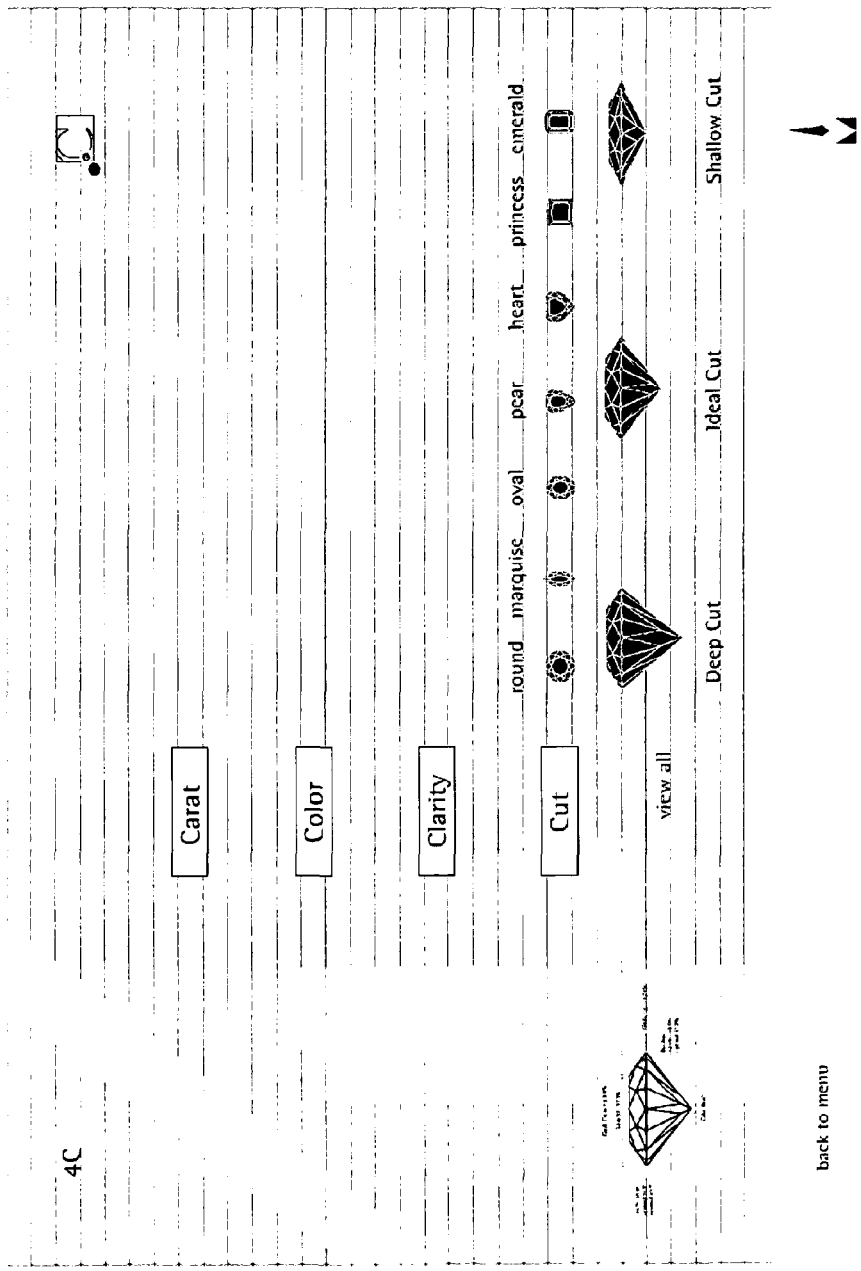

FIGS. 6a-g show the 4 C's gemology teaching pages. Four boxes are displayed containing the four C's, namely, Carat, Color, Clarity and Cut. When the user selects a particular one of the 4 C's, by allowing the pointer, controlled by the pointing device, to hover over any of the four boxes, an appropriate graphic representation explaining the property is displayed to the right of the selected box. FIGS. 6b-e show the four corresponding screens. In FIG. 6b, representations of cut diamonds are displayed from the table-side, showing diamonds of various carat weights from 0.20 carats to 2.00 carats. In FIG. 6c, representations of cut diamonds are displayed with different colors from grade D (relatively colorless) to grade Z (highly colored). In FIG. 6d, representations of cut diamonds are displayed showing various degrees of clarity from internally flawless (FL-IF) to flawed (I1-I2). In FIG. 6e, representations of diamonds cut according to various standard cut patterns are displayed, namely: round, marquise, oval, pear, heart, princess, and emerald. Also, underneath, three SRB cut diamonds are displayed, a deep cut (a built-up stone with the culet making a relatively acute angle); an ideal cut (a perfectly cut stone with the culet making an angle of about 98.6°; and a shallow cut (a flat stone with the culet making a relatively obtuse angle). The different optical characteristics of these three SRB cut diamonds are explained in further gemology teaching pages described below.

Figure 6F:
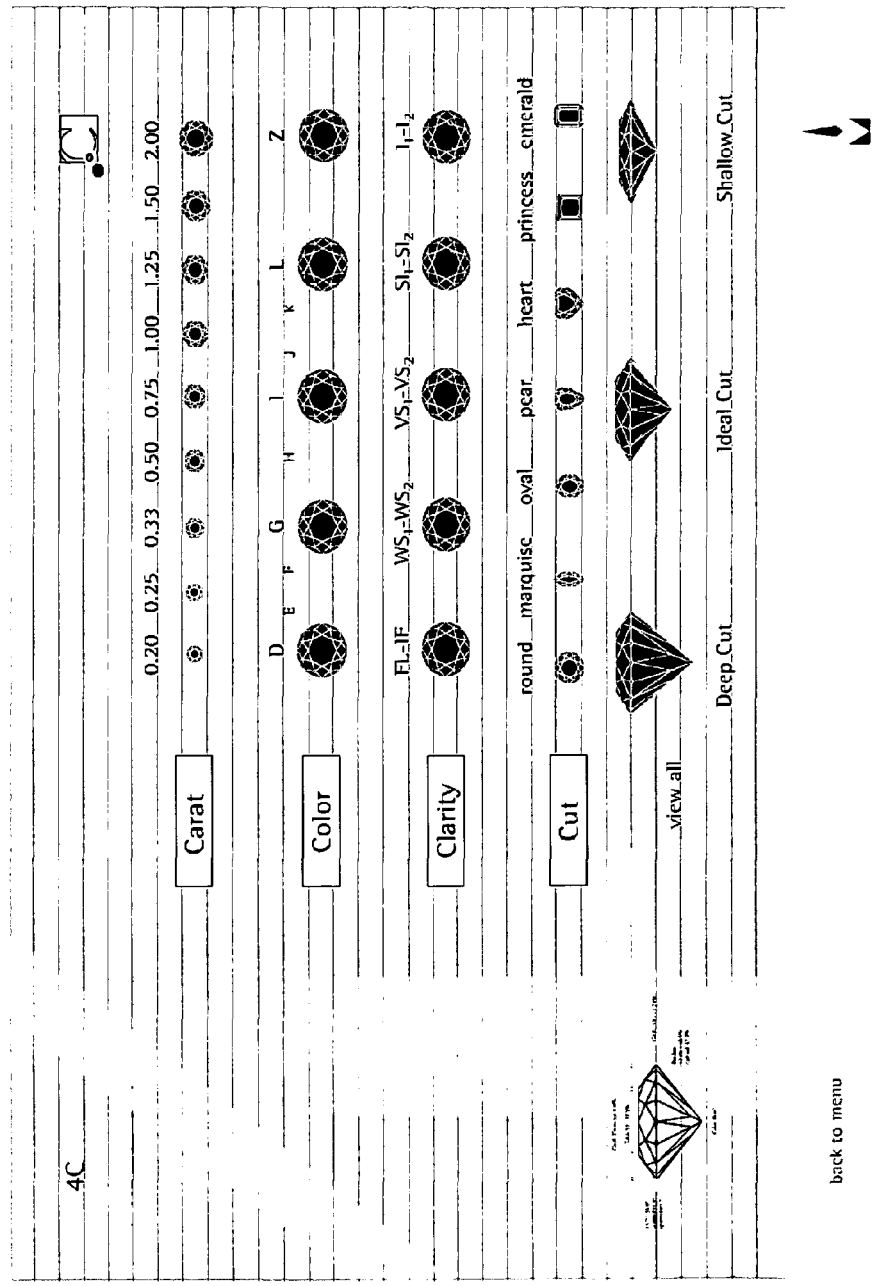
Figure 6G:
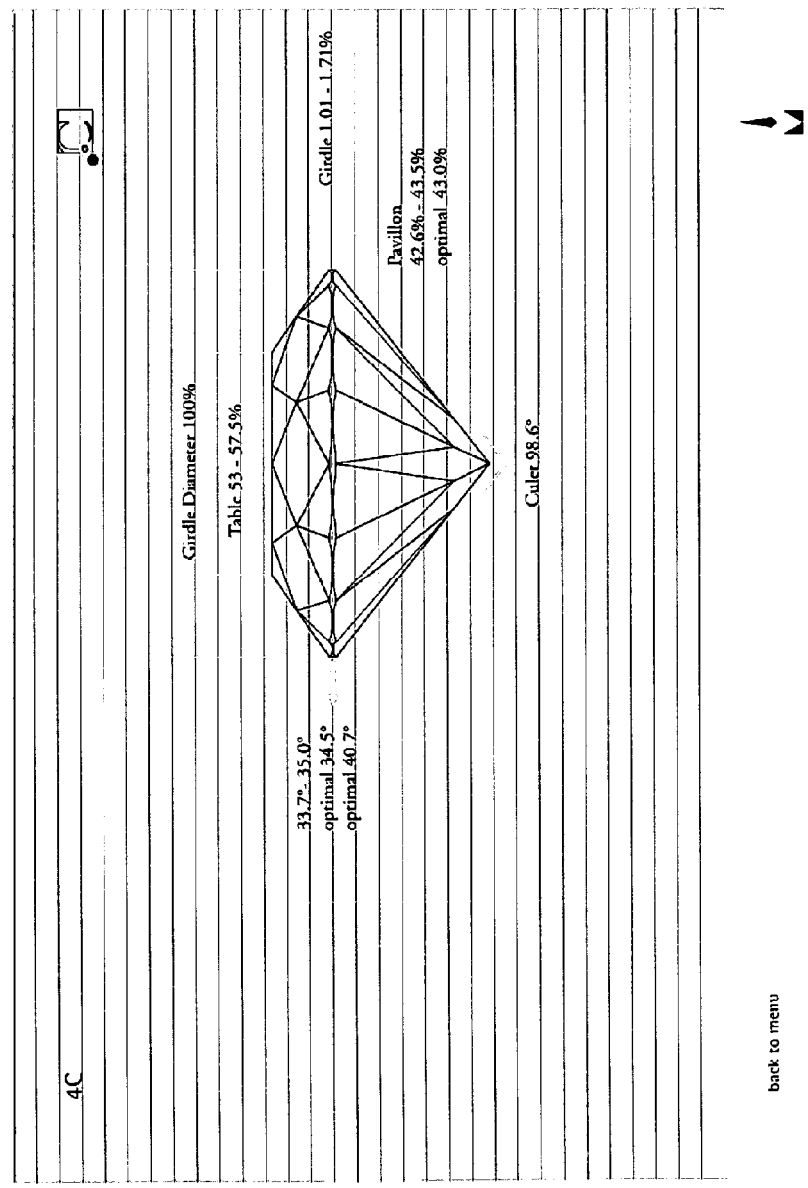

Beneath the four boxes is the text "view all" which may be selected, by allowing the pointer to hover over it, to display all the representations of the 4 C's together as shown in FIG. 6f. In the lower left hand corner of the screen is a small icon showing a side-on image of a SRB cut diamond which may be selected, by clicking on it, to display an image, as shown in FIG. 6g, of the optimal cut proportions of an ideal cut SRB diamond in terms of the girdle diameter to table diameter ratio (53-57.5%), the girdle width to diameter ratio (1.01-1.71%), the crown-pavilion angle (33.7°-35.0°, the pavilion height to girdle diameter ratio (42.6%-43.5) and the culet angle of about 98.6° depending on the other angles. It should be noted that the small icon showing a side-on image of a SRB cut diamond is shown in each gemology teaching page and may be selected from any gemology teaching page to show the optimal cut proportions of an ideal cut SRB as showed in FIG. 6g.

Figure 7A:
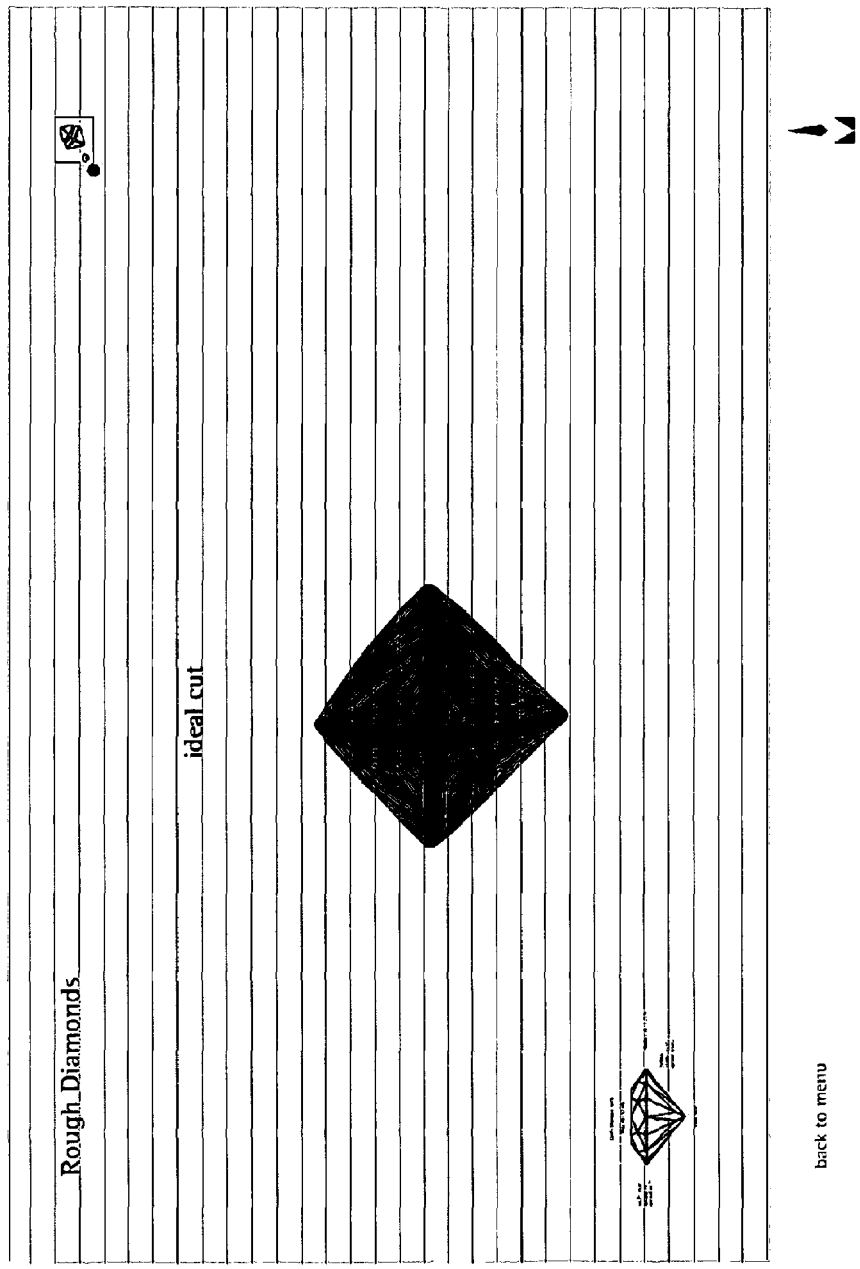
FIGS. 7a-h are screenshots of the pages, of the gemology teaching and gemstone evaluation application showing the difference between shallow, deep and ideal SRB cut diamonds in terms of the process of cutting a rough diamond and carat weight.
Figure 7B:
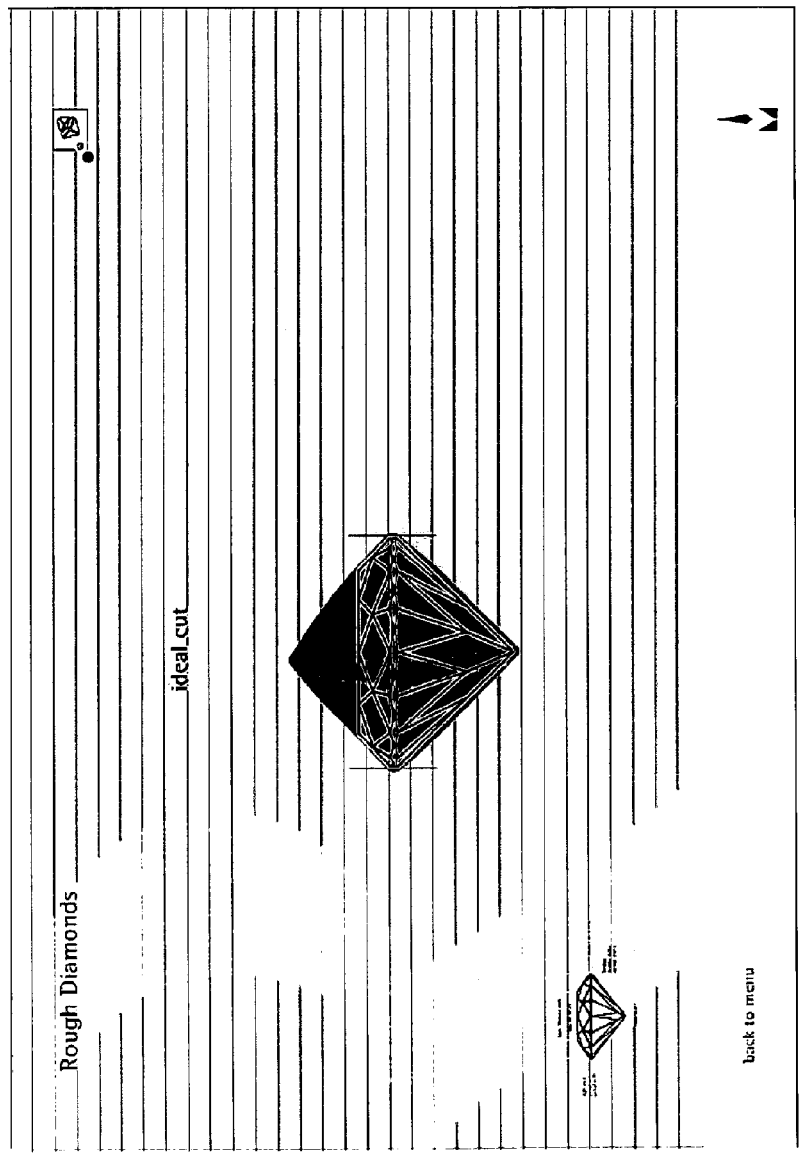
Figure 7C:
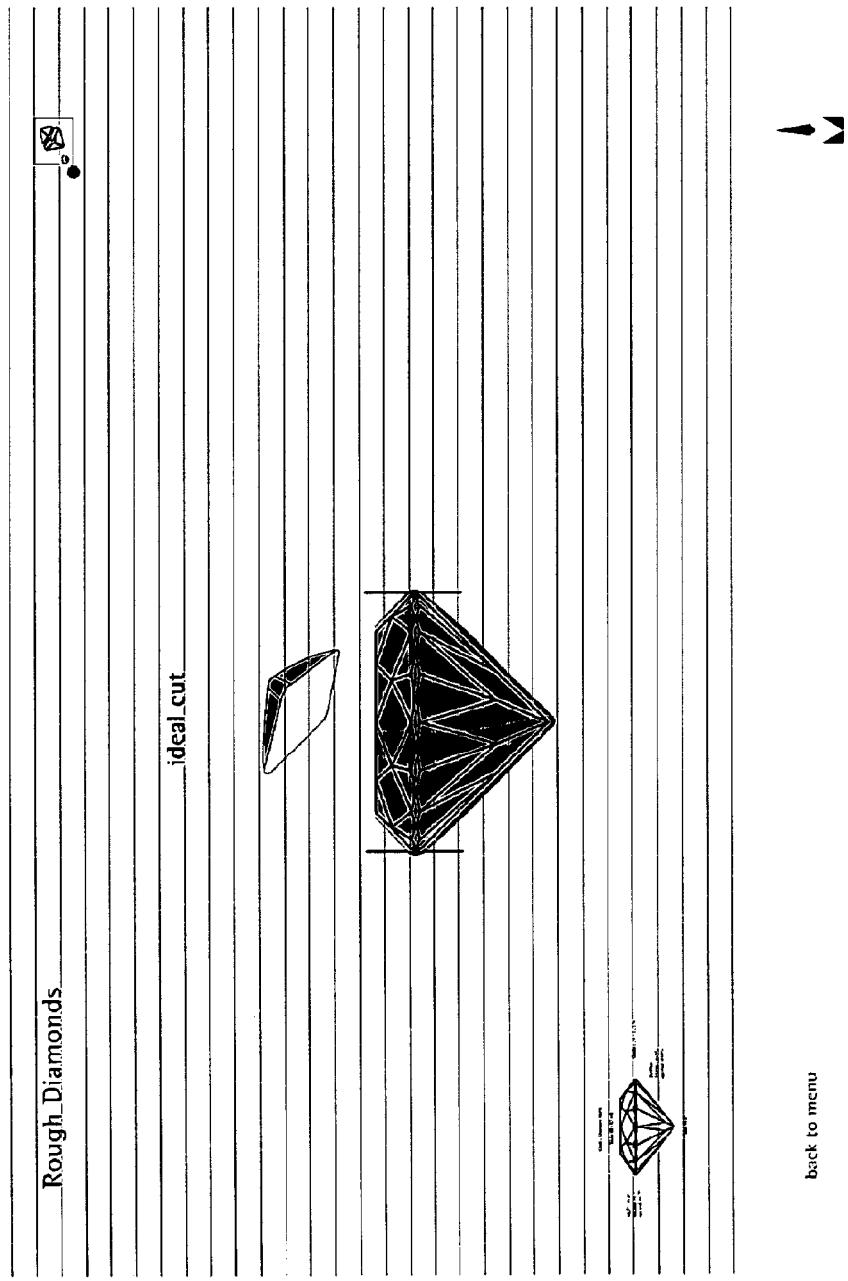
Figure 7D:
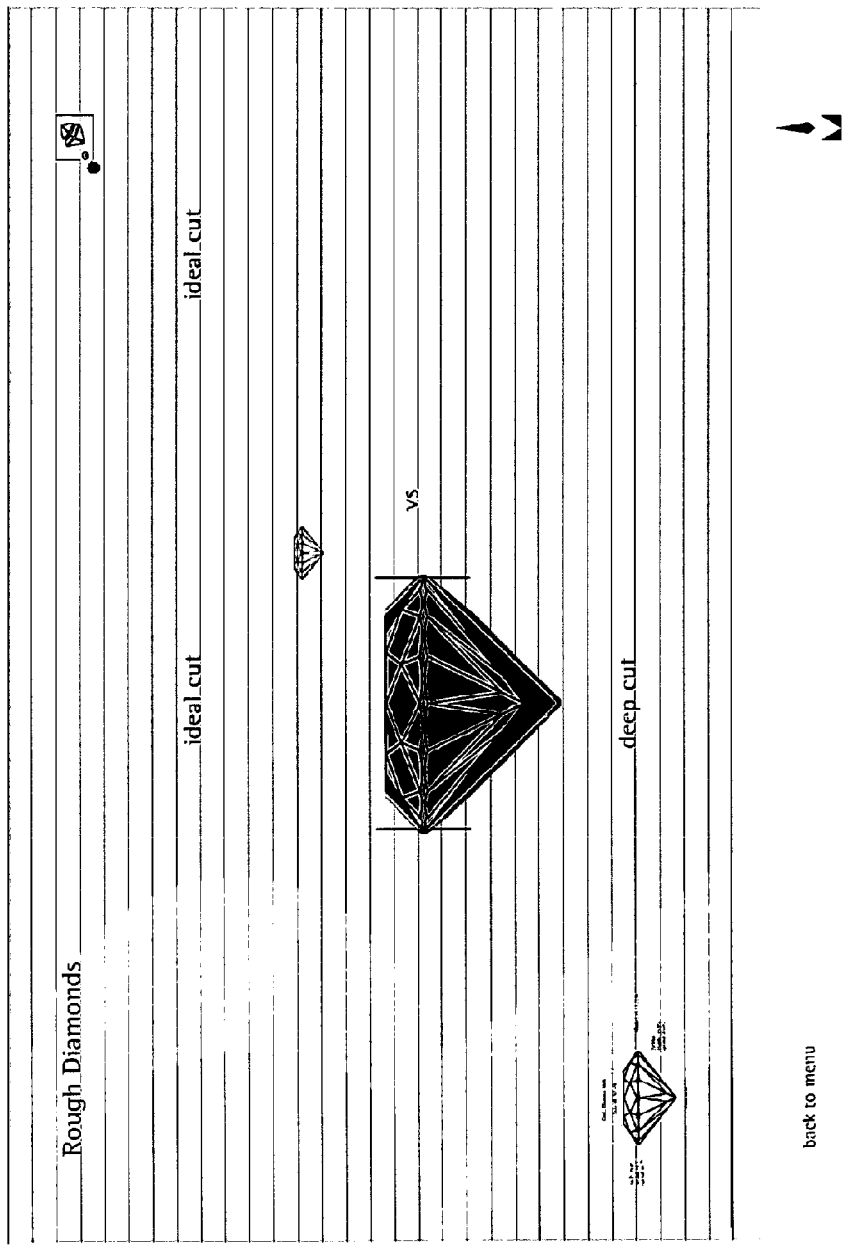

FIGS. 7a-h show gemology teaching pages showing the difference between shallow, deep and ideal SRB cut diamonds in terms of the process of cutting a rough diamond and in terms of the carat weight that can be obtained. The Figures show exemplary screenshots taken at various points during a moving image presentation executed using Macromedia Flash components. FIG. 7a shows a first rough ready to be cut. FIG. 7b shows the rough with the shape of an SRB cut, the biggest possible within the limitations of the rough, overlayed on it. Note, that this is not an ideal SRB cut, but, in this case, a deep SRB cut which fits best within the shape of the rough and thus maximizes the carat weight obtainable. FIG. 7c shows the rough with the excess stone cut away from above the table. The excess may be used to cut a smaller SRB cut diamond. FIG. 7d shows the cut rough with the shape of an ideal SRB cut, the biggest possible within the limitations of both the rough and the ideal SRB cut proportions, overlayed on top of the shape of the deep cut. Note the excess stone that would need to be cut away to produce and ideal cut rather than the deep cut. Because of its shape and positioning, this excess stone must be cut away in pieces and is less suitable or possibly not suitable at all for cutting smaller SRB cut diamonds.

Figure 7E:
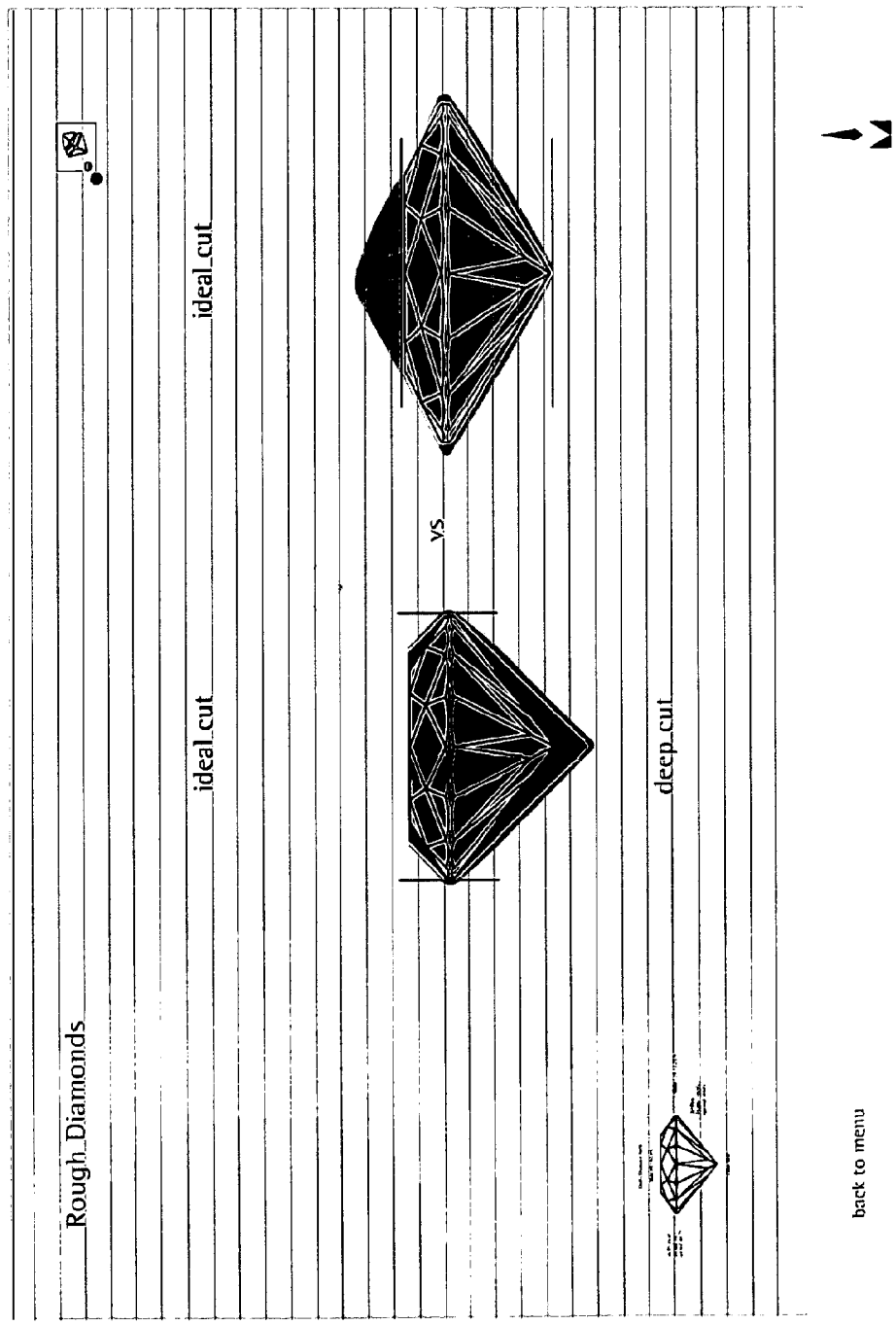
Figure 7F:
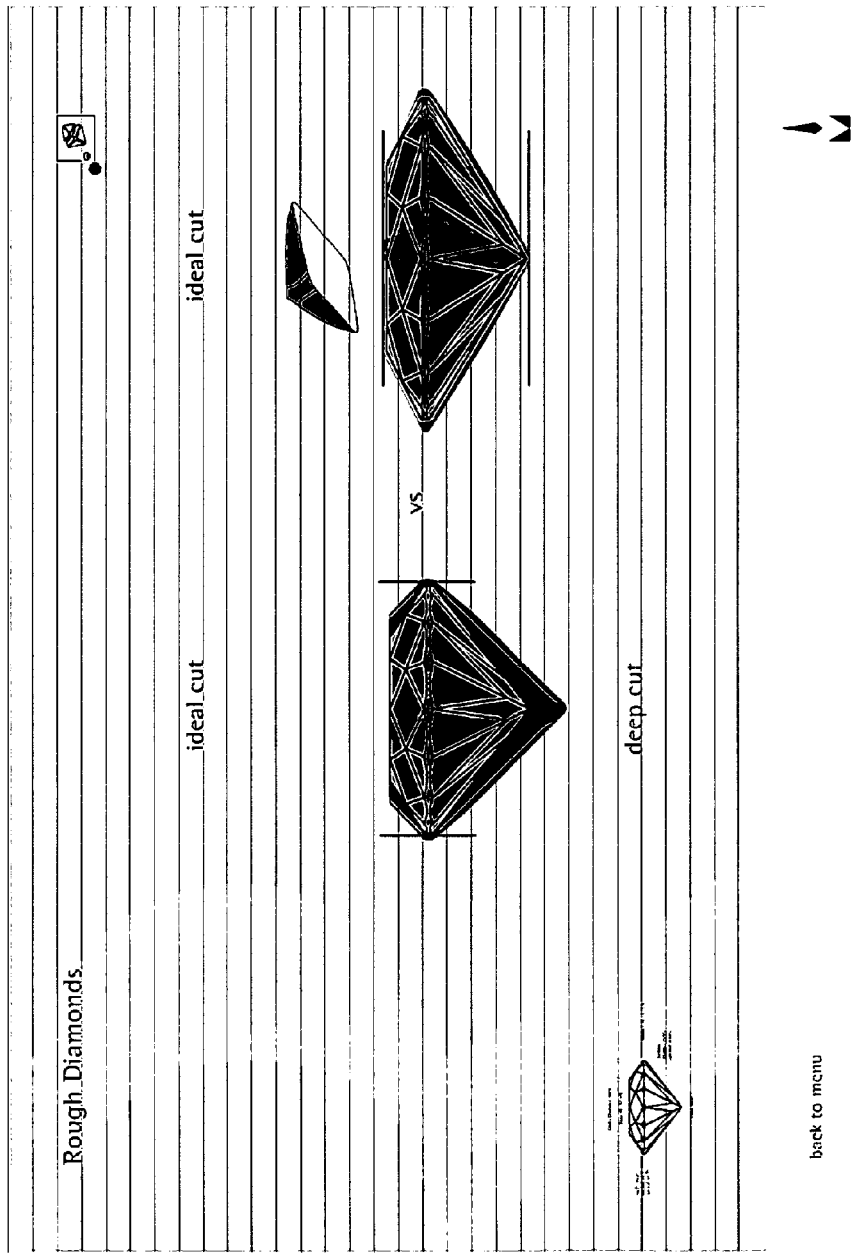
Figure 7G:
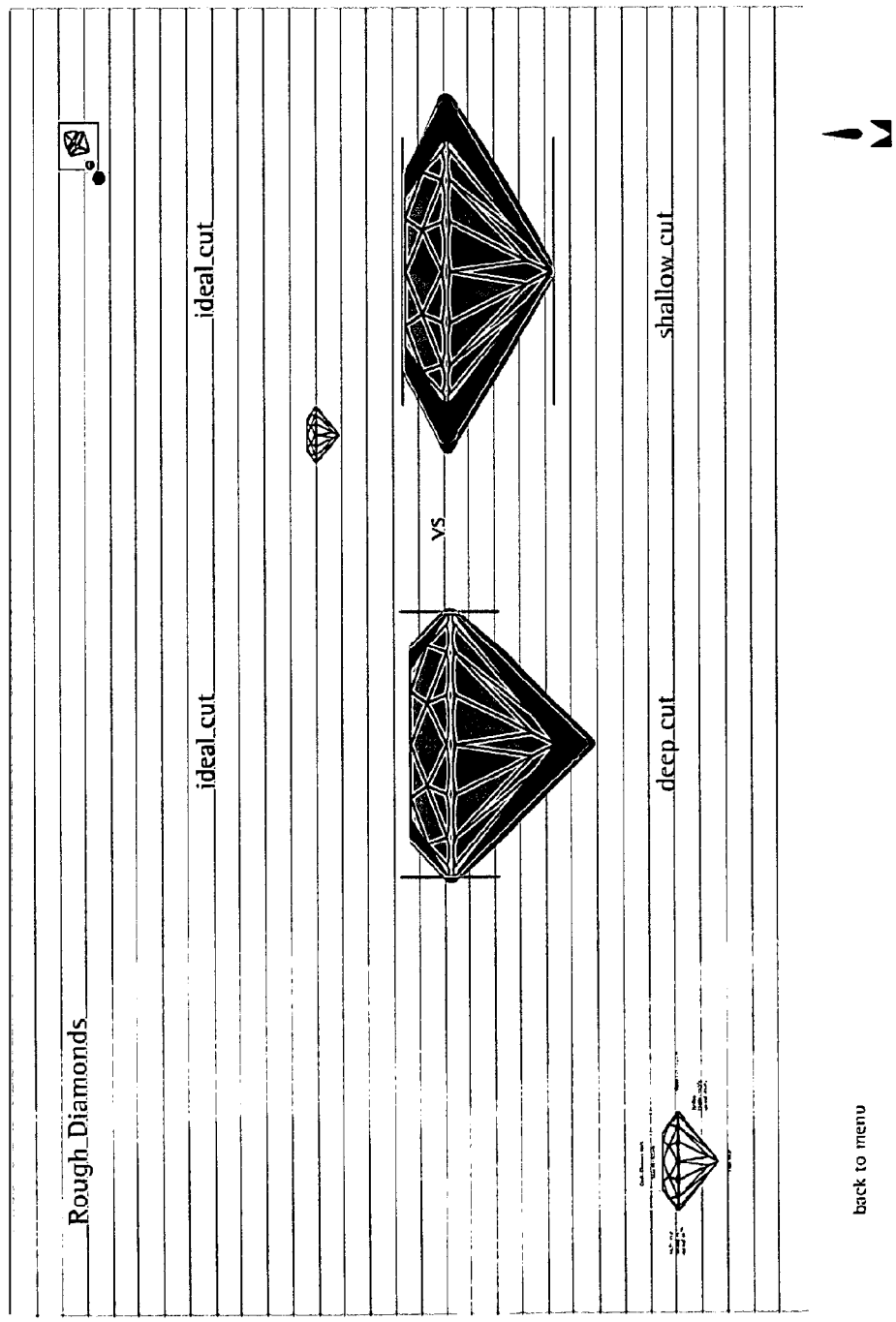
Figure 7H:
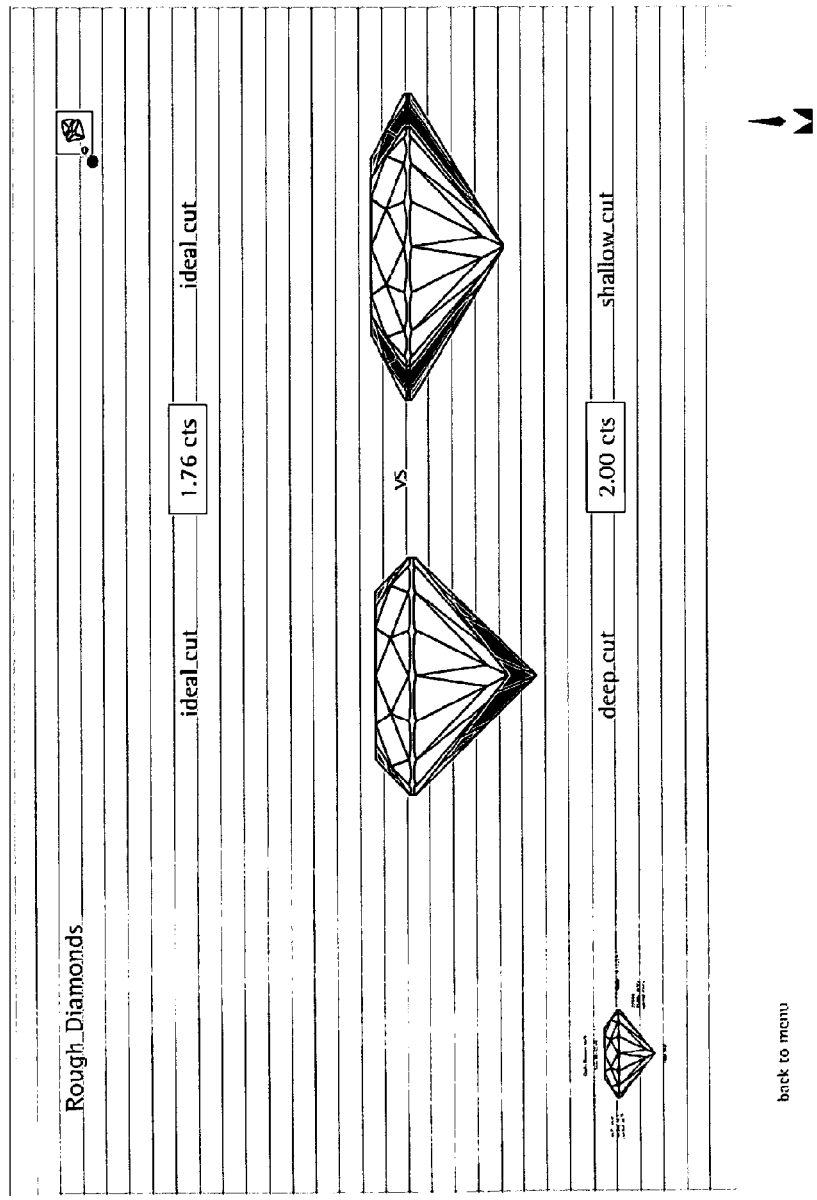

FIG. 7e now shows a second rough ready to be cut in addition to the first rough described above. Again, the shape of an SRB cut, the biggest possible within the limitations of the rough, is overlayed on it. Note, that this is not an ideal SRB cut, but, in this case, a shallow SRB cut which fits best within the shape of the rough and thus maximizes the carat weight obtainable. FIG. 7f shows the second rough with the excess stone cut away from above the table. Again, the excess may be used to cut a smaller SRB cut diamond. FIG. 7g shows the cut rough with the shape of an ideal SRB cut, the biggest possible within the limitations of both the second rough and the ideal SRB cut proportions, overlayed on top of the shape of the shallow cut. Again, note the excess stone that would need to be cut away to produce and ideal cut rather than the shallow cut. Again, because of its shape and positioning, this excess stone must be cut away in pieces and is less suitable or possibly not suitable at all for cutting smaller SRB cut diamonds. FIG. 7h shows the first and second roughs with the excess stone above the table cut away and with both the deep and shallow SRB cuts and the ideal cuts overlayed. Also shown are exemplary carat weights for the ideal cuts (1.76) compared with the deep and shallow cuts (2.00). Thus, the user can easily see that an ideal SRB cut produces a diamond of lower carat weight than the maximum possible for the two roughs. In general, the ideal SRB cut is obtained at the expense of losing some carat weight.

Figure 8A:
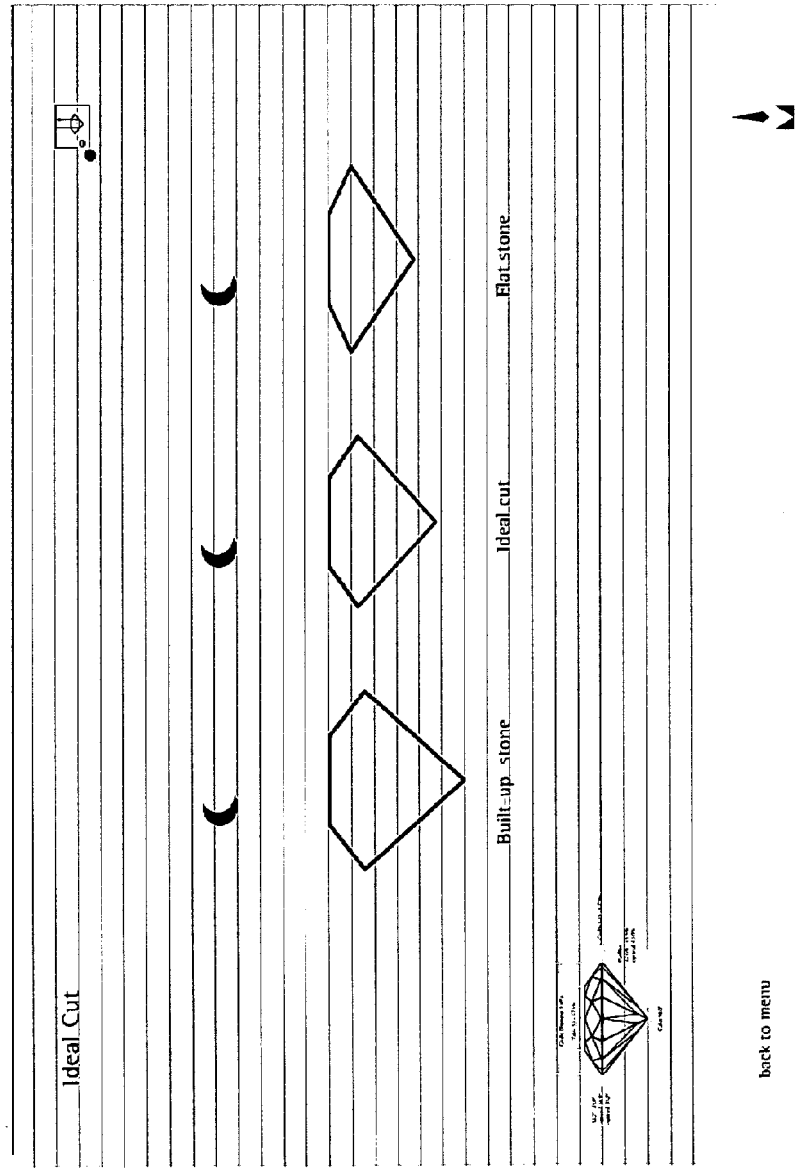
FIGS. 8a-e are screenshots of the pages, of the gemology teaching and gemstone evaluation application explaining the differences in light handling ability between deep, shallow and ideal cut SRB cut diamonds.
Figure 8B:
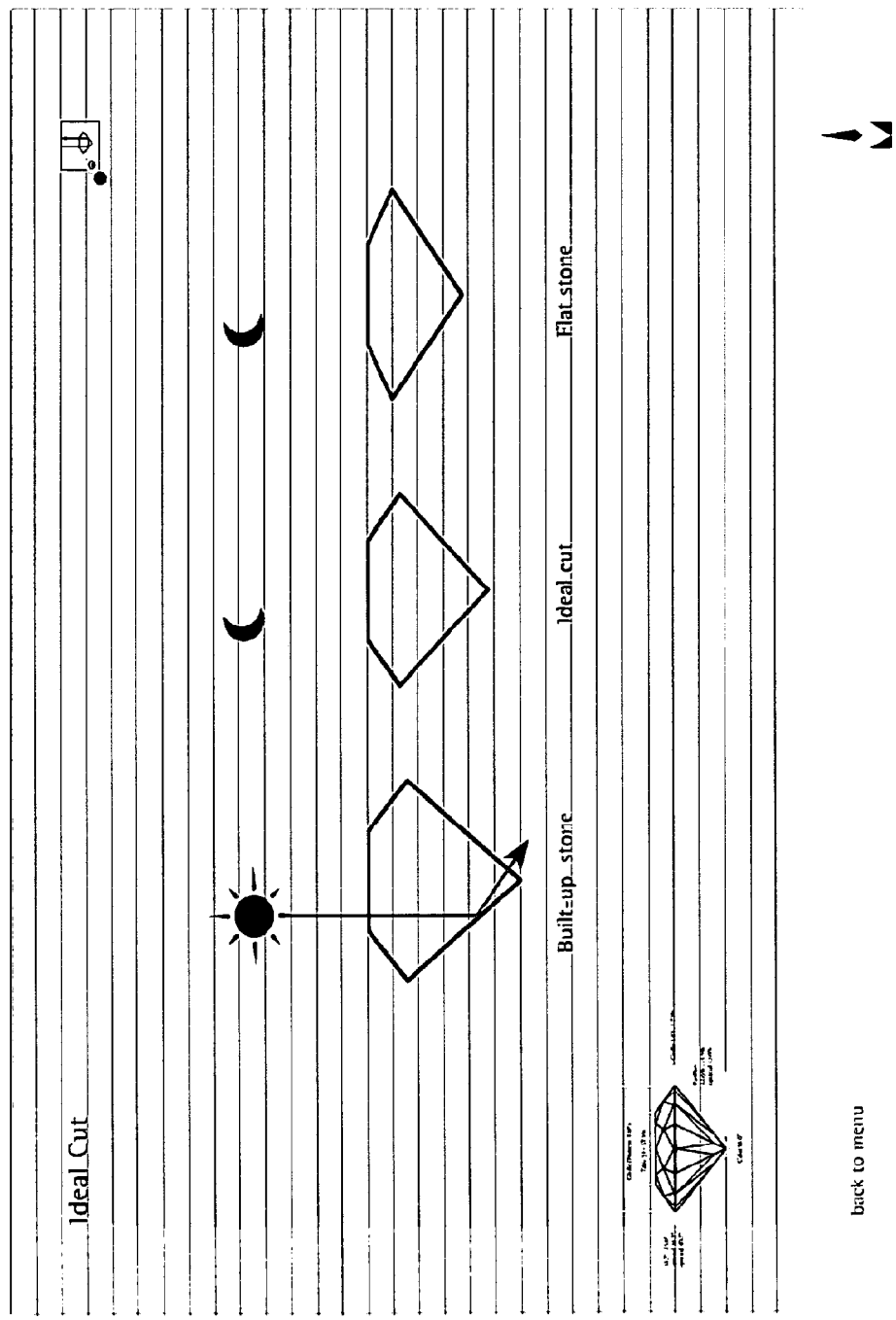
Figure 8C:
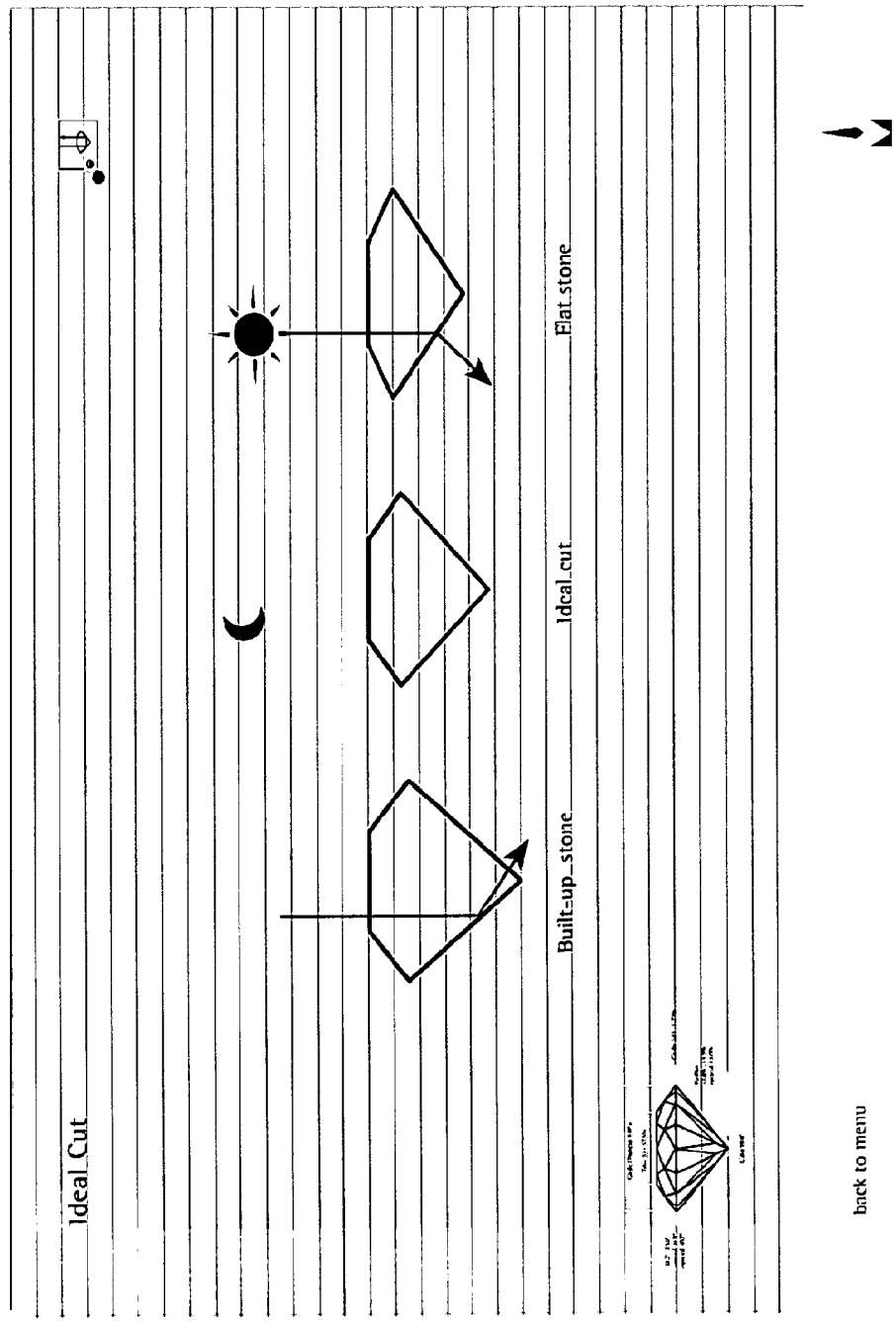
Figure 8D:
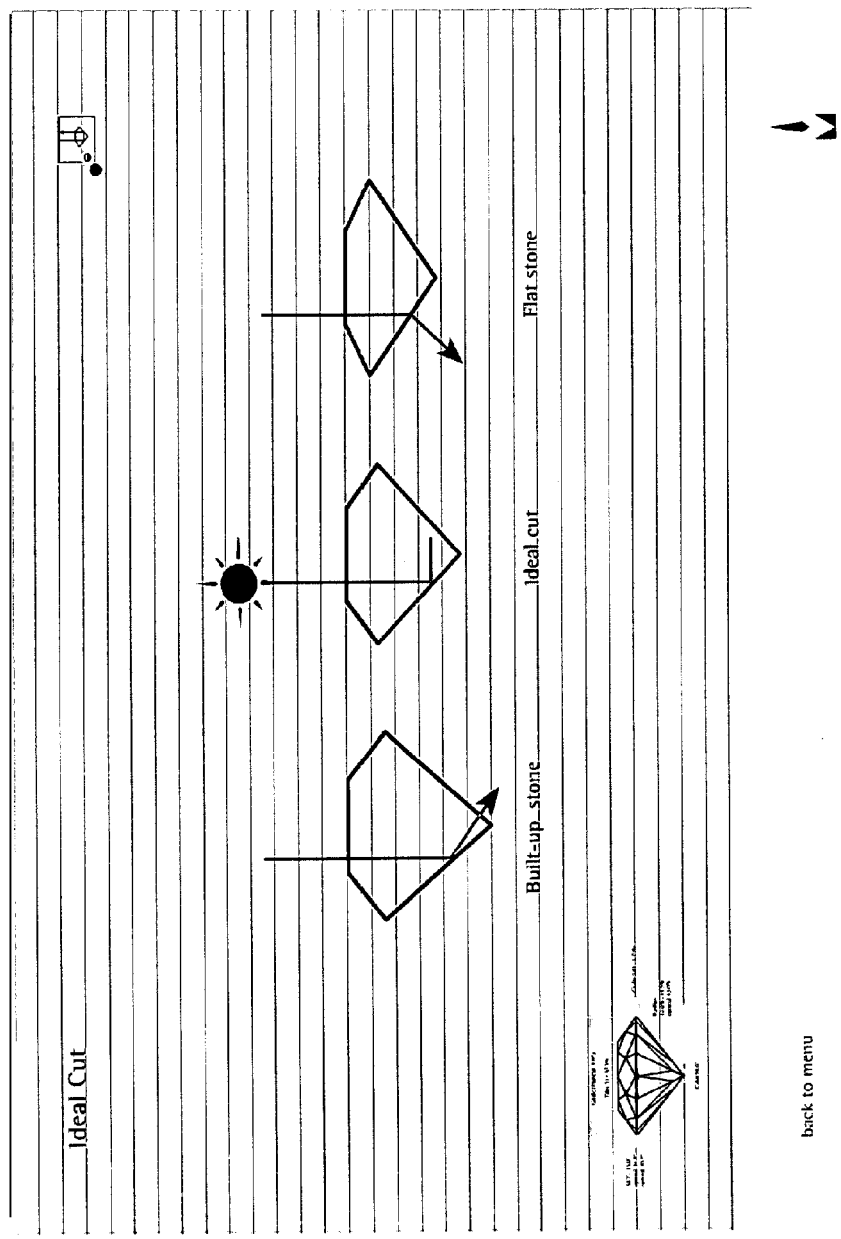
Figure 8E:
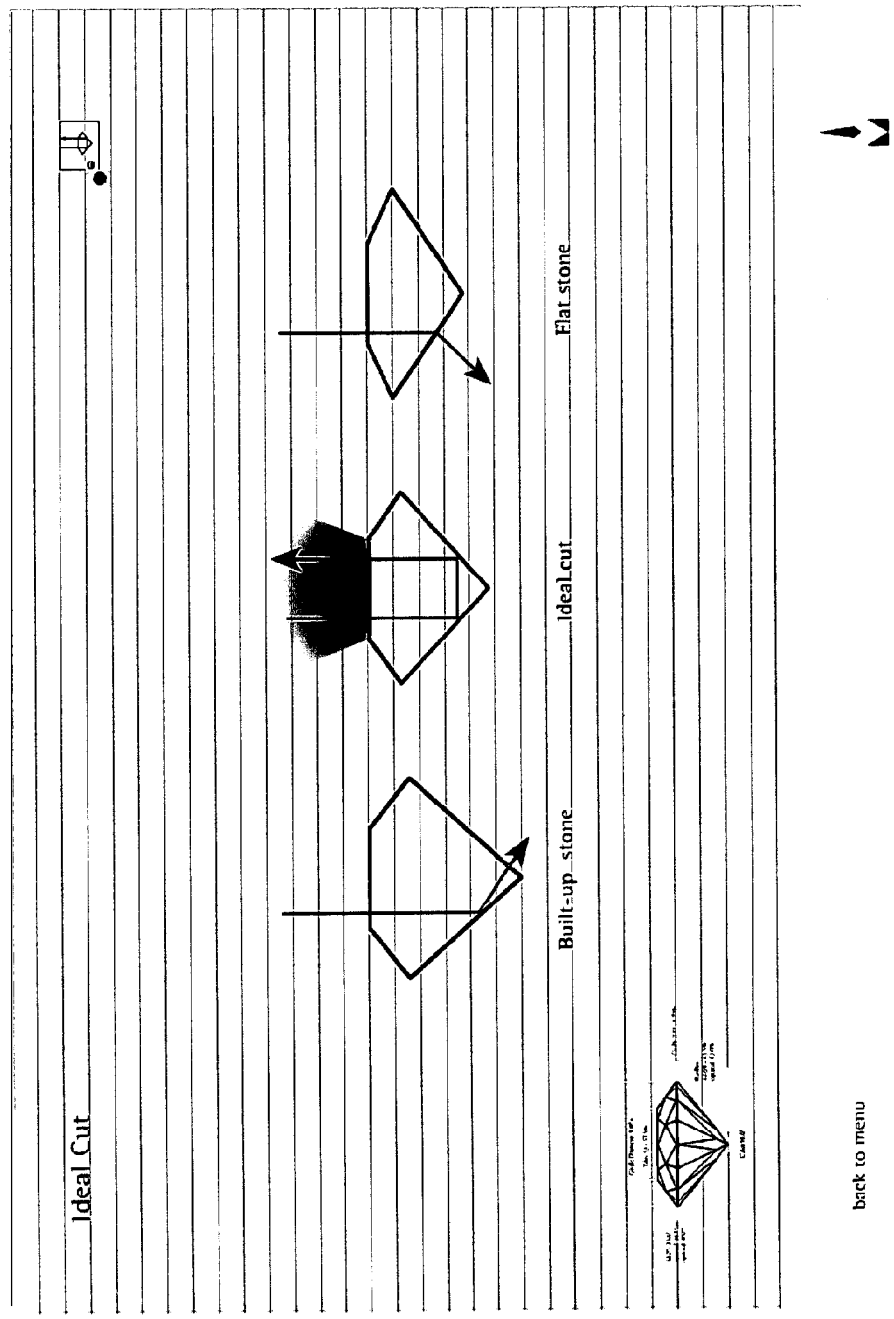

FIGS. 8a-e show gemology teaching pages explaining the differences in light handling ability between deep, shallow and ideal cut SRB cut diamonds. The Figures show exemplary screenshots taken at various points during a moving image presentation executed using Macromedia Flash components. FIG. 8a shows a side-on outline of three SRB cut diamonds, from left to right, a built up stone (deep cut), an ideal cut, and a flat stone (shallow cut), such as may be cut from the two roughs described with reference to FIGS. 7a-h. The three diamonds are in relative darkness, as indicated by the crescent moon hanging over each one. In FIG. 8b, the built-up stone is illuminated from the table side, as indicated by the sun hanging over the gemstone outline. The light ray is traced as it enters the diamond and, as shown, it is reflected off the internal surface of one of the pavilion facets and exits through the other side of the pavilion. Thus, from the table-side, substantially no light is returned. In FIG. 8c, the flat stone is illuminated from the table side, as indicated by the sun hanging over the gemstone outline. The light ray is traced as it enters the diamond and, as shown, it is refracted off the internal surface of one of the pavilion facets and exits through that facet. Thus, from the table-side, again substantially no light is returned. On the other hand, in FIG. 8d, the ideal cut stone is illuminated from the table side. The light ray is traced as it enters the diamond and, as shown, it is reflected off the internal surface of one of the pavilion facets, then off the internal surface of another facet on the other side of the pavilion which directs it back through the table where it exits. Thus, with the ideal cut diamond, the user can see that light is returned through the table. This is indicated by the light beams shining out of the table as shown in FIG. 8e. Thus, the user can easily understand the effect cut has on light handling ability in terms of the light returned through the table by three SRB cuts of deep, shallow and ideal proportions illuminated through the table.

Figure 9A:
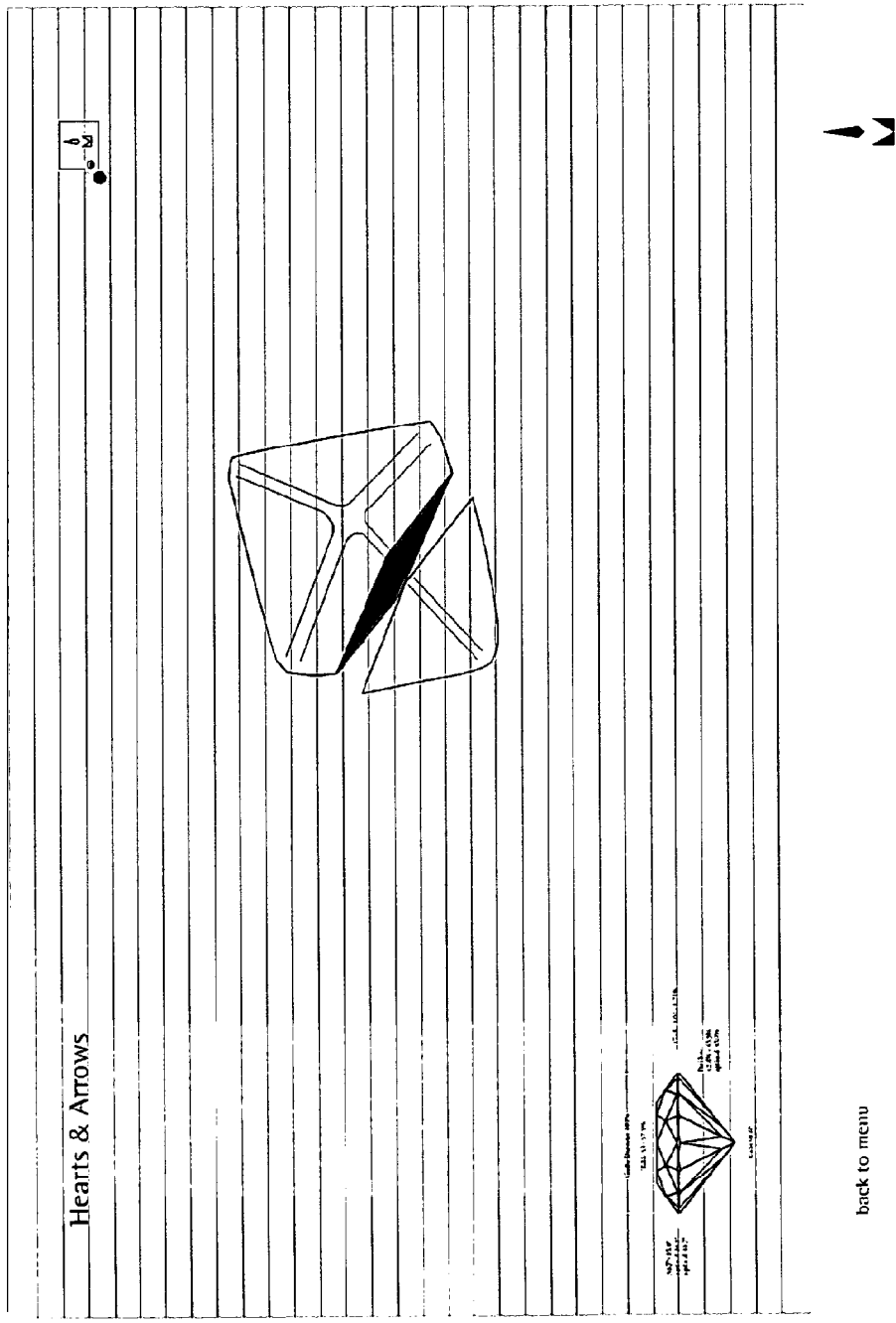
FIGS. 9a-t are screenshots of the pages, of the gemology teaching and gemstone evaluation application describing how an ideal SRB cut diamond is cut from a rough and indicating the phenomenon of "hearts and arrows" that results from a well-cut diamond.
Figure 9B:
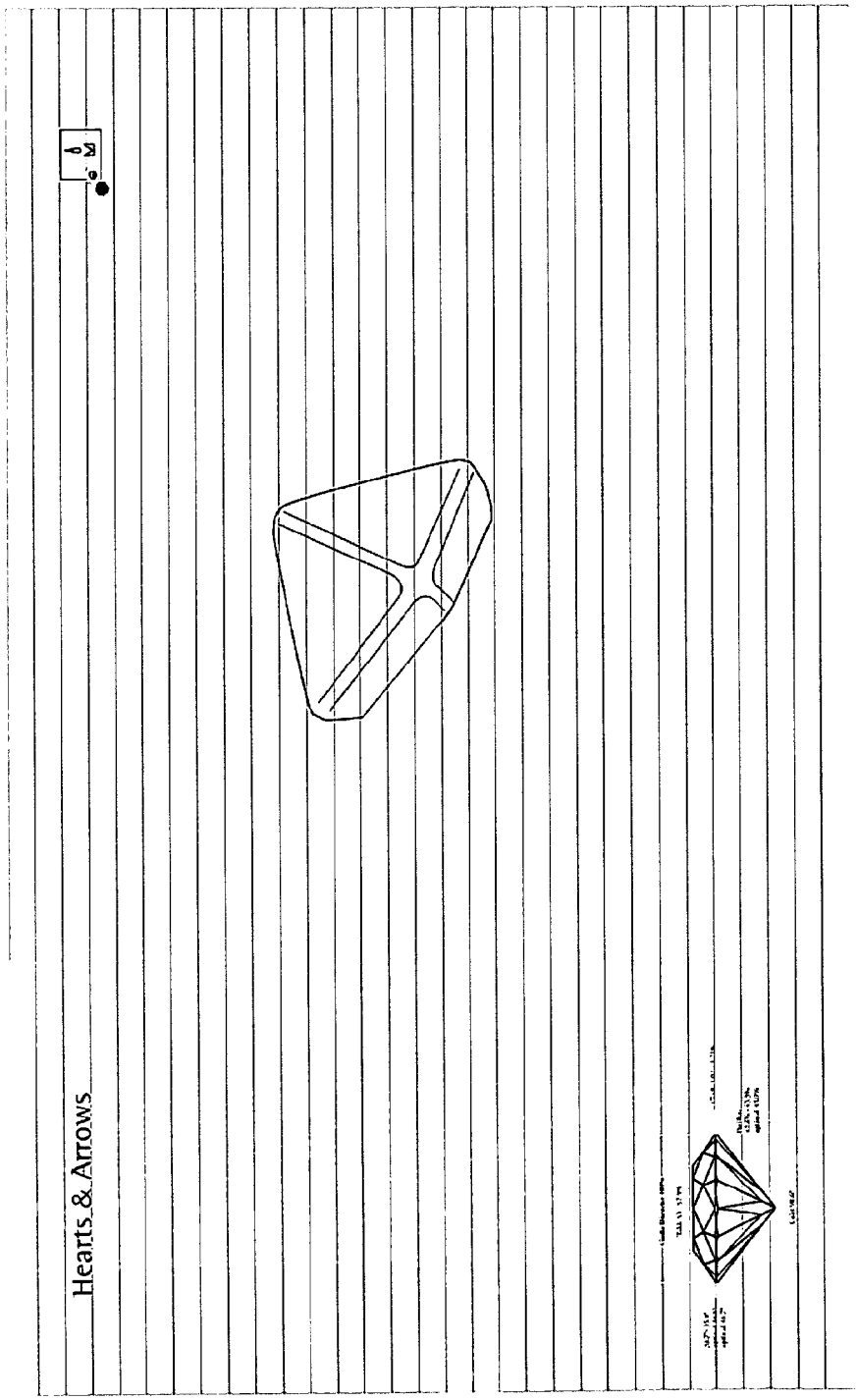
Figure 9C:
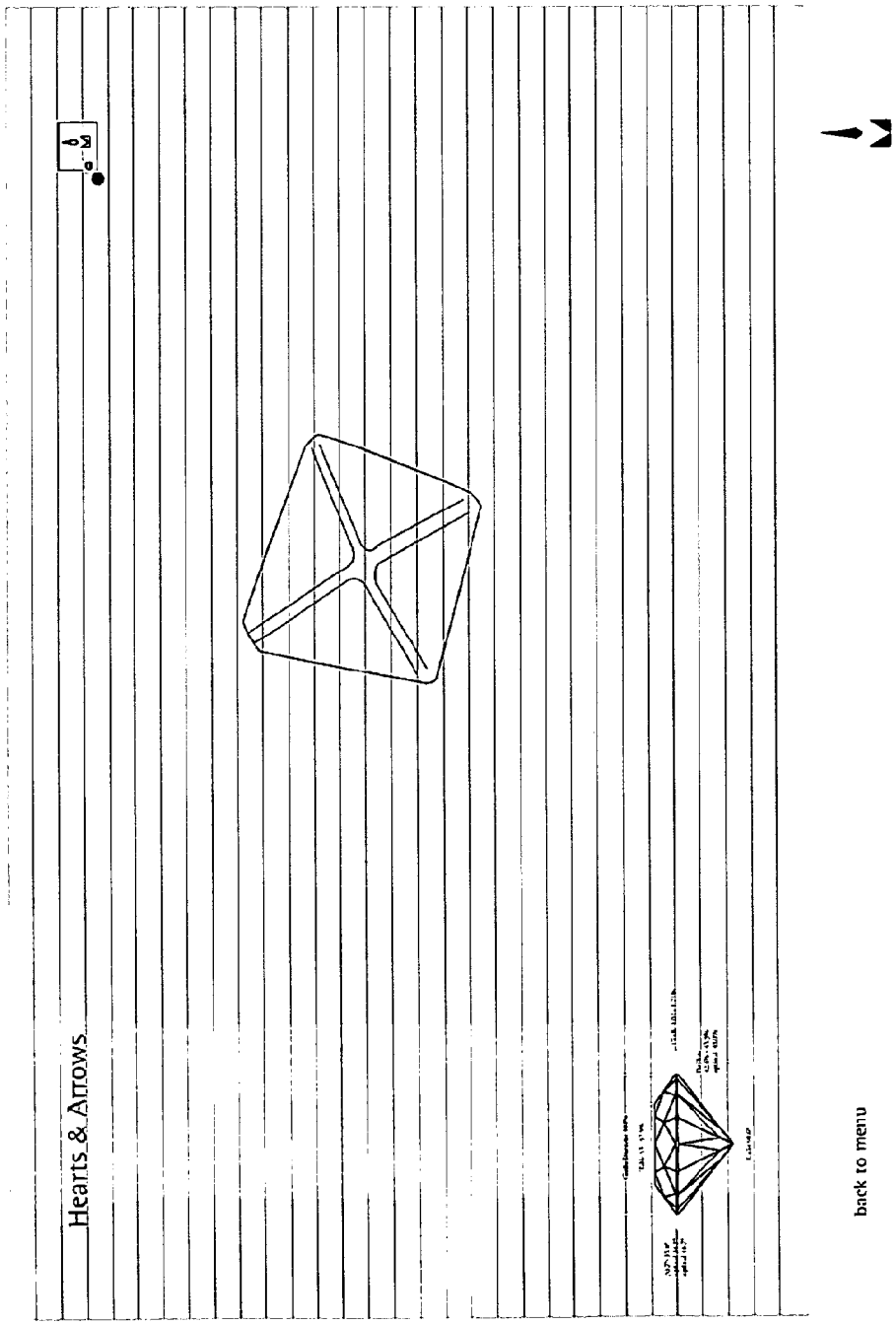
Figure 9D:
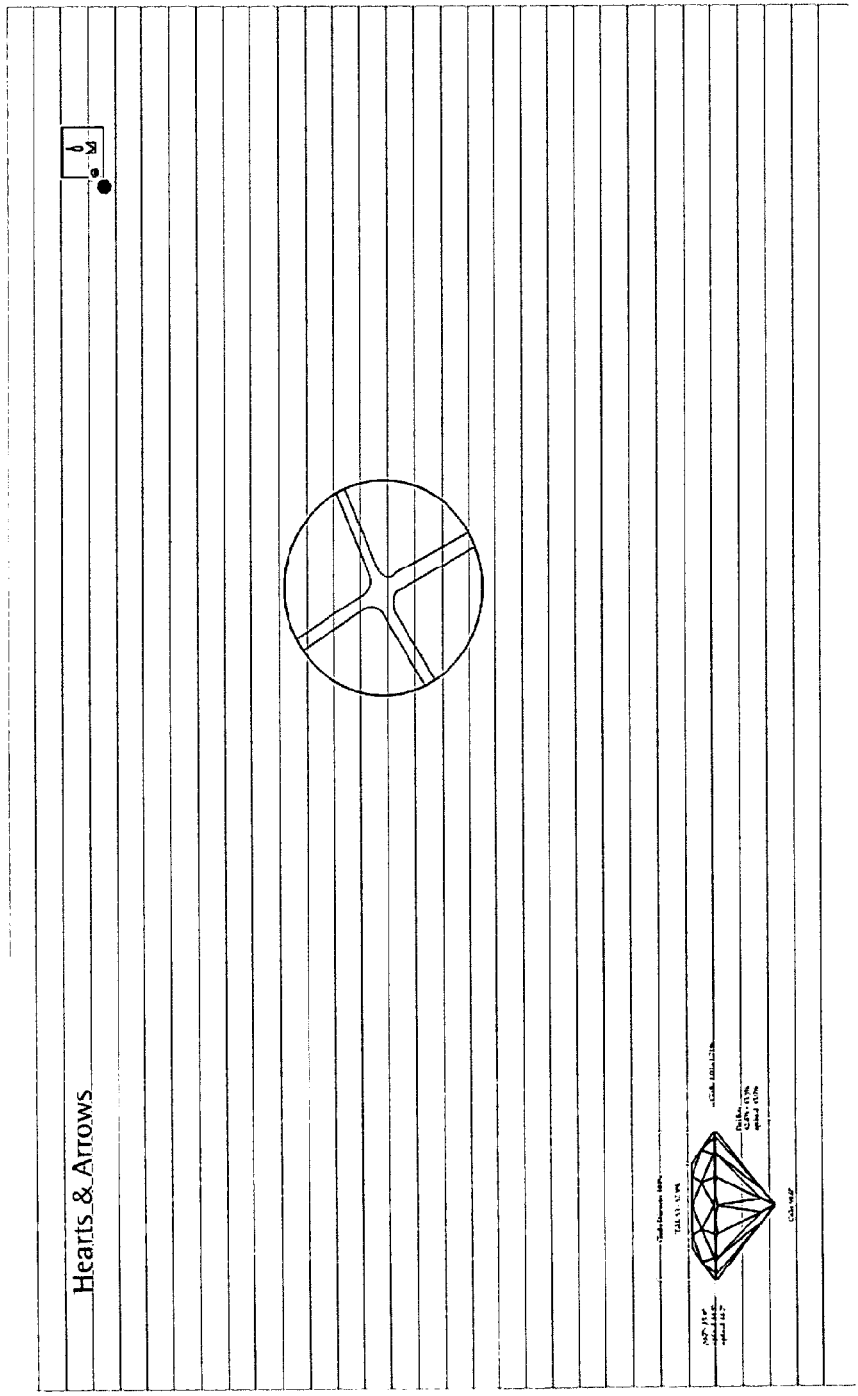
Figure 9E:
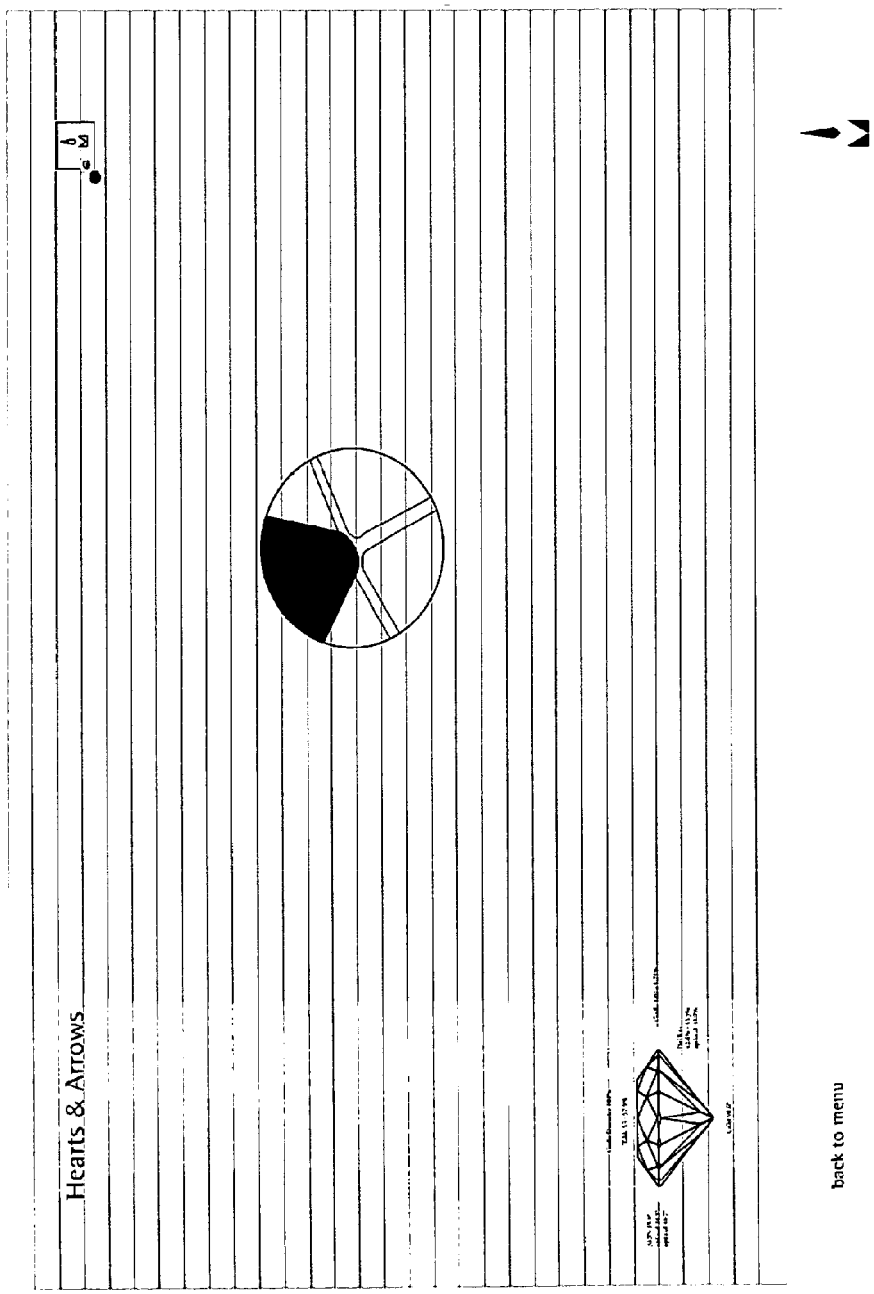
Figure 9F:
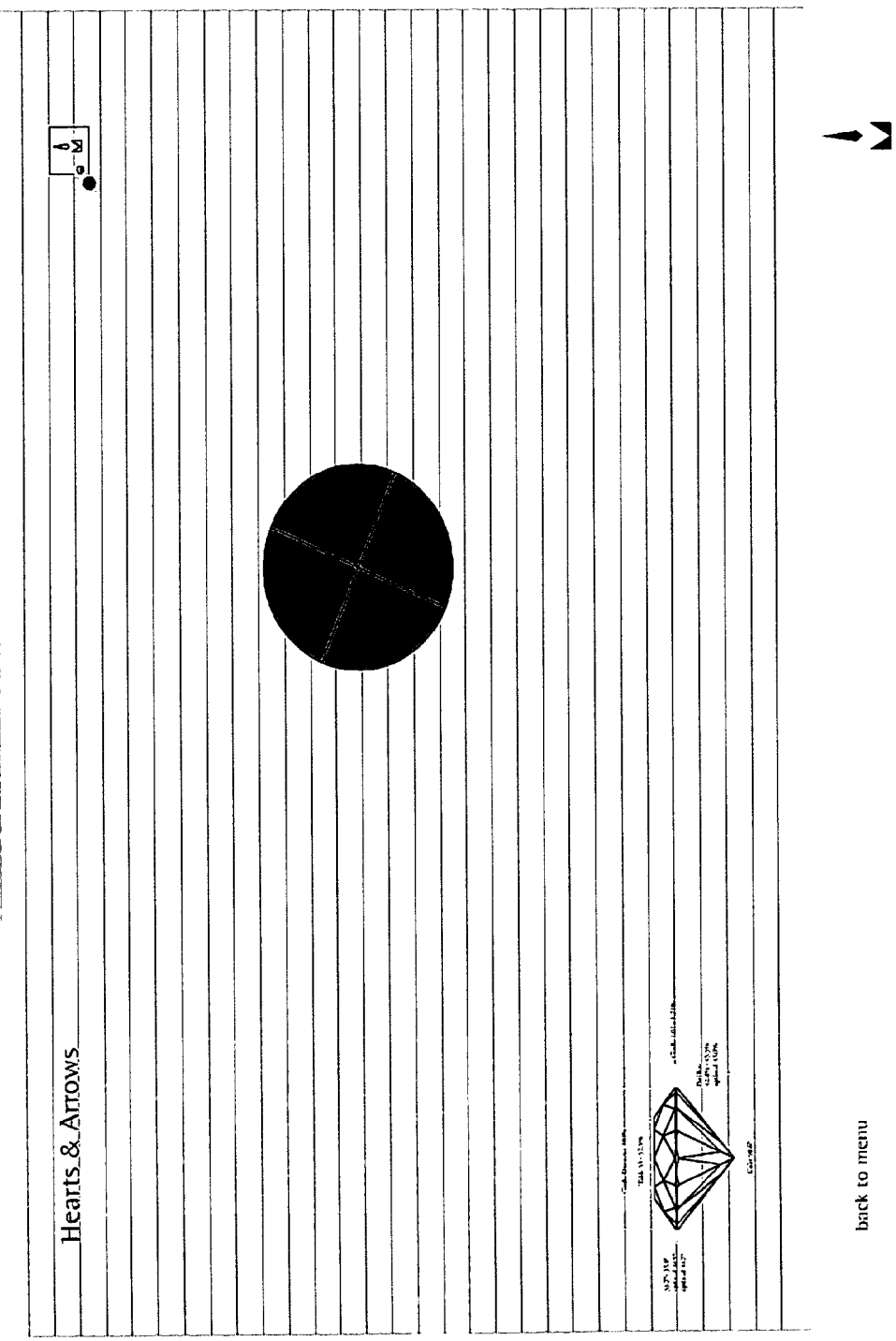
Figure 9G:
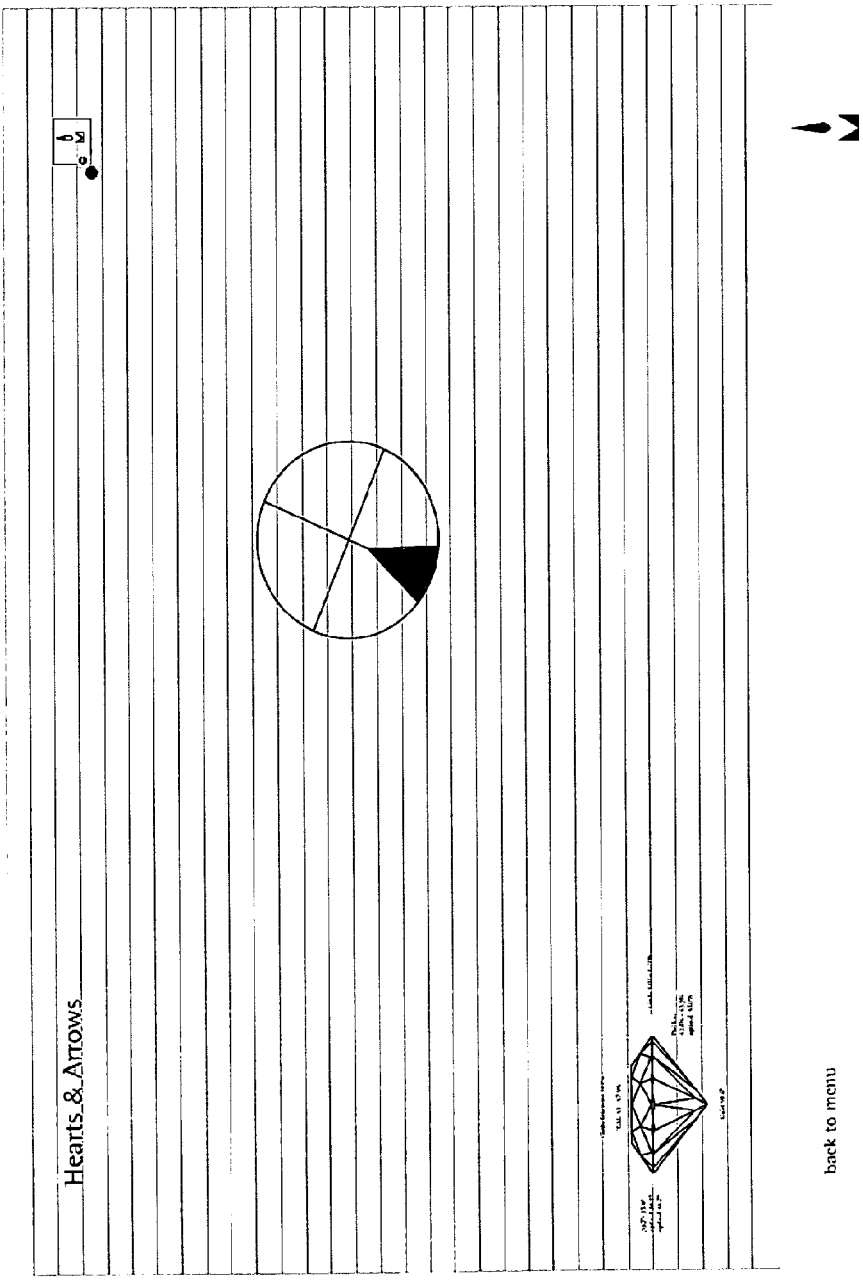
Figure 9H:
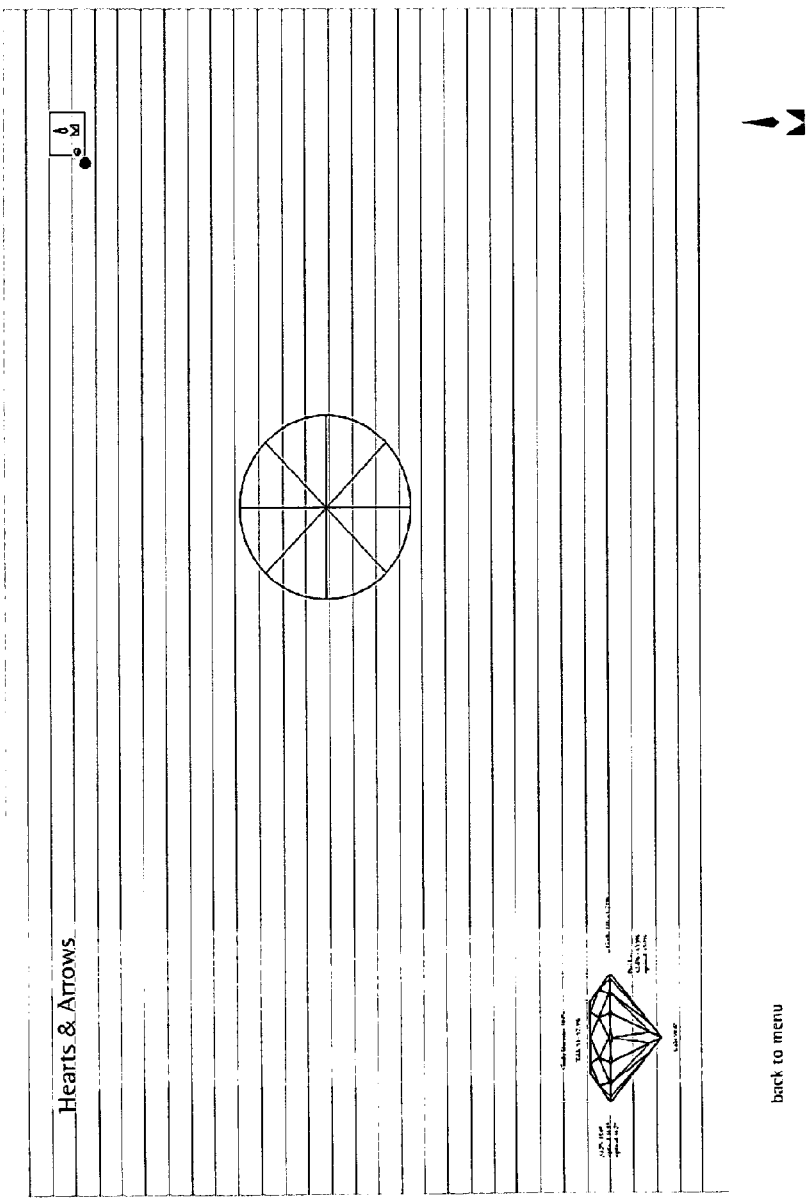
Figure 9I:
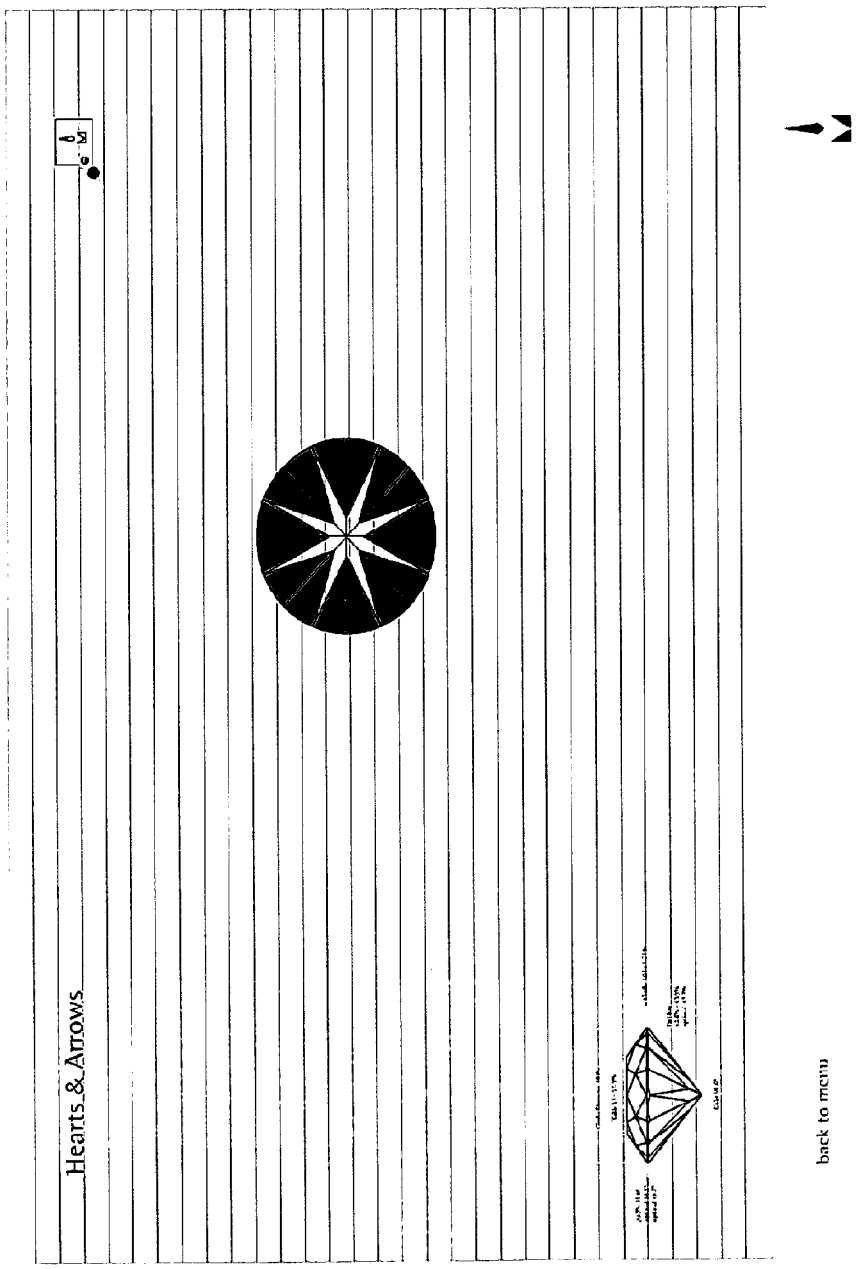
Figure 9J:
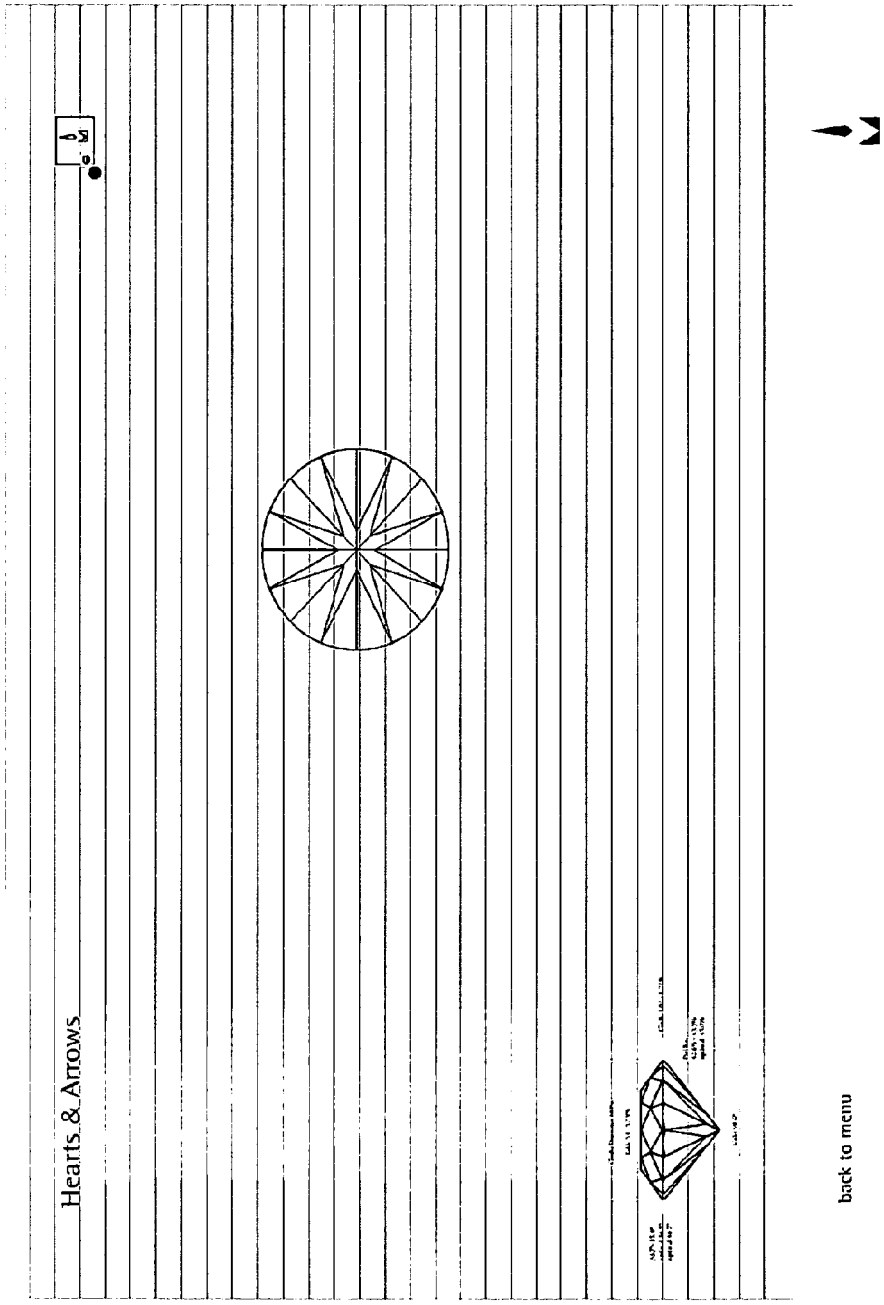
Figure 9K:
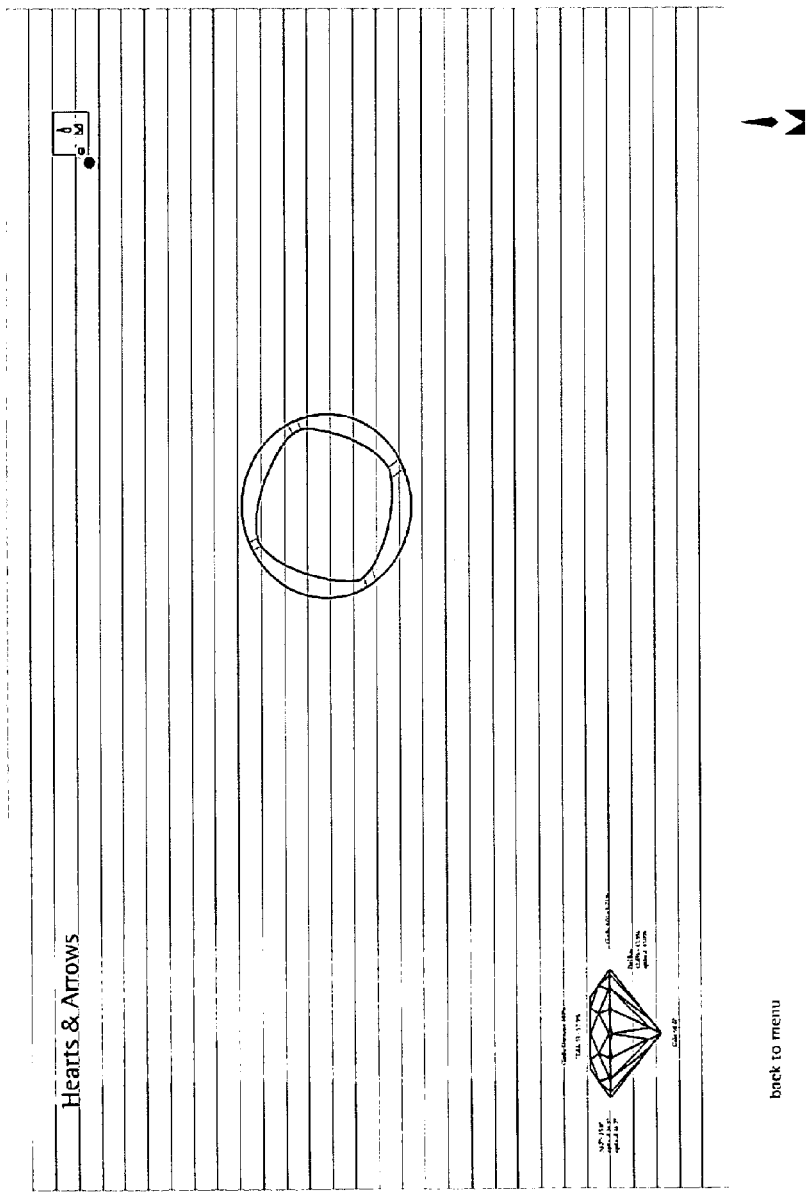
Figure 9I:
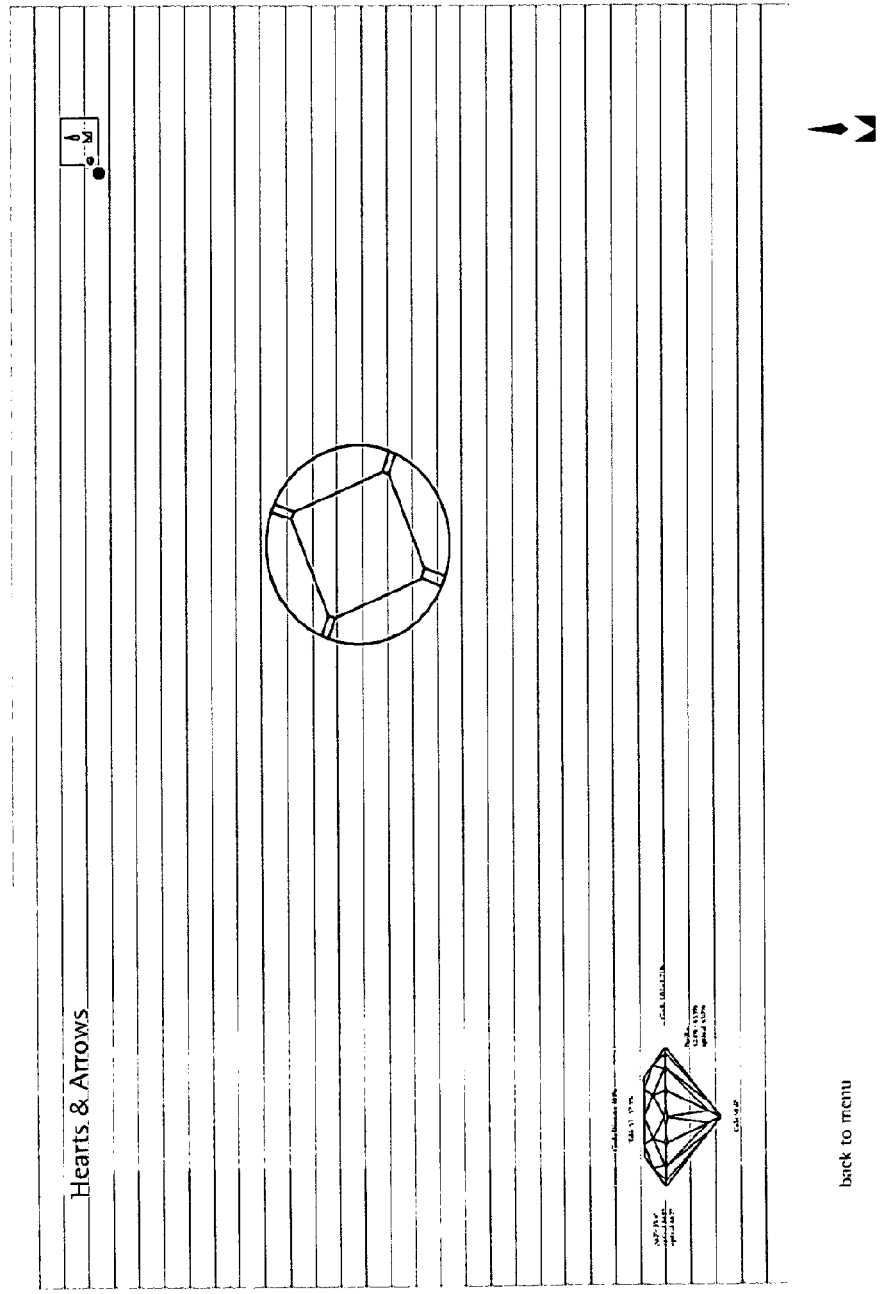
Figure 9M:
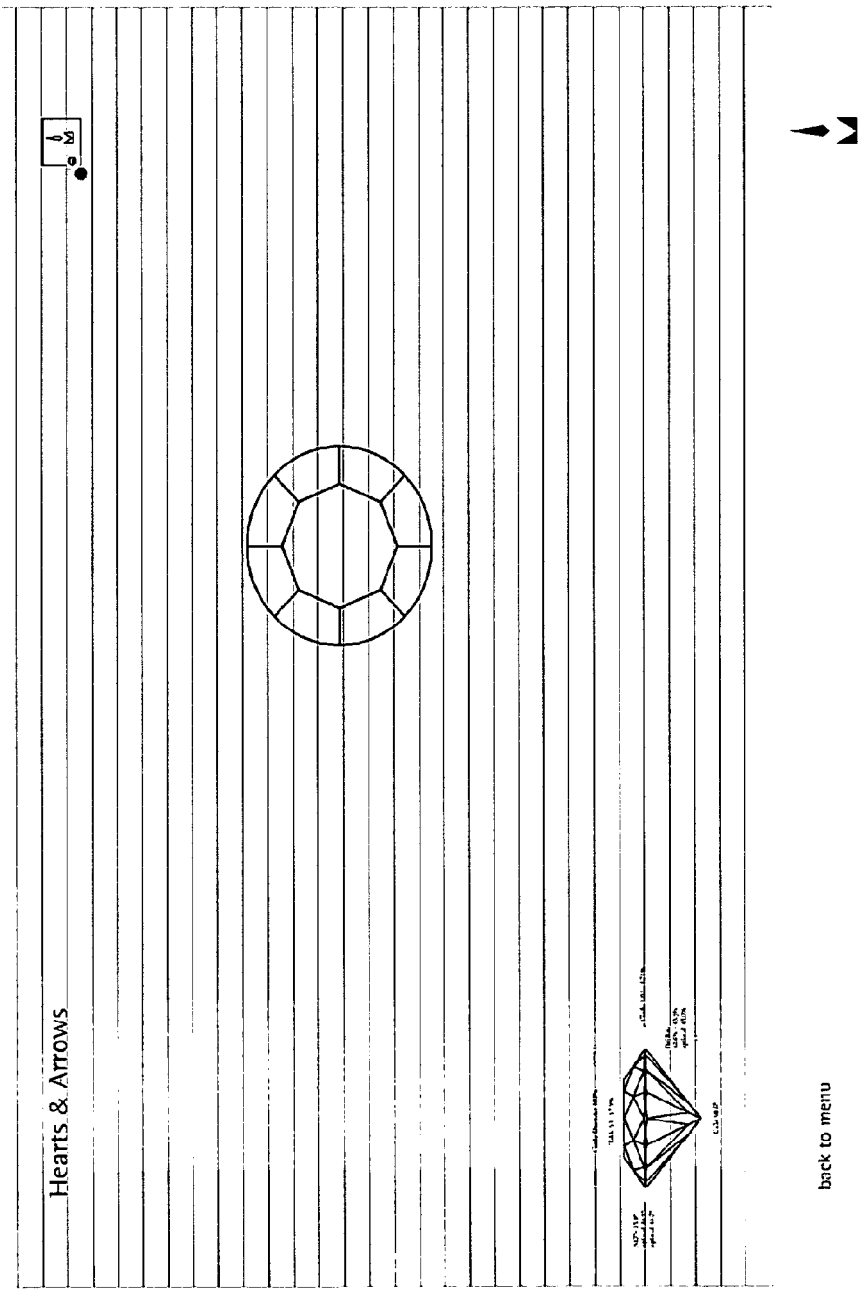
Figure 9N:
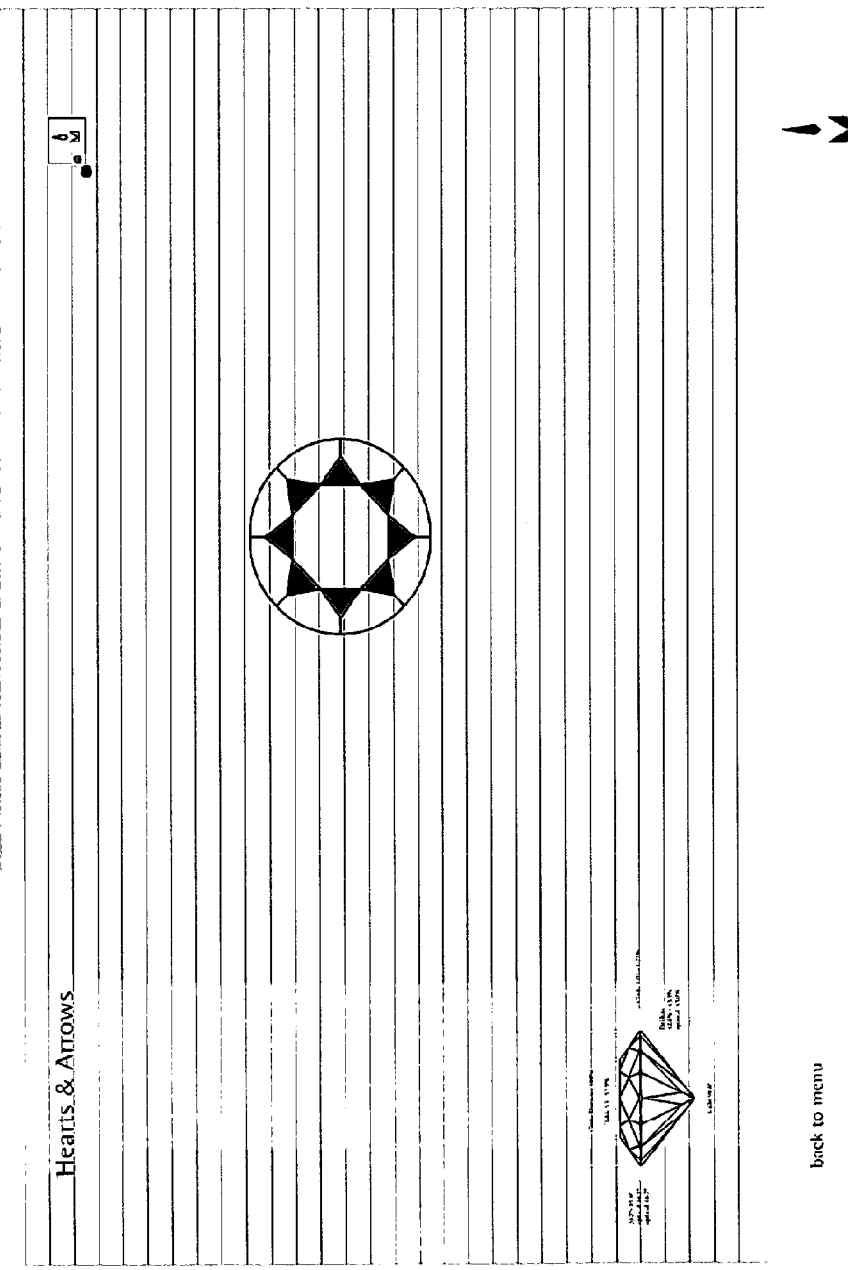
Figure 9O:
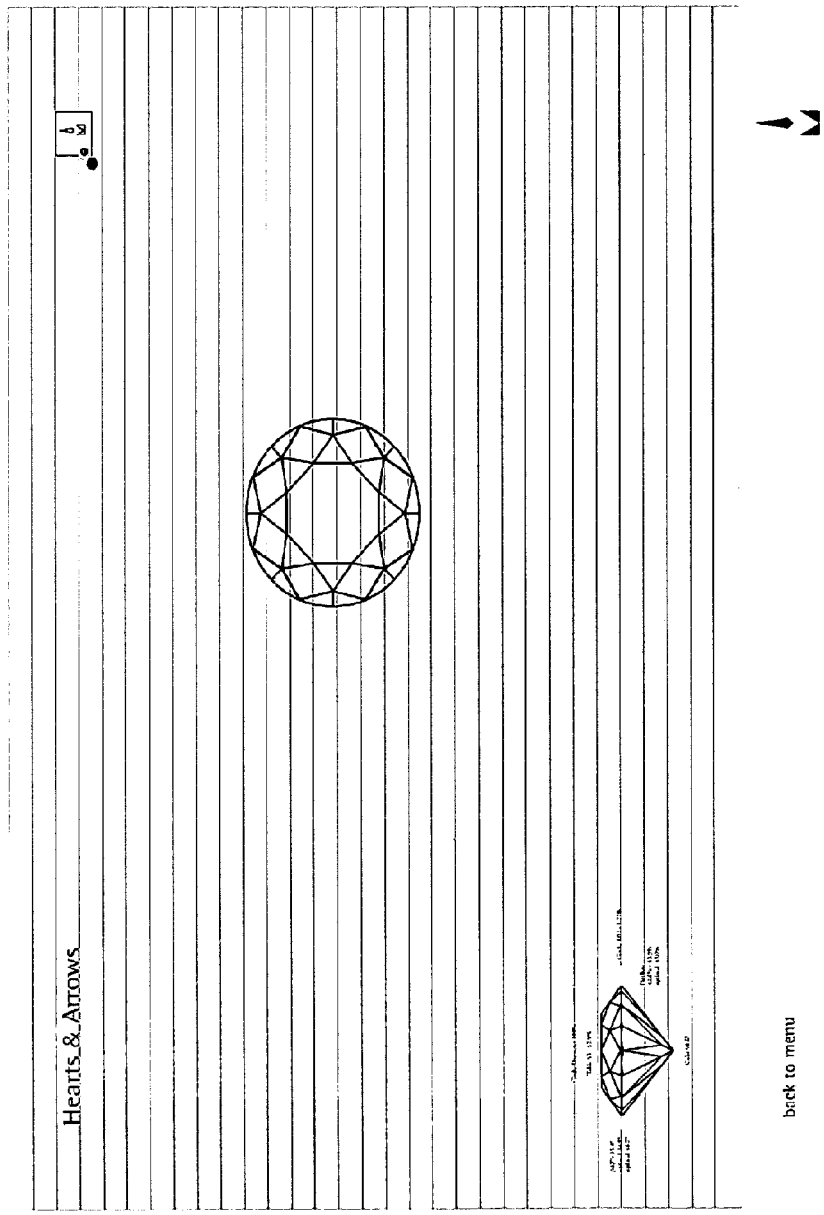
Figure 9P:
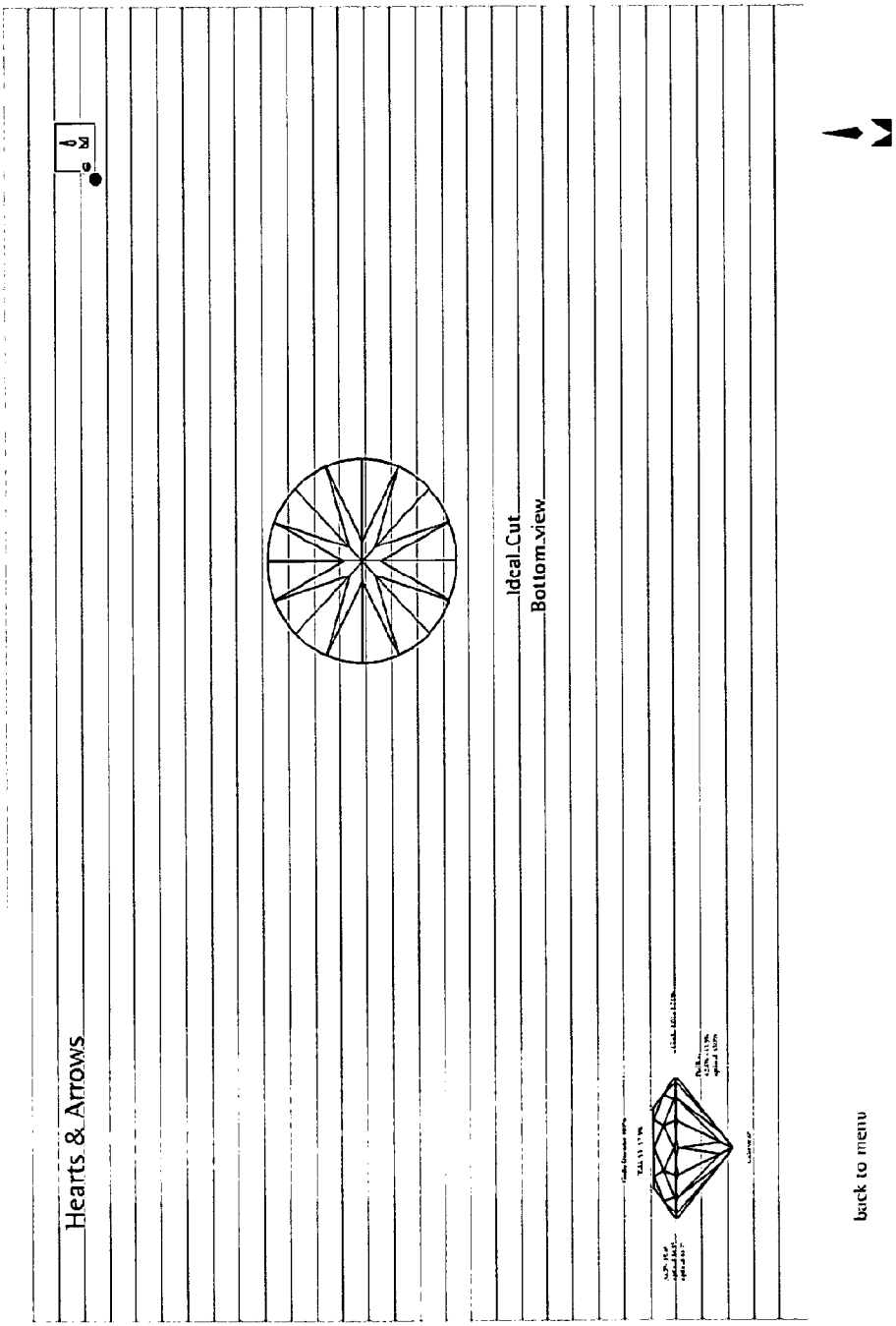
Figure 9Q:
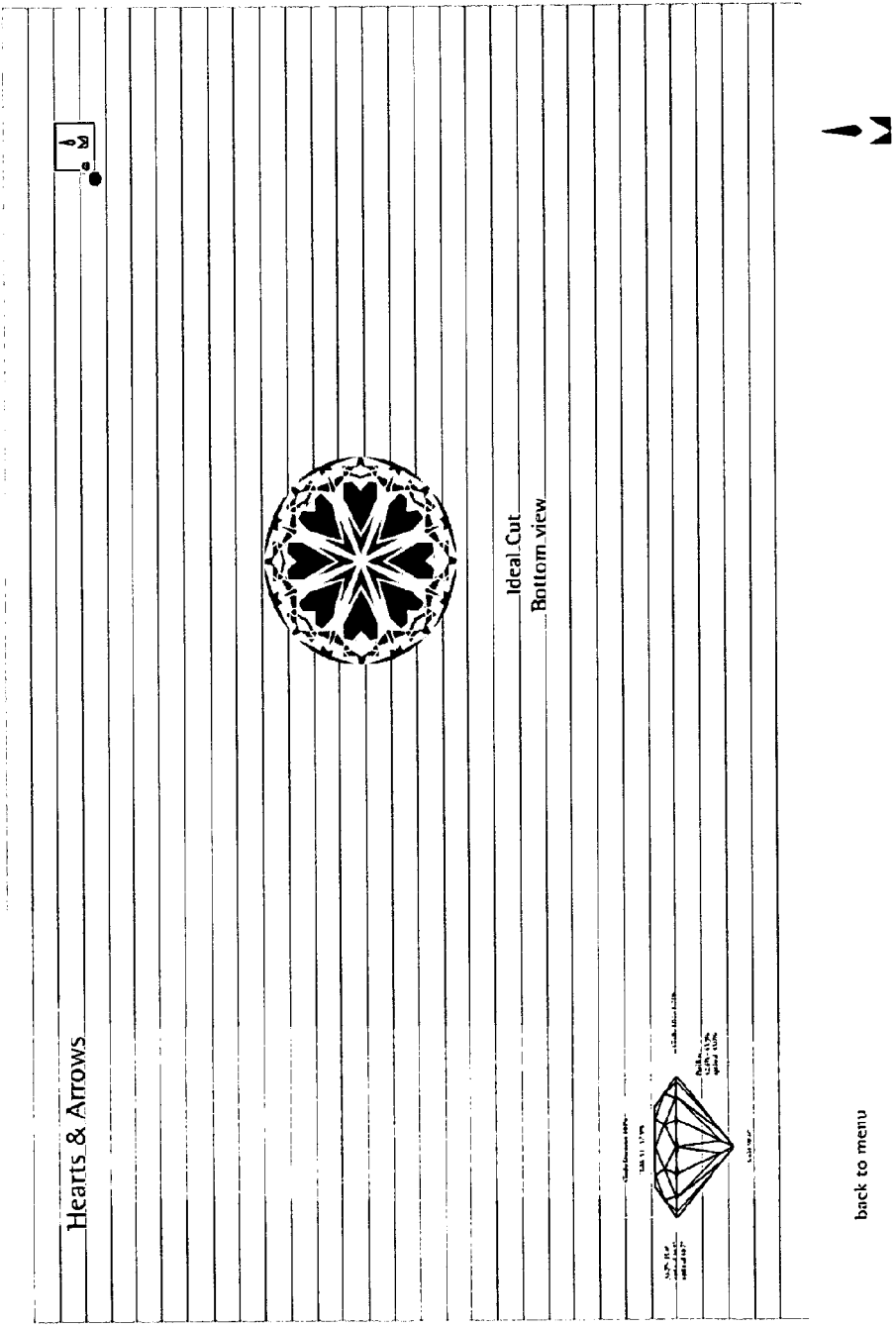
Figure 9R:
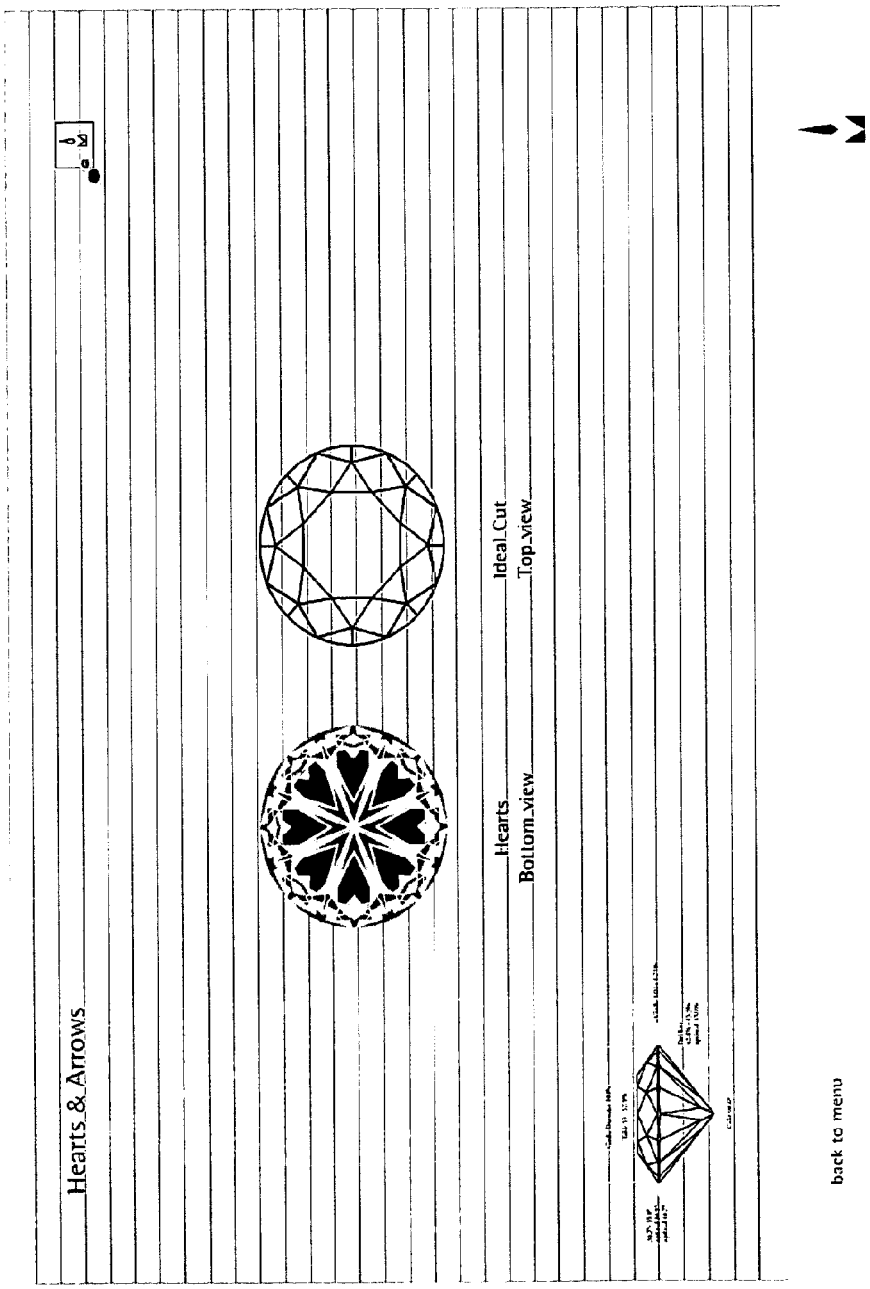
Figure 9S:
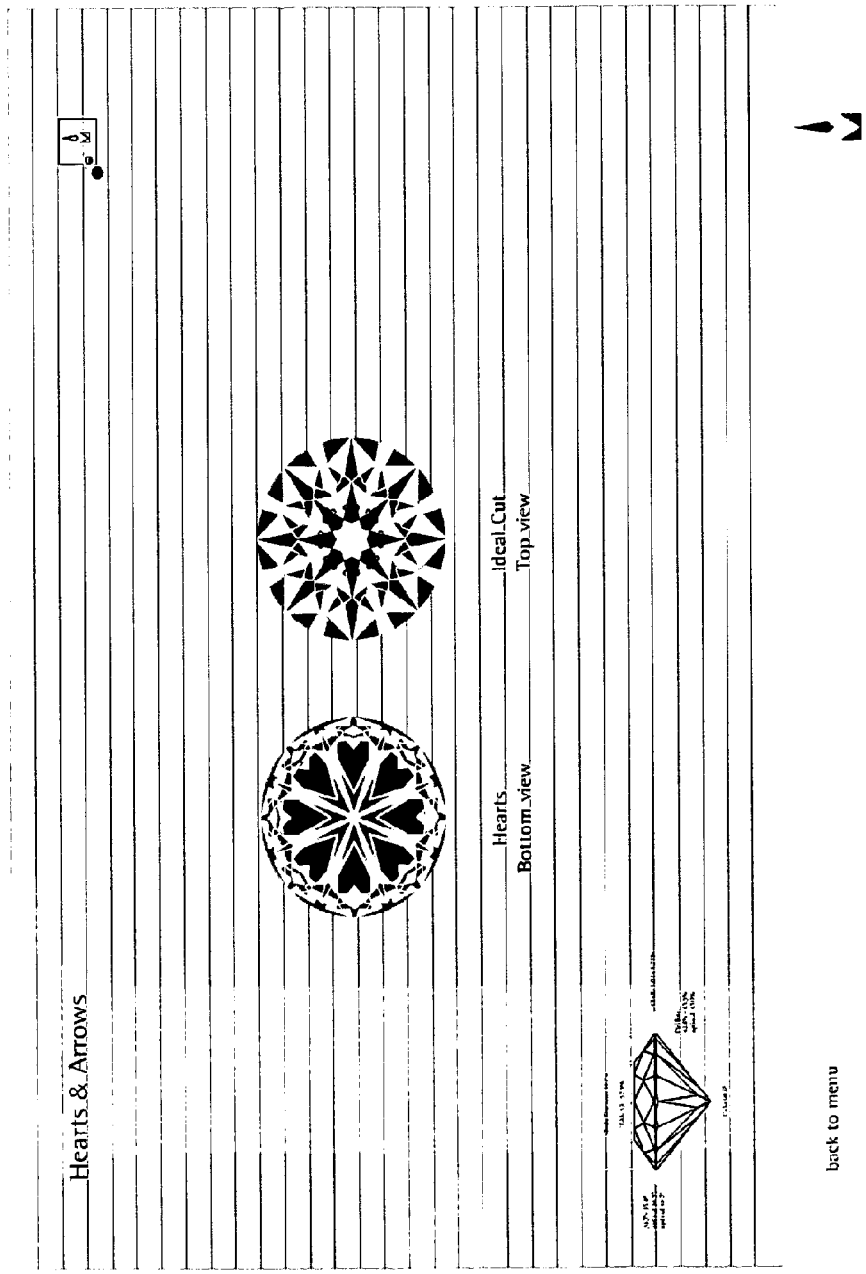
Figure 9T:
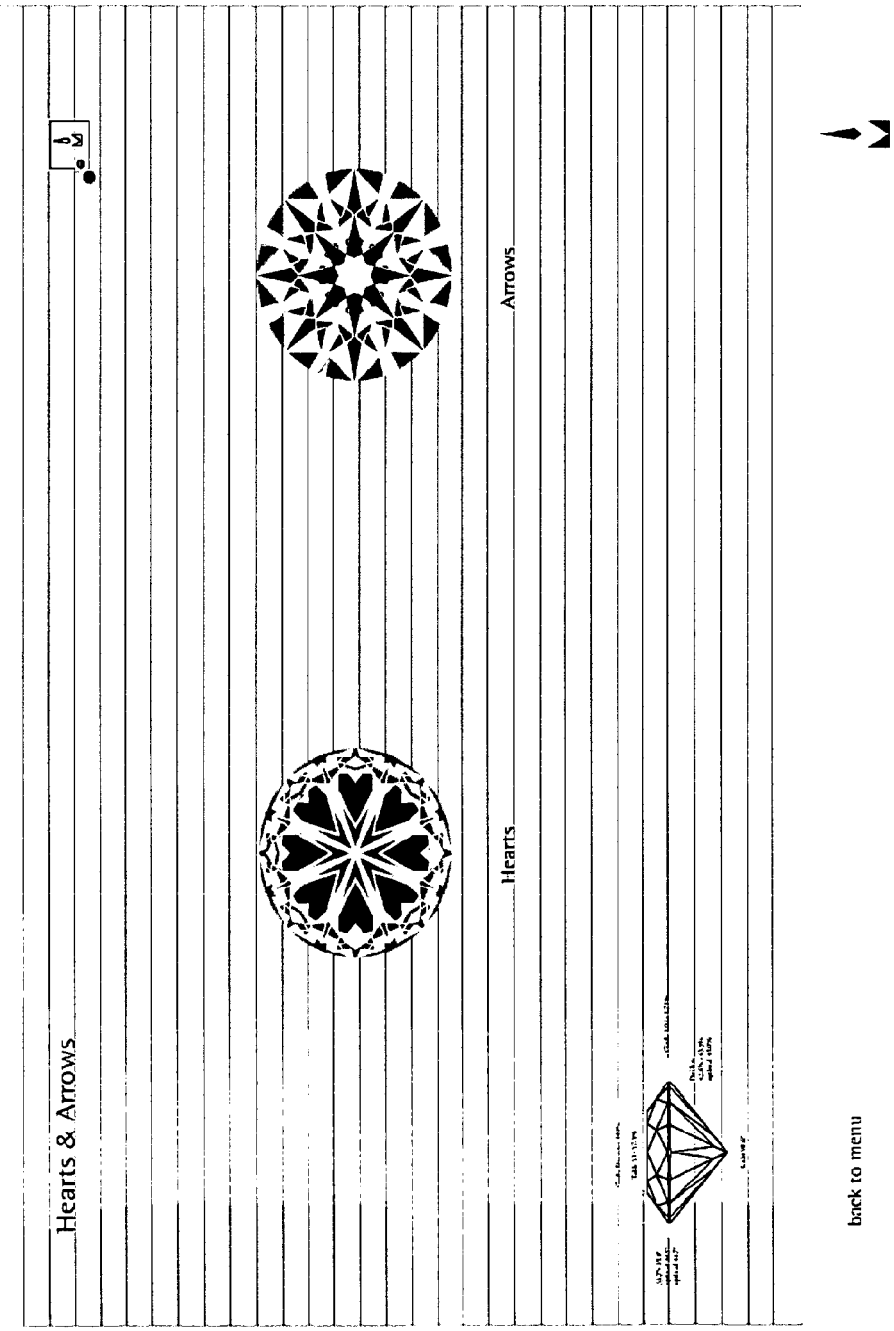

FIGS. 9a-t show the gemology teaching pages describing how an ideal SRB cut diamond is cut from a rough and indicating the phenomenon of "hearts and arrows" that results from a well-cut diamond. The Figures show exemplary screenshots taken at various points during a moving image presentation executed using Macromedia Flash components. FIG. 9a shows a rough being cut into two parts for cutting two SRB cut diamonds. FIG. 9b shows the larger part on its own. FIG. 9c shows the rough part rotated so that the user's viewpoint (with respect to the SRB cut pattern to be cut) is along the axis of symmetry of the diamond from the pavilion end. FIG. 9d shows the rough part with the excess stone around the girdle cut away. FIG. 9e shows the rough part with a first of the major pavilion-side facets cut away. FIG. 9f shows the rough part with three further of the major pavilion-side facets cut away at 90°, 180° and 270° respectively to the first cut facet. FIG. 9g shows the rough part with a further major pavilion-side facet at 45° to the first cut facet cut away. FIG. 9h shows the rough part with three further major pavilion-side facets cut away at 135°, 225° and 315° respectively to the first cut facet. FIGS. 9i and 9j shows the rough part with 8 minor pavilion-side facets cut away at the intersections between each of the major facets.

FIG. 9k shows the rough part rotated through 180° so that the user's viewpoint (with respect to the SRB cut pattern to be cut) is along the axis of symmetry of the diamond from the table-side. FIG. 9l shows the rough part with the first four of the major table-side facets cut away at 0°, 90°, 180° and 270°. FIG. 9m shows the rough part with a further four major table-side facets cut away at 45° 135°, 225° and 315°. FIGS. 9n shows the rough part with 8 minor table-side facets cut away at the corner between each of the major facets and the table. FIG. 9o shows the rough part with 16 girdle facets cut away.

FIG. 9p shows the now completely cut (though not polished) diamond rotated through 180° again so that the user's viewpoint is along the axis of symmetry of the diamond from the pavilion end. FIG. 9q shows the cut diamond viewed from the pavilion end as illuminated from the table-side. The so-called "hearts" pattern is clearly visible with 8 hearts arranged around the center of the stone. FIG. 9r shows the "hearts" pattern moved to the left of the diamond which is now rotated through 180° again so that the user's viewpoint is along the axis of symmetry of the diamond from the table-side. FIG. 9s shows the cut diamond viewed from the table side as illuminated from the pavilion end. The so-called "arrows" pattern is clearly visible with 8 pairs of aligned arrows arranged around the center of the stone. FIG. 9*t* "arrows" pattern moved to the right of the "hearts" pattern. Thus, the user can clearly see the "hearts and arrows" patterns produced by a well-cut ideal SRB cut diamond.

In further embodiments of the present invention, a spoken narrative may be included in the presentation of the gemology teaching pages as described with reference to FIGS. 6*a-g*, 7*a-h*, 8*a-e*, and 9*a-t*. The narrative explains the meaning of the 4 C's, the differences between shallow, deep and ideal cut SRB cut diamond in terms of both carat weight and light handling ability, and the phenomenon of "hearts and arrows" produced by a well-cut ideal SRB cut diamond. Narrative elements accompany each of FIGS. 6*a-g*, 7*a-h*, 8*a-e*, and 9*a-t* and may follow, in substance, the written description in this document corresponding to those Figures.

Having viewed and/or listened to all the gemology teaching pages, the user should have a basic understanding of the meaning of the 4 C's, the differences between shallow, deep and ideal cut SRB cut diamond in terms of both carat weight and light handling ability, and the phenomenon of "hearts and arrows" produced by a well-cut ideal SRB cut diamond. The user is thus in a position to understand the effect of cut on light handling ability to a sufficient level to be able to evaluate the light handling ability of a cut gemstone for himself or herself and to appreciate the effect of cut on the value of a gemstone. The user is now in a position to be able to make effective use of optical property evaluation module 58.

Figure 10A:
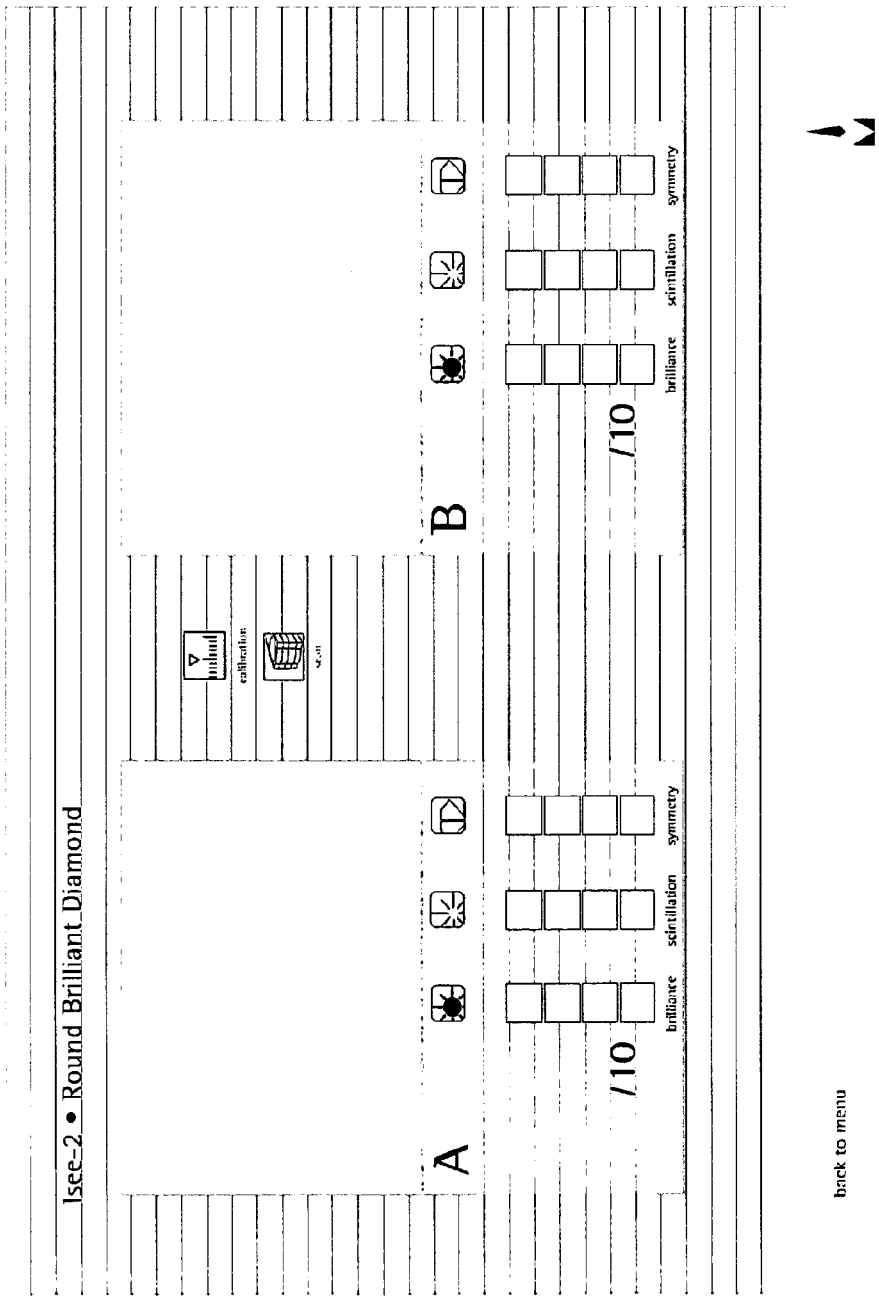
FIGS. 10a-j are screenshots of the user interface screen, of the gemology teaching and gemstone evaluation application for controlling the operation of the apparatus for measuring optical properties of a gemstone and for viewing the gemstone and representations of optical properties of the gemstone.

FIG. 10*a* shows a screen shot of the main screen of the optical property evaluation module 58. On the right and left sides of the main menu screen are two boxes for displaying images and optical properties of two different diamonds, captured in separate scanning operations using apparatus 44. An image of a diamond on the right or left sides of the main menu screen may either be a "live" image as currently being captured by camera 30 or a "video" image as previously captured during a scanning operation and stored in the hard disk drive of the PC 36. A "video" image may be presented as a moving image with the diamond being shown illuminated in consecutive rotational positions of concave surface 26. Beneath each image measurements of the diamond's optical properties of brilliance, scintillation and symmetry represented as a graphical bar chart may be displayed. To begin with, neither of these boxes display any information. Two push buttons are presented in the center of the screen for user control of the computer program and apparatus—a "Calibration" push button and a "Scan" push button. The user may select one the two boxes by clicking anywhere within the box. This means that the optical property evaluation module 58 will display the results of performing a scan or calibration procedure in the selected box, leaving the unselected box displaying the results of any previous procedure. In this way, two diamonds may be scanned in separate scanning operations and the results (including moving video images) displayed side by side in the two boxes. Let us assume that the user has initially clicked on the left hand box and thus selected that box for an initial calibration and a first diamond scan. The process is as follows.

Figure 10B:
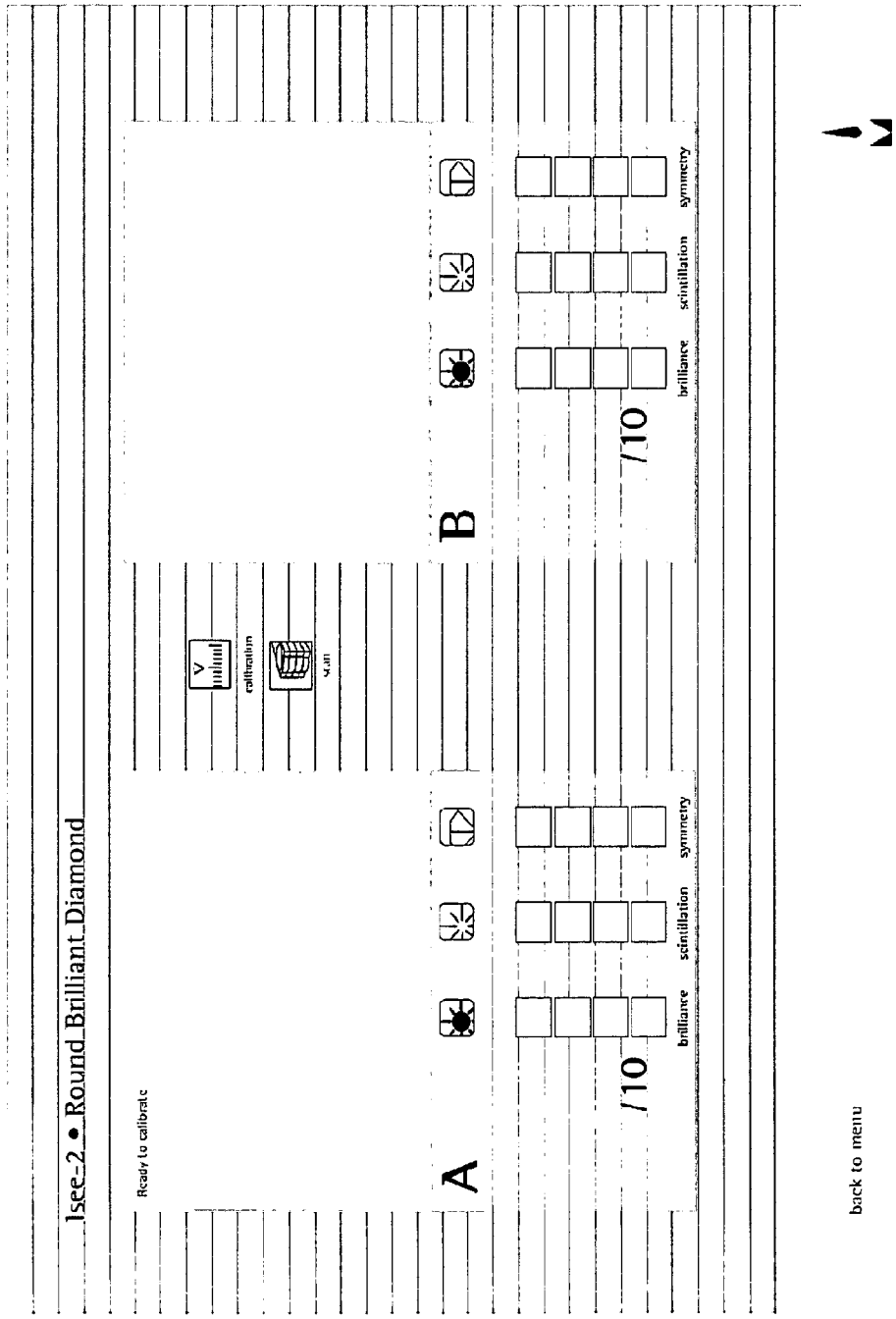

By clicking on the "Calibration" push button the user is taken through the process of calibrating the apparatus. Calibration is preferably performed immediately prior to scanning. FIG. 10*b* shows a screen shot of the calibration screen of the optical property evaluation module 58. Calibrating the system is necessary to compensate for variations in the intensity of the light produced by annular light 24. During calibration, the left hand box displays a live image captured by camera 30. Overlayed on the live image are three small squares which indicate three areas at which the intensity of light will be measured. Calibration is performed by rotating concave surface 26 to a predetermined position, and placing a mirror on the platform in a predetermined position. The mirror has two neutral density filters which partially overlap but each other and both partially cover the mirror surface, resulting in three areas on the mirror with different density filtering (one without a filter, one with one filter, the other with two filters).

Figure 10C:
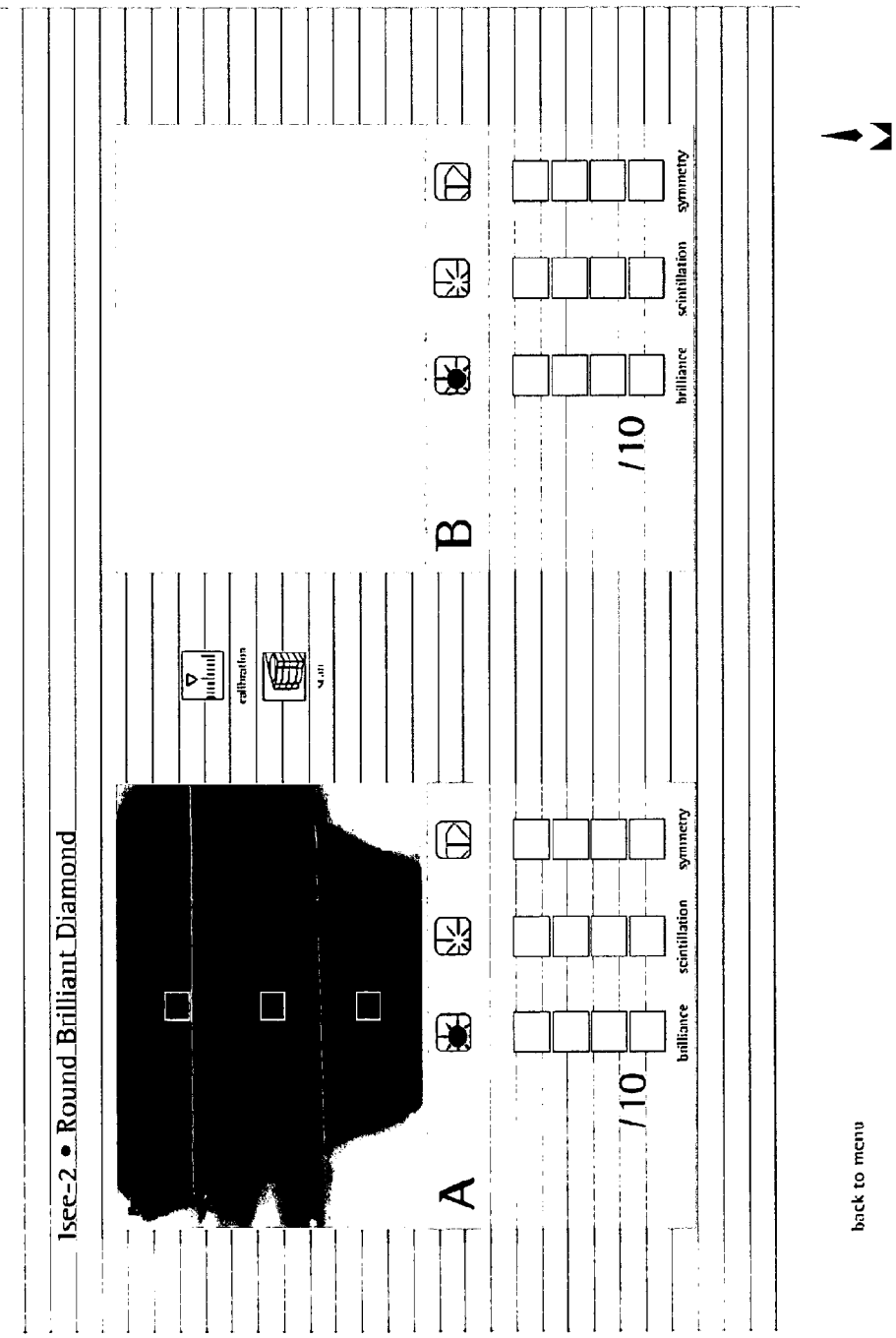

FIG. 10*c* shows a screen shot of the calibration screen of the optical property evaluation module 58 with the mirror in place. An image captured by camera 30 is displayed in the left hand box. The intensity of light at the three areas is then analyzed by integrating the light intensity levels over pixels in each of the three areas to determine a total light intensity level received at each area. These total light intensity levels are then used to adjusts gain and brightness settings of camera 30.

Figure 10D:
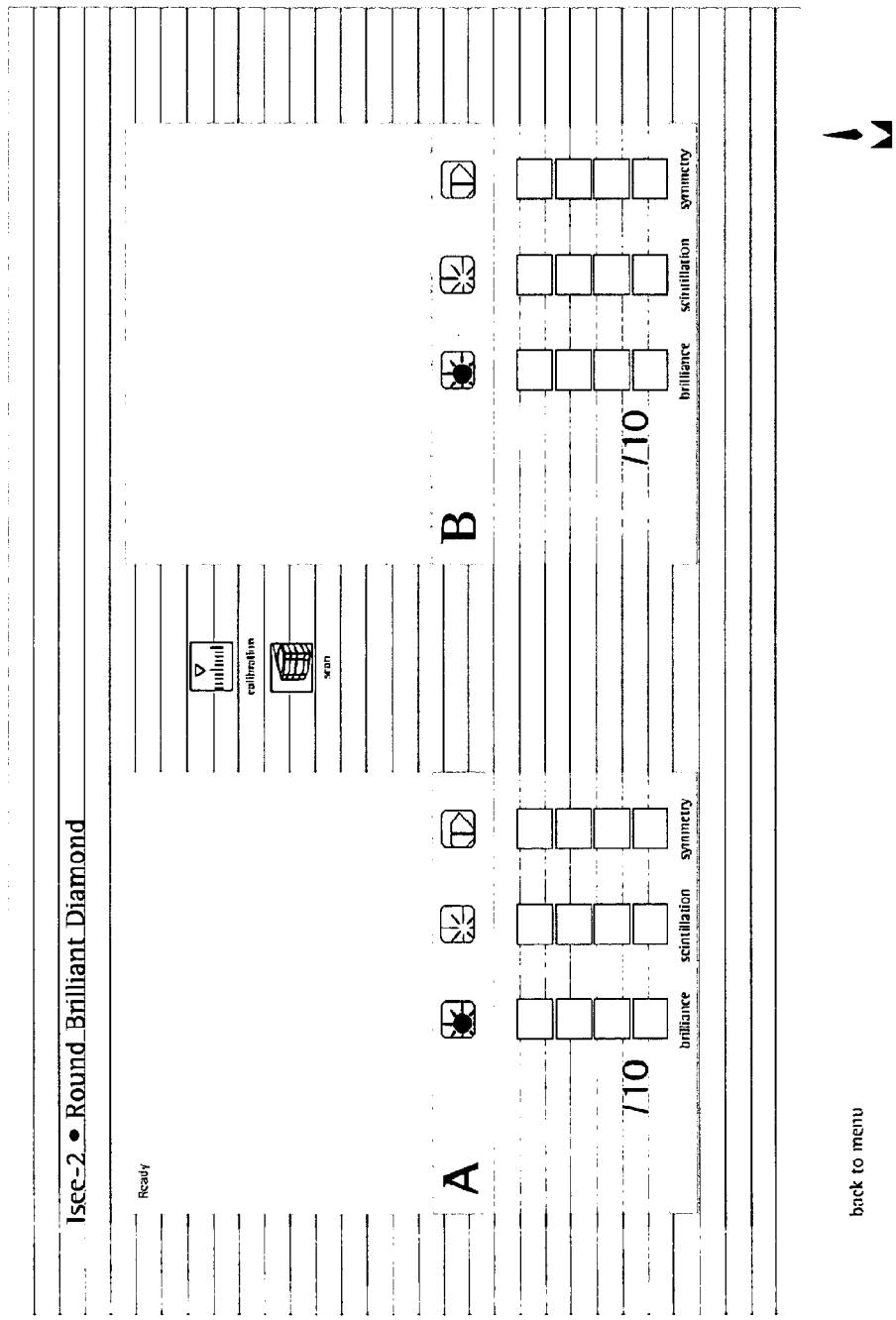
Figure 10E:
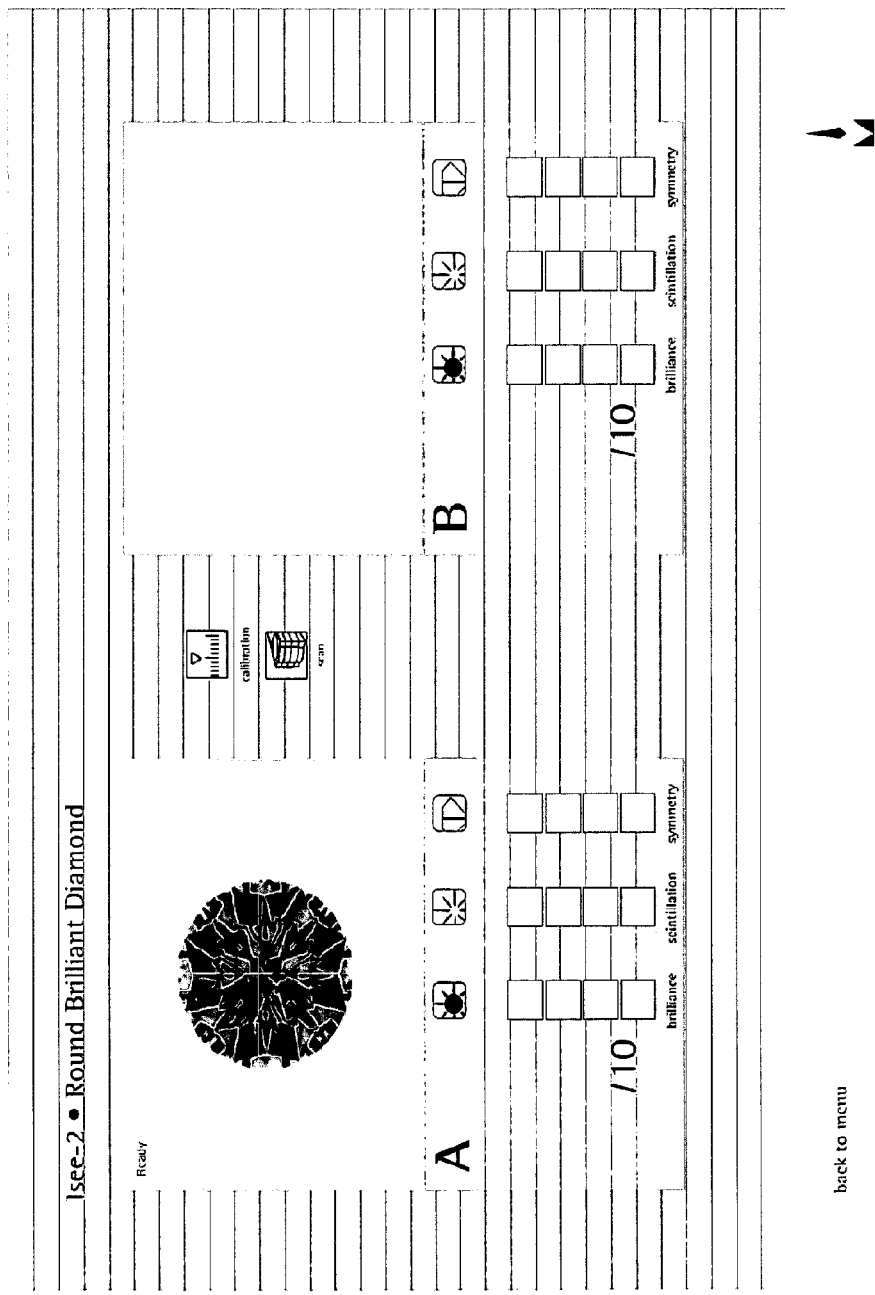
Figure 10F:
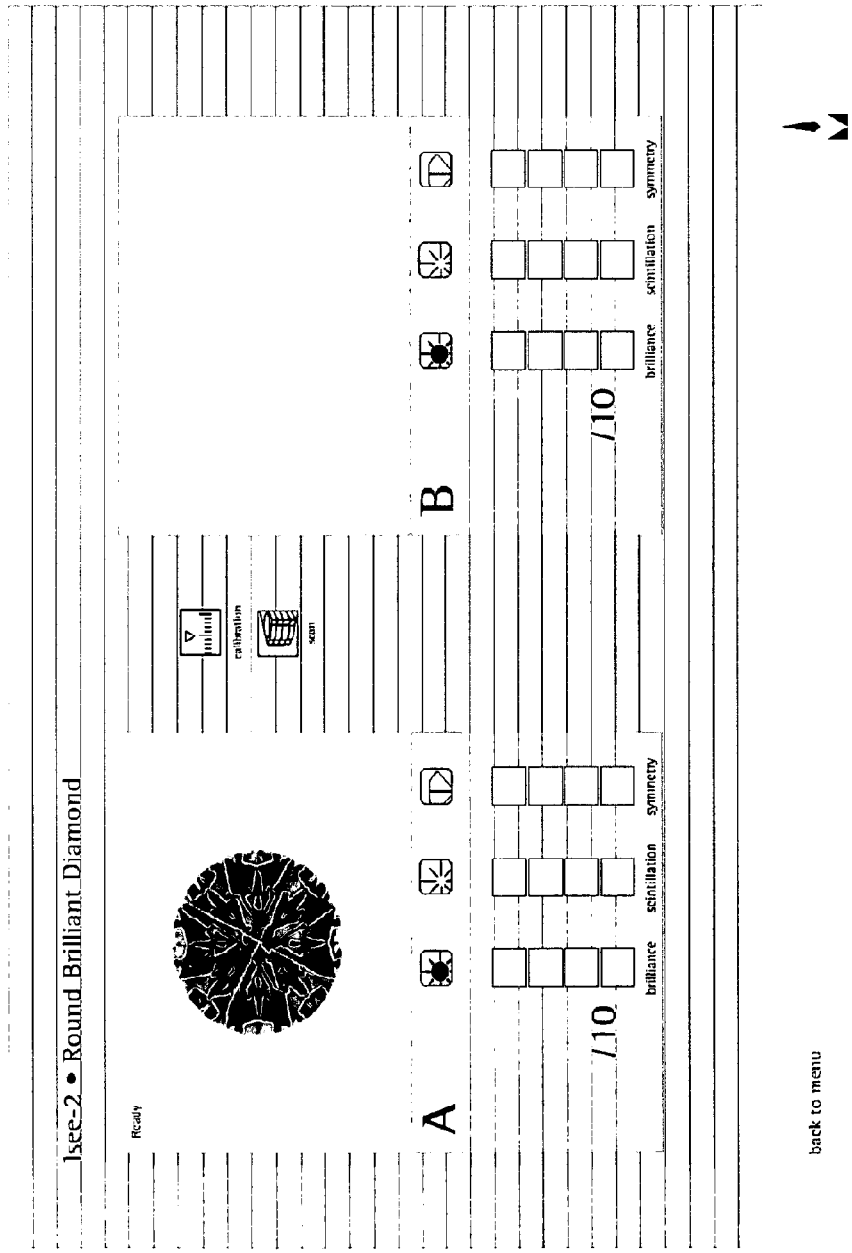

When calibration is finished the user clicks on the "Scan" button to initialize a scan of a diamond. FIG. 10*d* shows a screen shot of the initial scanning screen of the optical property evaluation module 58 without a diamond in place in the apparatus. A live image is displayed in the left hand box, although there is no diamond to view. Overlayed on the image is a circle and a pair of cross hairs which will be used to indicate the determined circumference of a diamond and its orientation about its axis of symmetry. Initially, the diamond is manually placed table-side down on the platform and centered approximately on axis 22. This may be assisted by observing the live image of the diamond displayed. FIG. 10*e* shows a screen shot of the scanning screen of the optical property evaluation module 58 with the diamond in place in the apparatus. The overlayed circle and cross hairs may then be moved (translated) and the diameter of the circle expanded or contracted by clicking and dragging operations of the mouse. The user manually adjust the circumference so that the diamond fits closely within the circle. By further clicking and dragging operations of the mouse, the user may rotate the crosshairs so that they are aligned with the symmetrical axes of the diamond as shown in FIG. 10*f*.

Figure 10G:
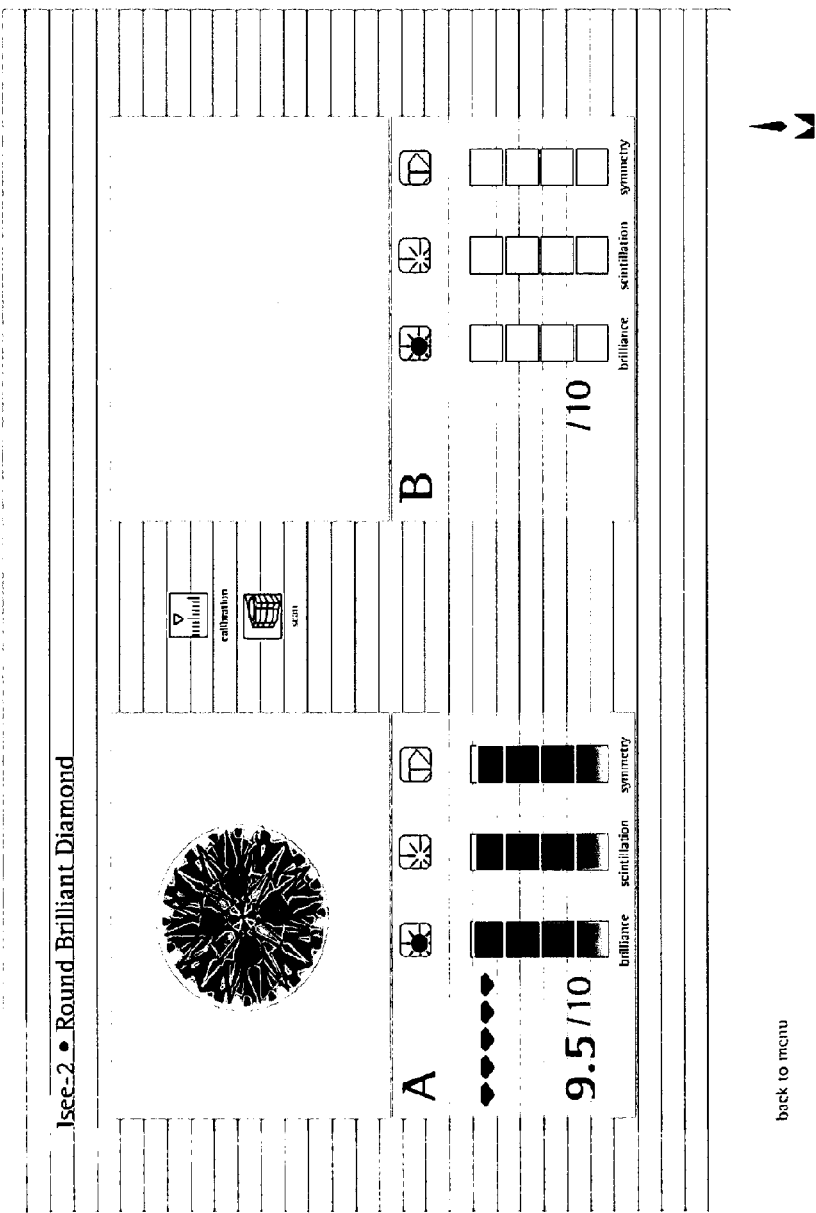

Then, by clicking once more on the "Scan" button, optical property evaluation module 58 is instructed to perform a scan of the diamond and to determine and display representations of three optical properties, namely brilliance, scintillation and symmetry. The stepper motor is controlled to rotate concave surface 26 to a "home" position and then to each of the series of rotational positions, for example 45 positions over a 90° range in steps of 2° Frames grabbed from camera 30 at each of these positions are stored in the hard disc drive of PC 36 for later display and for analysis. Algorithms for calculating these measurements have been described above. The results of analysis, i.e., the measurements of brilliance, scintillation and symmetry are then displayed beneath the image of the diamond as bar graph representations, as well as total or combined score of the three measurements represented as a score out of 10, as shown in FIG. 10*g*. The combined score is calculated with a weighting between the three properties of brilliance, scintillation and symmetry of 1:1:2 respectively. Thus, symmetry is twice as important as brilliance or scintillation to the total score. Other weightings are possible.

Figure 10H:
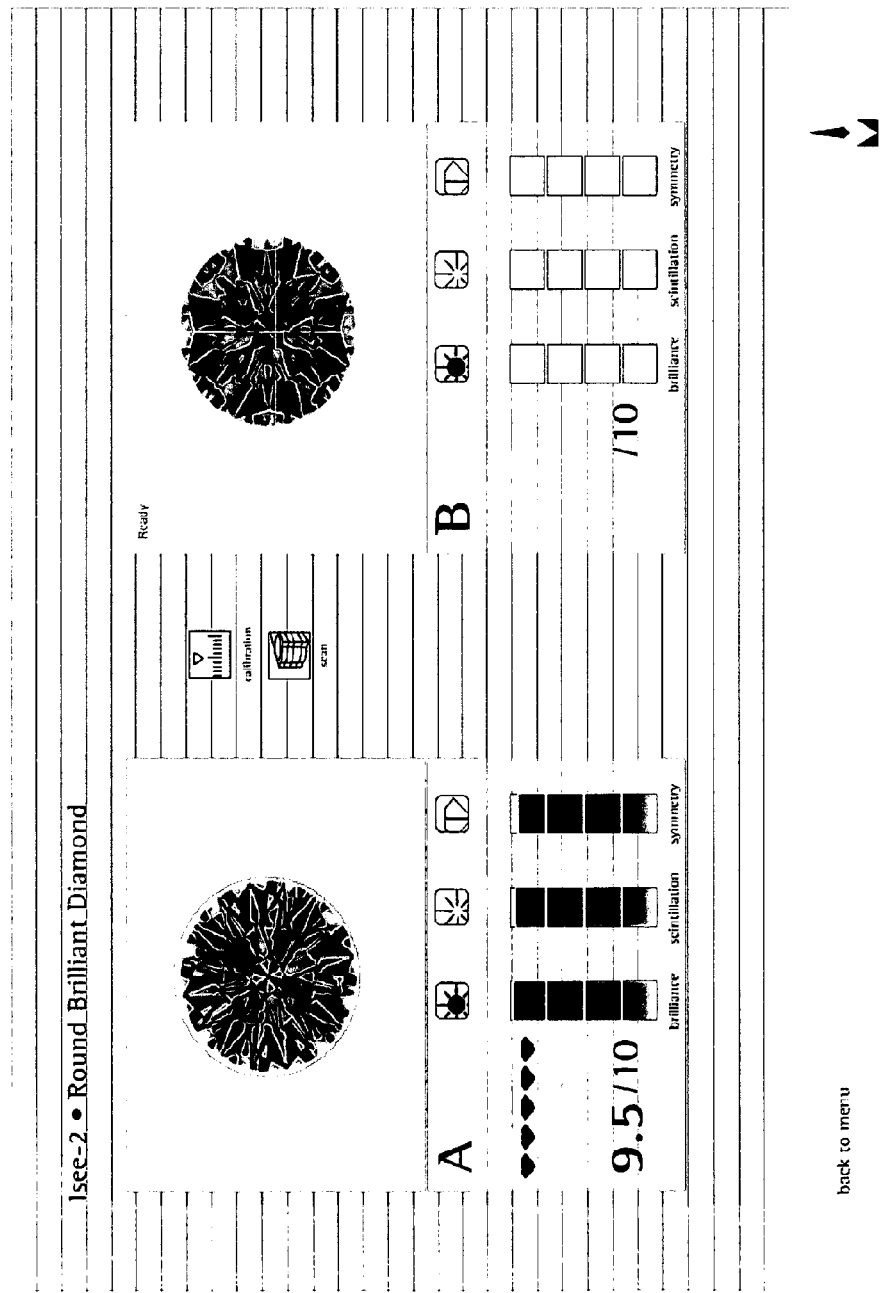
Figure 10I:
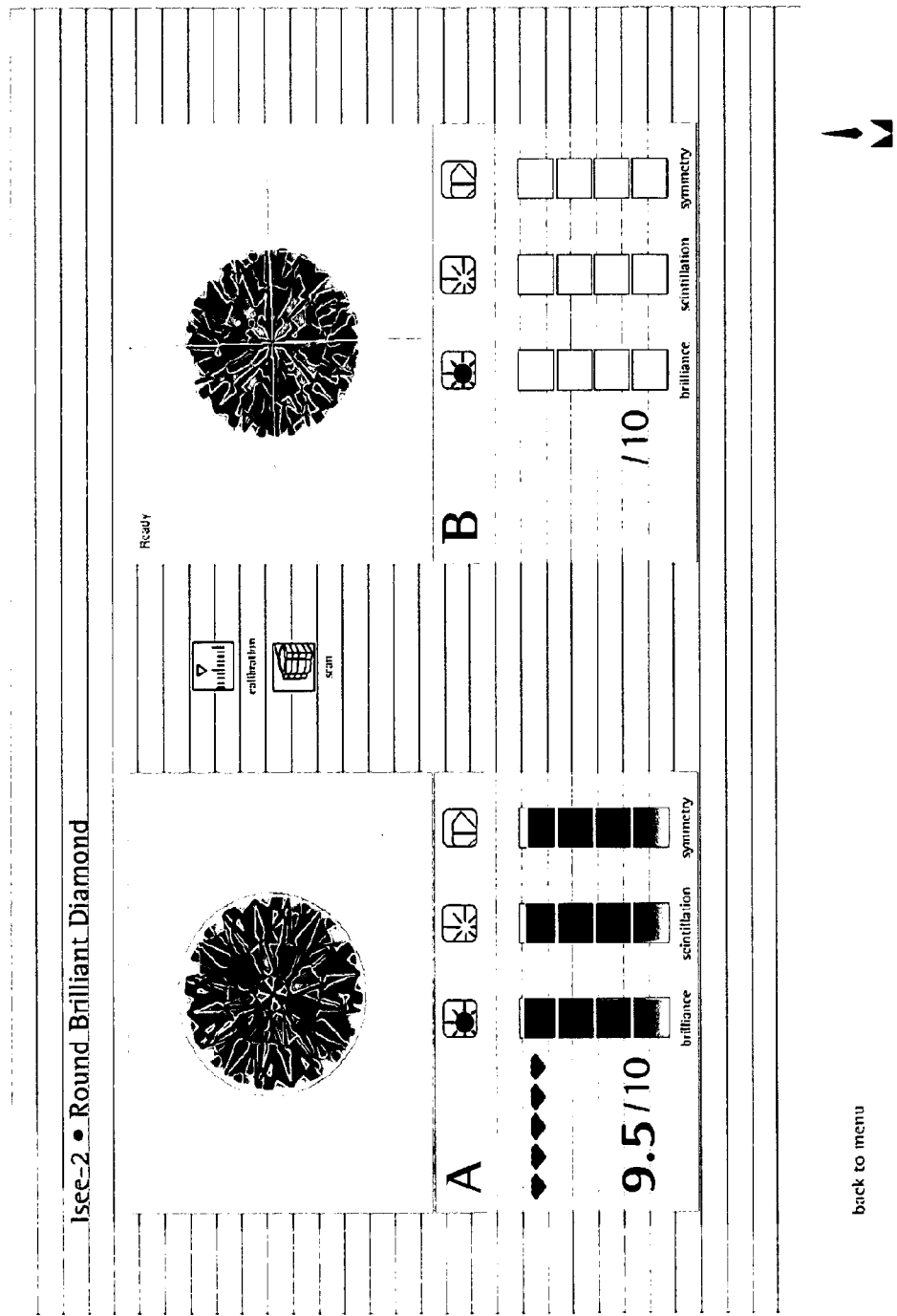

A user can compare two diamonds, scanned in two separate scanning operations, side by side both visually on PC 36 screen and in terms of objective measurements of the optical properties of brilliance, scintillation and symmetry. By removing the scanned diamond, replacing another diamond to be compared, by clicking on the right hand box and by again clicking on the "Scan" button, the process may repeated for the other diamond. Although the right hand box is used to display the image of the other diamond and its optical properties while the left hand box retains its images and optical properties of the original diamond. FIG. 10h shows a screen shot of the optical property evaluation module 58 with an image of the first diamond its optical properties displayed in the left hand box and an image of the newly placed other diamond in the right hand box. The process of arranging the displayed circle about the circumference of the newly placed diamond and orientating the cross hairs about its axis of symmetry is performed by mouse operations as described above. The results are shown in FIG. 10i.

Figure 10J:
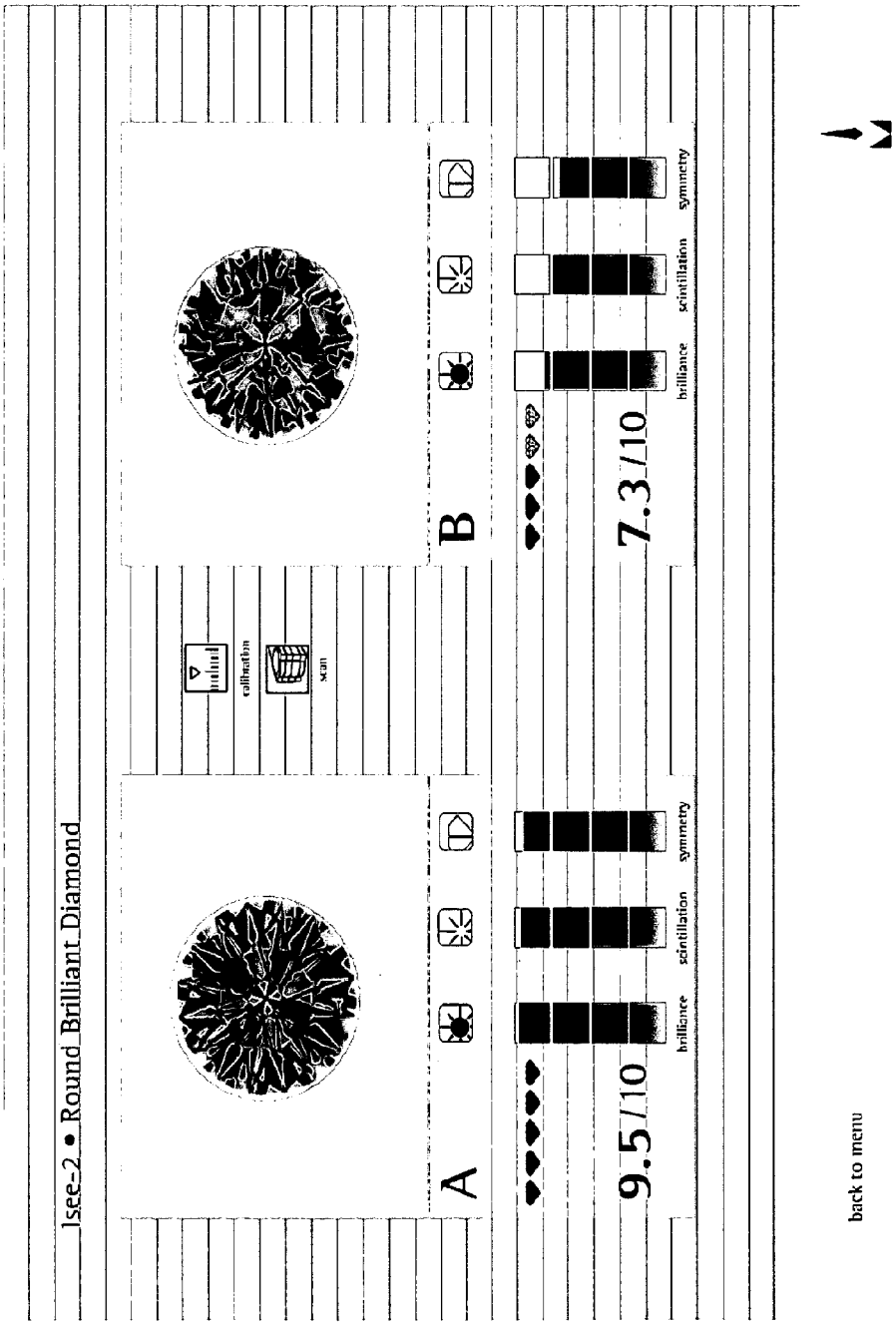

Then, by clicking once more on the "Scan" button once again, optical property evaluation module 58 is instructed to perform a scan of the newly placed diamond and to determine and display representations of three optical properties as well as the total score out of 10. This is shown in FIG. 10j. Thus, the user can compare the two diamonds, scanned in two separate scanning operations, side by side both visually on PC 36 screen and in terms of objective measurements of the optical properties of brilliance, scintillation and symmetry. Note that the images of the two diamonds displayed are moving images with the diamonds being shown illuminated in consecutive rotational positions of concave surface 26.

Thus, it can be seen that the present invention provides a unique opportunity for a consumer, who is likely to be an untrained observer, to measure the optical properties of one or more diamonds and to compare two or more diamonds in terms of objectively-determined optical properties for himself or herself. Furthermore, by having studied the gemology teaching pages, the consumer will have been provided with a basic understanding of the effect of the cut on light handling ability of diamond and will understand the significance of measured optical properties on the value of a diamond. Furthermore, the consumer will have been provided with a unique and improved retail experience.

Figure 11A:
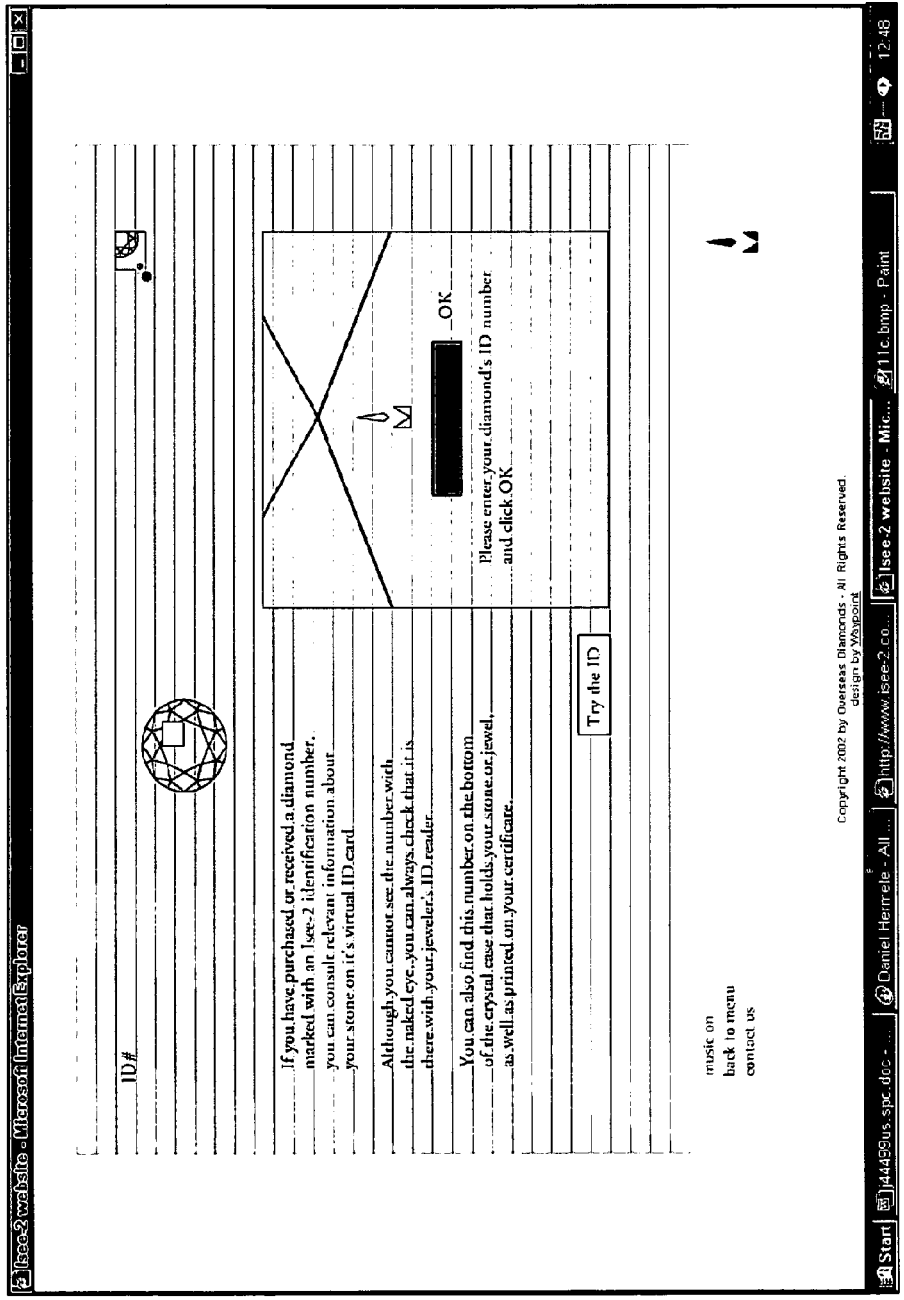
FIGS. 11a-c are screen shots of the user interface screen, of the gemology teaching and gemstone evaluation application for viewing reports on gemstones identified by gemstone code.
Figure 11B:
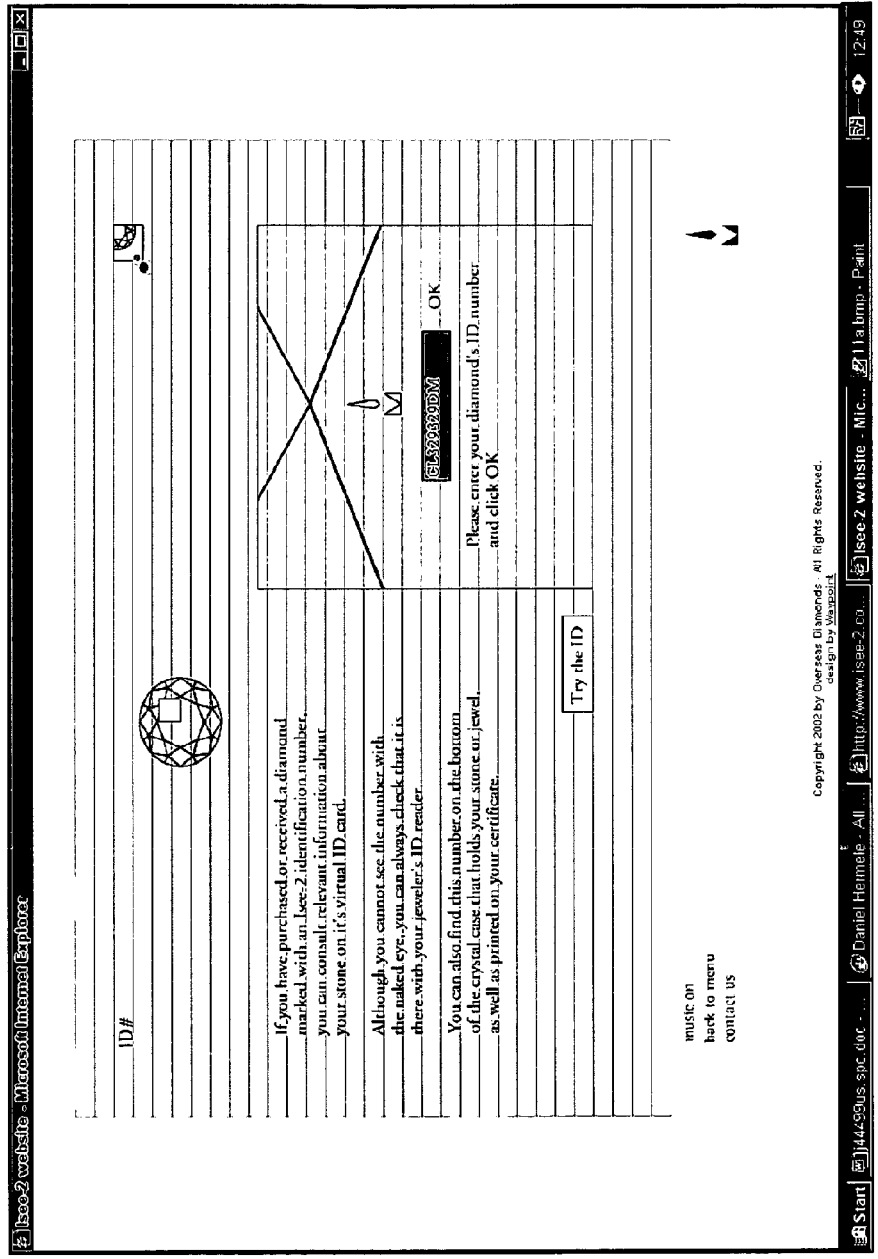
Figure 11C:
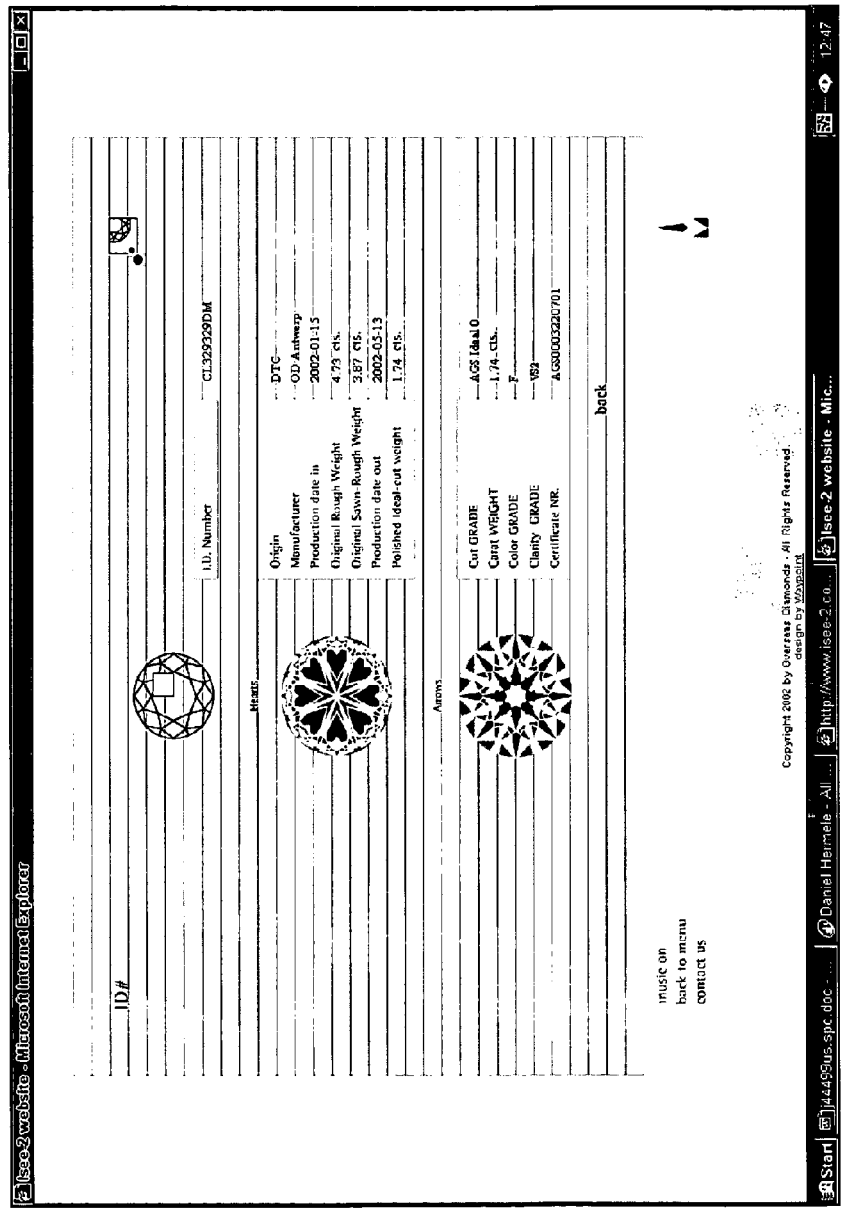

A further feature of the gemology teaching and gemstone evaluation application is the facility to view reports on gemstones identified by gemstone code using gemstone look-up module 62 as described above. FIGS. 11a is a screen shot of the user interface screen, of the gemology teaching and gemstone evaluation application, showing the a user entry box for entering a diamond's ID number. FIGS. 11b shows the user interface screen with a diamond number "CL329329DM" entered in the user entry box by typing at the keyboard of PC 36. By clicking on the "OK" button to the right of the user entry box, gemstone look-up module 62 is instructed to look up a previously generated record for the identified diamond and display it as shown in FIG. 11c. Various information may be displayed in such records relating to the origin and manufacturing of the cut diamond, such as such as the origin of the rough diamond, the manufacturer of the cut diamond, the weight of 1) the original rough, 2) the sawn-rough and 3) the polished ideal cut diamond, as well as the date of production of the cut diamond. Further information may be displayed relating to the grading of the cut diamond such as the American Gemological Society (AGS) cut grade, the carat weight, color grad, clarity grade and AGS certificate number. In alternative embodiments of the present invention, further information may be displayed such as previously generated optical property scores and total scores, as measured using gemstone evaluation application of the present invention, as well as a moving image of the diamond as captured using apparatus 44.

What is claim is:

1. A method of evaluating a gemstone, the method comprising:
   (a) presenting, to a user via a user interface, at least one user interface screen for operating a gemstone evaluation system that is configured to:
      i) capture images of the gemstone,
      ii) determine at least three optical properties of the gemstone by at least in part processing a plurality of captured images,
      iii) wherein the at least three optical properties are selected from the group of:
      brilliance, scintillation, fire, and light symmetry,
      iv) wherein the determination of the brilliance is based, at least in part, on a first analysis of pixels of the plurality of captured images,
      v) wherein the determination of the scintillation is based, at least in part, on a second analysis of pixels of the plurality of captured images,
      vi) wherein the determination of the fire is based, at least in part, on a third analysis of pixels of the plurality of captured images, and
      vii) wherein the determination of the light symmetry is based, at least in part, on a fourth analysis of pixels of the plurality of captured images; and
   (b) sending, by the user, utilizing the at least one interface screen, instructions to the gemstone evaluation system to perform an evaluation of the gemstone, hereby causing the gemstone evaluation system to:
      i) capture the images of the gemstone, and
      ii) determine each of the at least three optical properties based, at least in part, on the plurality of captured images.

2. The method according to claim 1, further comprising presenting, via the user interface, user interface screens for showing results of the evaluation.

3. The method according to claim 1, wherein in step (b) each of the plurality of captured images is captured under the same illumination arrangement.

4. The method according to claim 1, wherein the evaluation comprises:
   determining a measure for each of the at least three optical properties at least partially based on the plurality of captured images; and
   assigning, based on the determined measures, at least one total score to the gemstone.

5. The method according to claim 1, wherein the user is a potential purchaser during a retail experience.

6. A gemstone evaluation system, comprising:
   at least one specialized computer machine, comprising:
   a non-transient memory having at least one region for storing particular computer executable program code; and
   at least one processor for executing the particular program code stored in the memory;
   wherein the gemstone evaluation system is configured to:
      i) capture images of the gemstone,
      ii) determine at least three optical properties of the gemstone by at least in part processing a plurality of captured images,
      iii) wherein the at least three optical properties are selected from the group of:
      brilliance, scintillation, fire, and light symmetry,
      iv) wherein the determination of the brilliance is based, at least in part, on a first analysis of pixels of the plurality of captured images,
      v) wherein the determination of the scintillation is based, at least in part, on a second analysis of pixels of the plurality of captured images,
      vi) wherein the determination of the fire is based, at least in part, on a third analysis of pixels of the plurality of captured images, and vii) wherein the determination of the light symmetry is based, at least in part, on a fourth analysis of pixels of the plurality of captured images;

wherein the particular program code is configured to at least perform the following operations:

(a) presenting, to a user, via a user interface, at least one user interface screen for operating the gemstone evaluation system, and (b) receiving, from the user, utilizing the at least one interface screen, instructions for the gemstone evaluation system to perform an evaluation of the gemstone, hereby causing the gemstone evaluation system to:

i) capture the images of the gemstone, and ii) determine each of the at least three optical properties based, at least in part, on the plurality of captured images.

7. The system according to claim 6, wherein the particular program code is further configured to present, via the user interface, user interface screens for showing results of the evaluation.

8. The system according to claim 6, wherein the system comprises a gemstone measuring apparatus including an illumination arrangement, operative when each of the plurality of captured images is captured.

9. The system according to claim 6, wherein the evaluation comprises:

determining a measure for each of the at least three optical properties at least partially based on the plurality of captured images; and assigning, based on the determined measures, at least one total score to the gemstone.

10. The system according to claim 6, wherein the user is a potential purchaser during a retail experience.

11. The system according to claim 6, wherein the system comprises a gemstone measuring apparatus configured to capture the images, and wherein the determination of the at least three optical properties of the gemstone is performed remotely from the apparatus.

\* \* \* \* \*